US011135082B2

(12) United States Patent
Hayes

(10) Patent No.: US 11,135,082 B2
(45) Date of Patent: Oct. 5, 2021

(54) METHODS AND DEVICES FOR REDUCING PREGNANCY-RELATED AND POST-NATAL LOWER BACK PAIN

(71) Applicant: AMAZING BRACE, LLC, Odessa, FL (US)

(72) Inventor: Victor Hayes, Odessa, FL (US)

(73) Assignee: AMAZING BRACE, LLC, Odessa, FL (US)

( * ) Notice: Subject to any disclaimer, the term of this patent is extended or adjusted under 35 U.S.C. 154(b) by 441 days.

(21) Appl. No.: 16/234,403

(22) Filed: Dec. 27, 2018

(65) Prior Publication Data

US 2019/0269544 A1  Sep. 5, 2019

Related U.S. Application Data

(63) Continuation-in-part of application No. 14/993,241, filed on Jan. 12, 2016, now abandoned.
(Continued)

(51) Int. Cl.
| | | |
|---|---|---|
| *A61F 5/03* | (2006.01) | |
| *A61F 5/32* | (2006.01) | |
| *A61F 5/02* | (2006.01) | |

(52) U.S. Cl.
CPC ............. *A61F 5/03* (2013.01); *A61F 5/024* (2013.01); *A61F 5/028* (2013.01); *A61F 5/32* (2013.01)

(58) Field of Classification Search
CPC .... A61F 5/03; A61F 5/32; A61F 5/024; A61F 5/028; A61F 5/01; A61F 5/00; A61F 5/026; A61F 5/37; A61F 5/05808
See application file for complete search history.

(56) References Cited

U.S. PATENT DOCUMENTS

| 3,273,563 A | * | 9/1966 | Bonang | ................... A61F 5/03 450/155 |
| 6,159,070 A | * | 12/2000 | Schwartz | ............... A41C 1/10 2/406 |

(Continued)

*Primary Examiner* — Tarla R Patel
(74) *Attorney, Agent, or Firm* — Kristina Castellano; Castellano PLLC

(57) ABSTRACT

Provided are methods and systems of reducing, treating, and/or preventing back pain in an individual, such as a pregnant or post-partum individual, that include changing the center of gravity of the individual by the methods set forth herein. In particular, the methods herein include shifting the center of gravity in the individual to a desired center of gravity. The methods include applying modifiable lifting forces to a lower abdomen of the individual using a pully system, under the belly of the individual toward the desired center of gravity; and applying one or more vector forces from an anterior side of the individual toward the desired center of gravity. Also provided are methods that include applying a lumbar support, as described herein to an individual. Also provided herein are adjustable, modular lumbar support devices that may be used to provide lumbar and/or belly support for individuals having belly weight to achieve the present methods. According to non-limiting example embodiments, support or brace devices provided herein may be worn by pregnant women at various stages throughout a woman's pregnancy, and/or post-partum and may be adjusted to naturally contour/conform to the woman's anatomy, which changes throughout pregnancy. Further provided are kits that include at least one lumbar support device provided herein, which kits may optionally include instructions for proper application and/or adjustment of the lumbar support device and/or accessories for use with the present methods, systems and/or devices.

19 Claims, 63 Drawing Sheets

Related U.S. Application Data

(60) Provisional application No. 62/102,568, filed on Jan. 12, 2015, provisional application No. 62/610,925, filed on Dec. 27, 2017.

(56) References Cited

U.S. PATENT DOCUMENTS

| | | |
|---|---|---|
| 6,336,908 B1 | 1/2002 | Slautterback |
| 7,101,348 B2 | 9/2006 | Garth |
| 9,089,409 B2 | 7/2015 | Wu |
| 9,655,761 B2 | 5/2017 | Joseph |
| 2013/0261464 A1 | 10/2013 | Singh |
| 2014/0128788 A1 | 5/2014 | Marshall |
| 2017/0135842 A1 | 5/2017 | Tsuchiya |

* cited by examiner

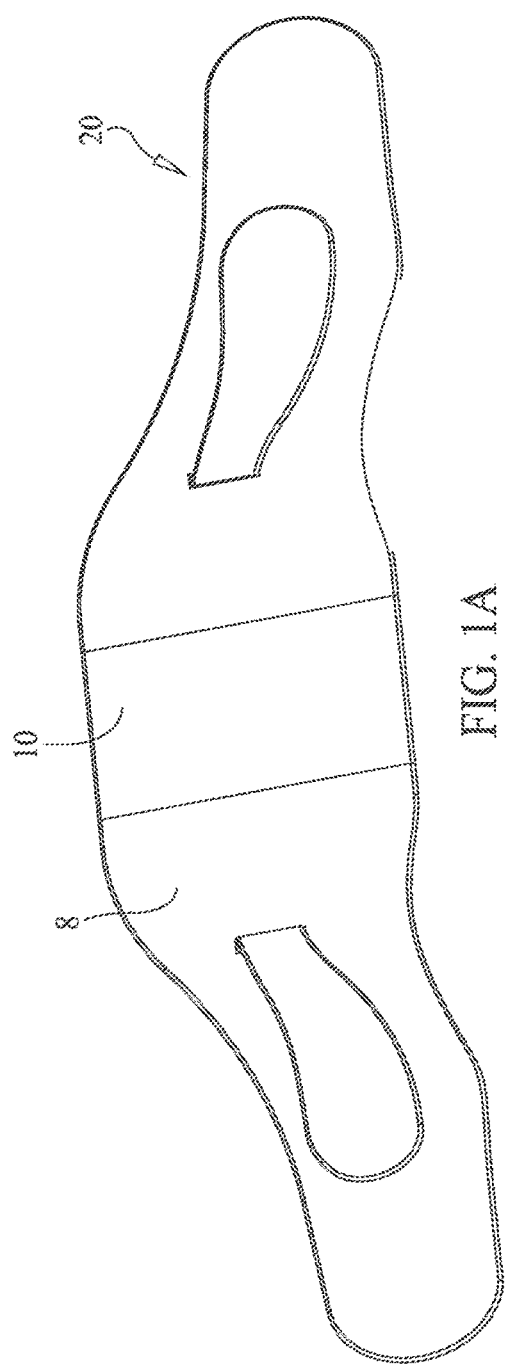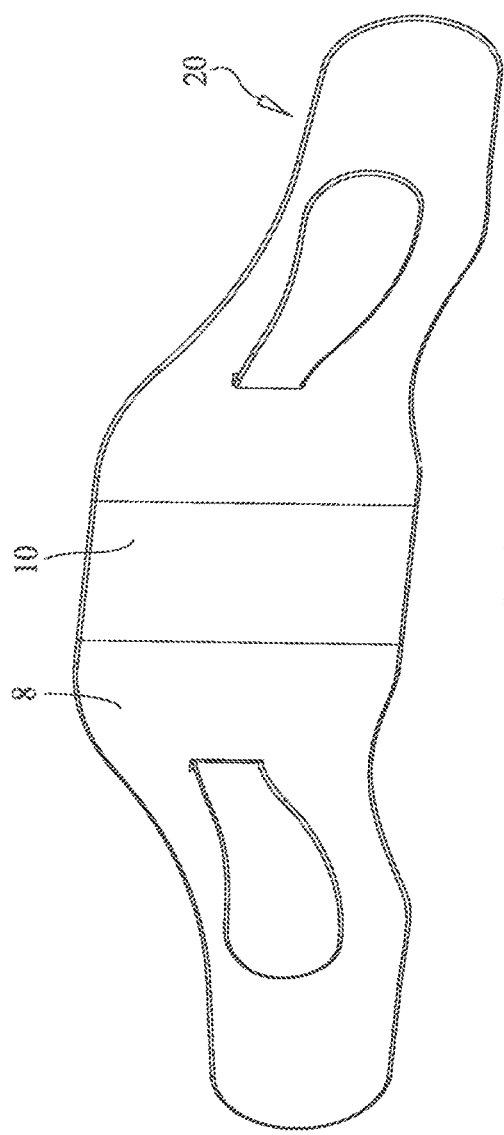

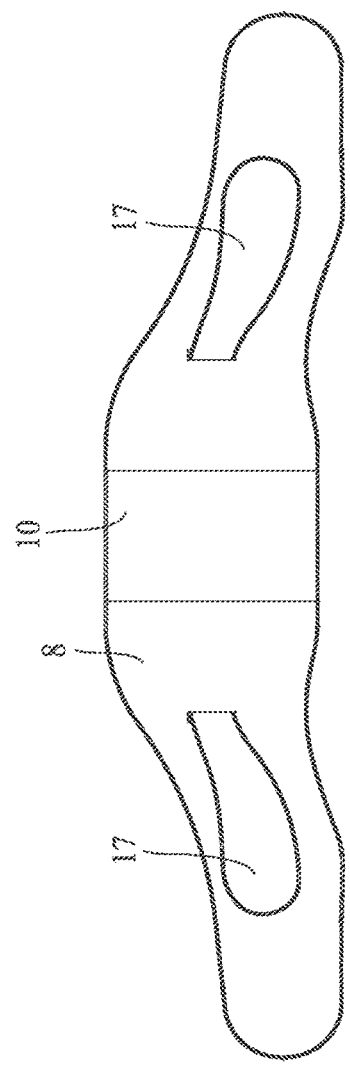
FIG. 1C
FIG. 1D
FIG. 1E
FIG. 1F

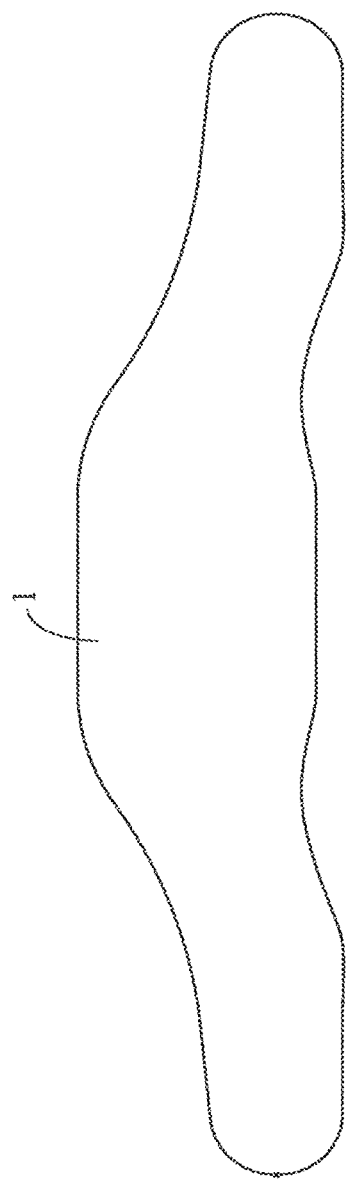
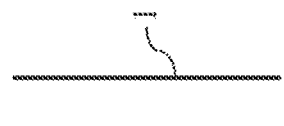
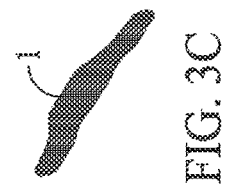
FIG. 3A
FIG. 3B
FIG. 3C

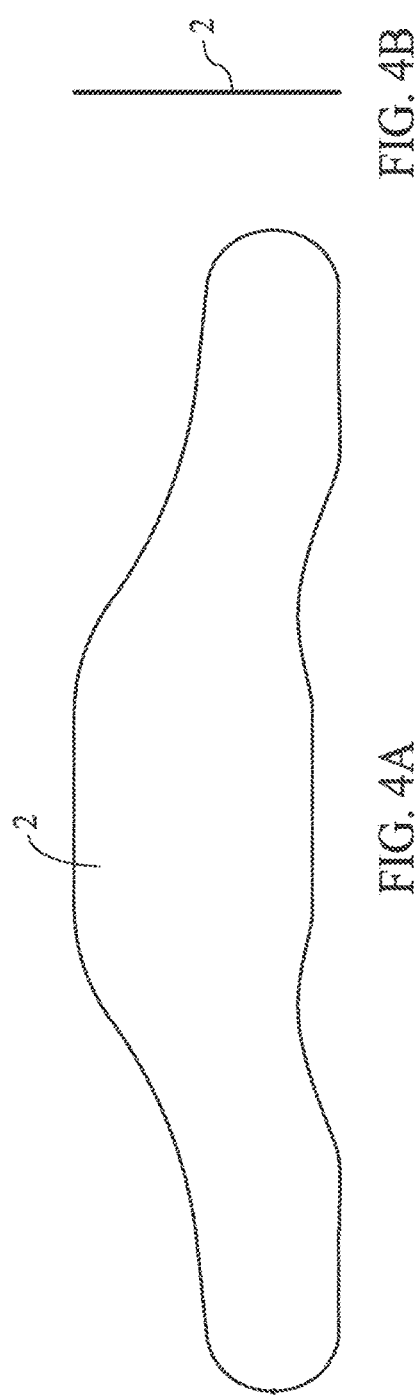
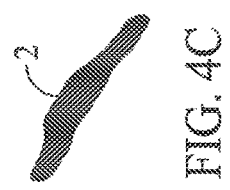
FIG. 4A
FIG. 4B
FIG. 4C

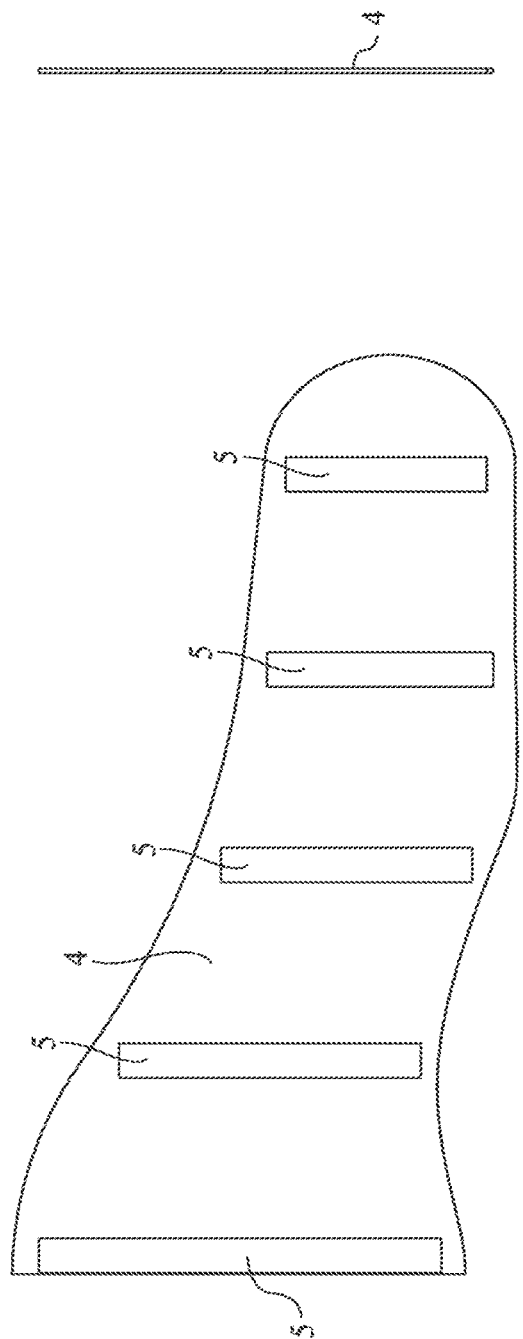

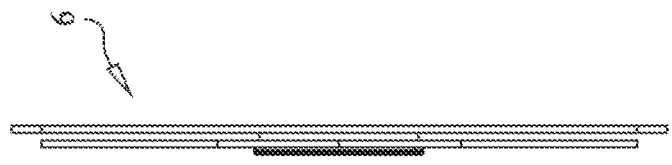
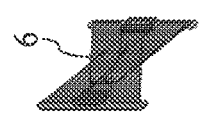
FIG. 7C
FIG. 7D
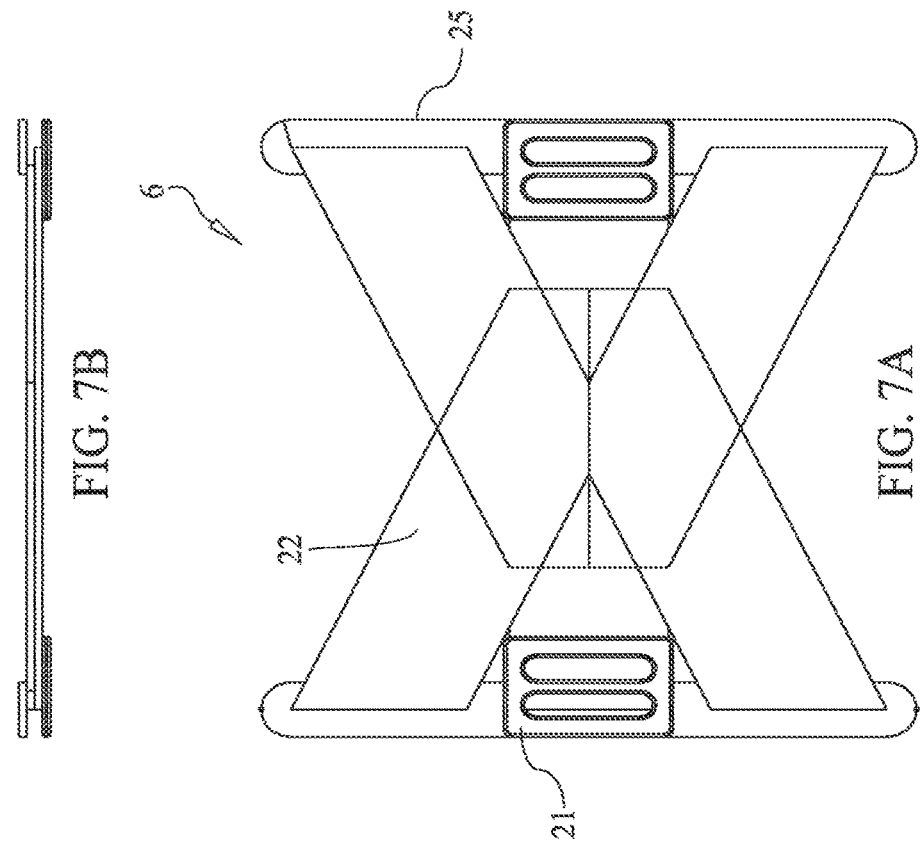
FIG. 7B
FIG. 7A

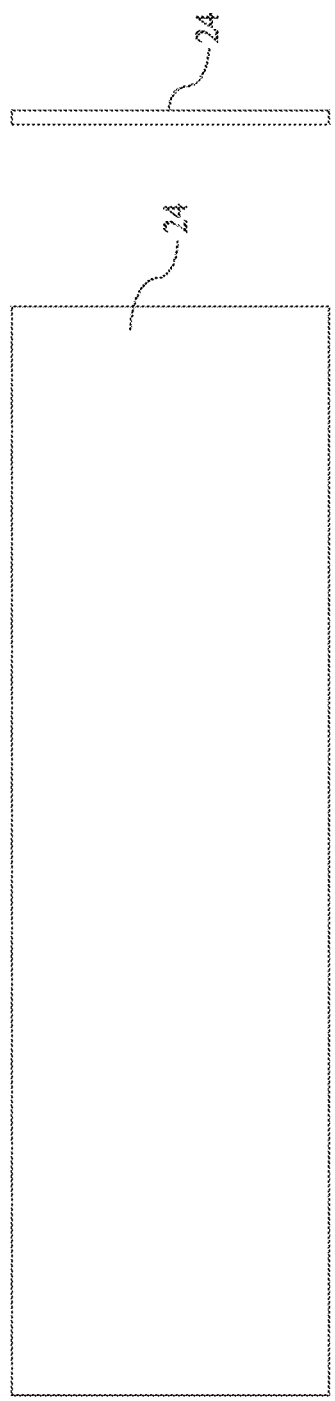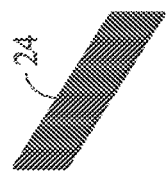

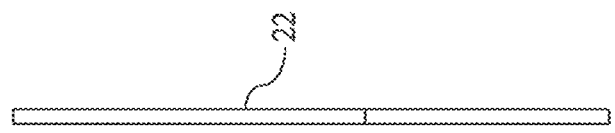
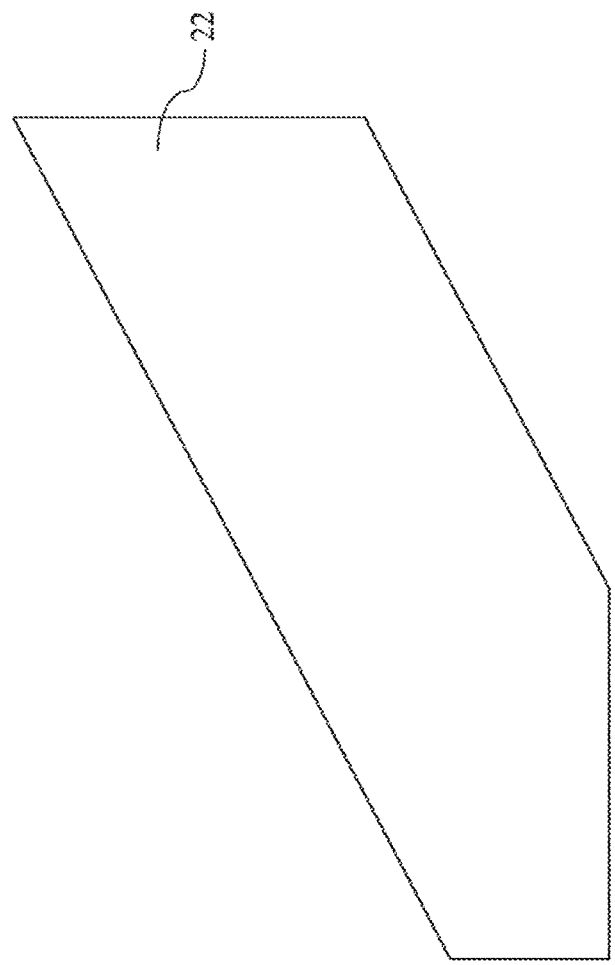

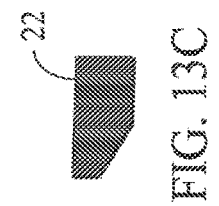
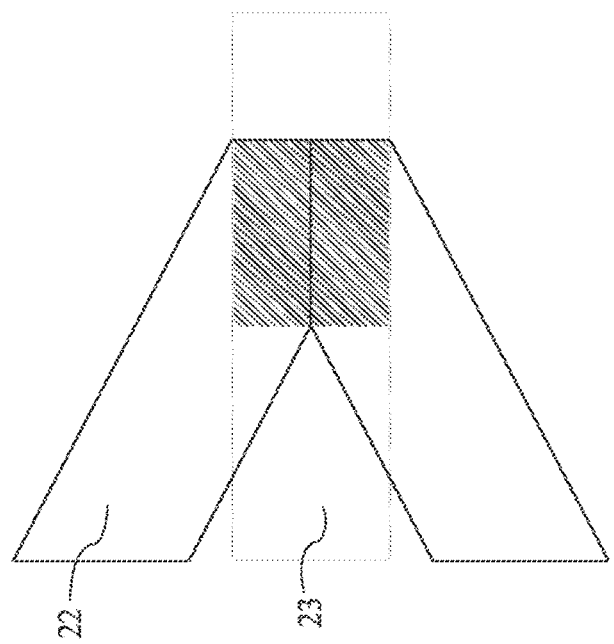
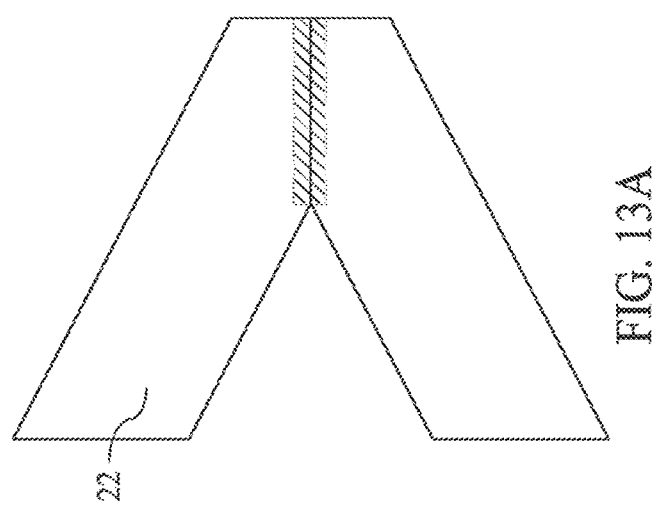

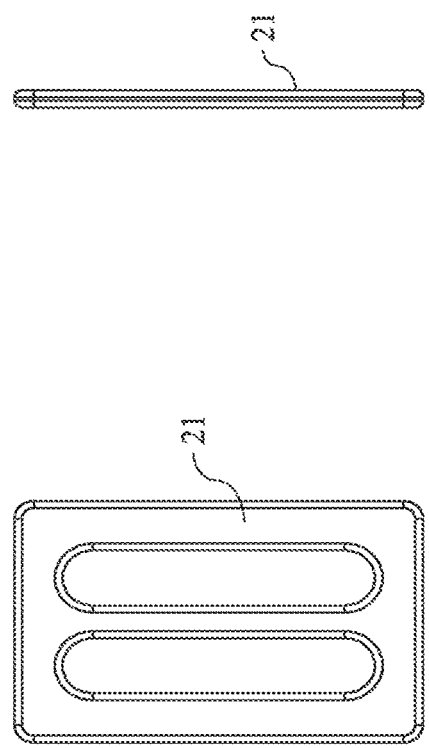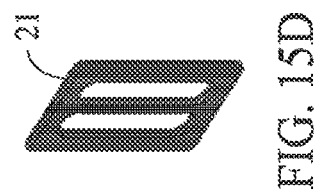

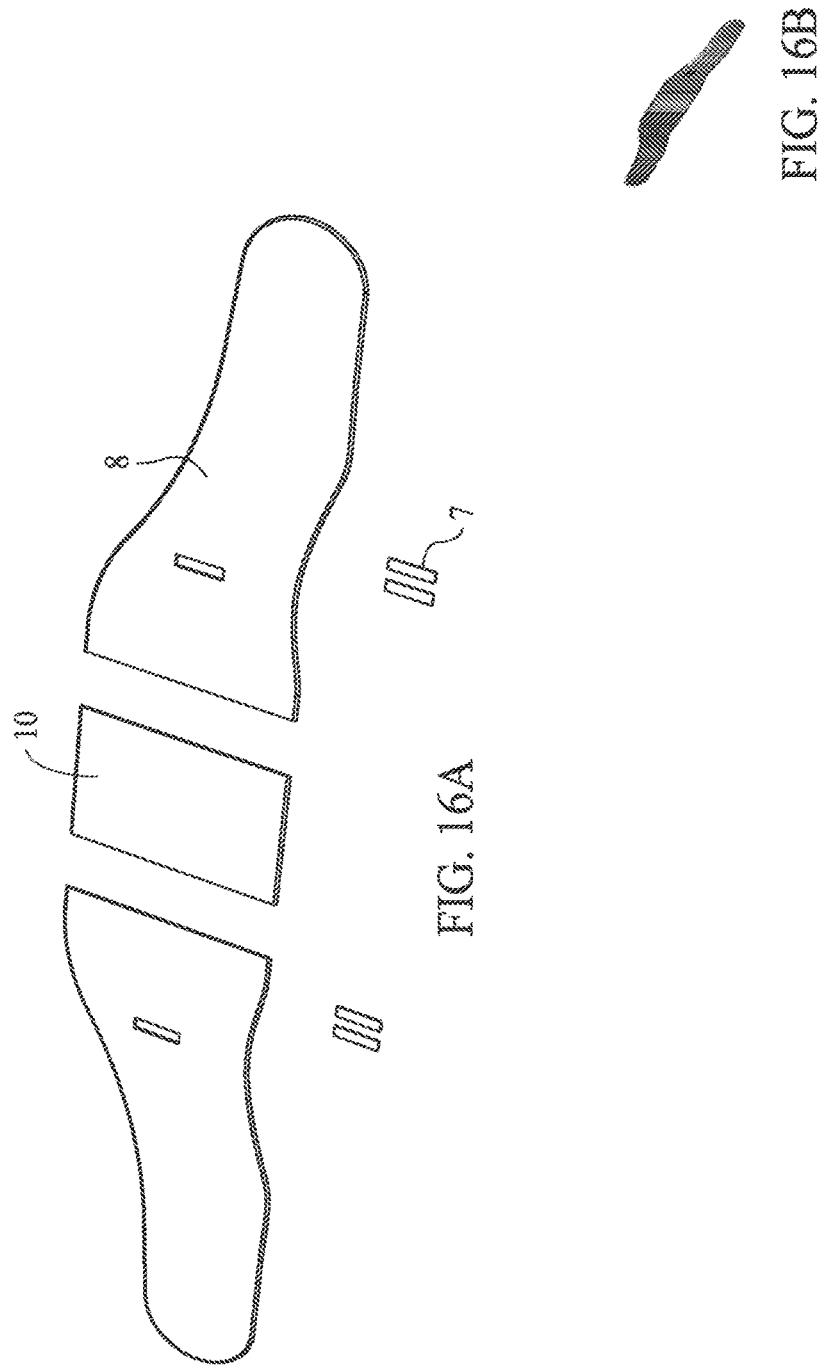

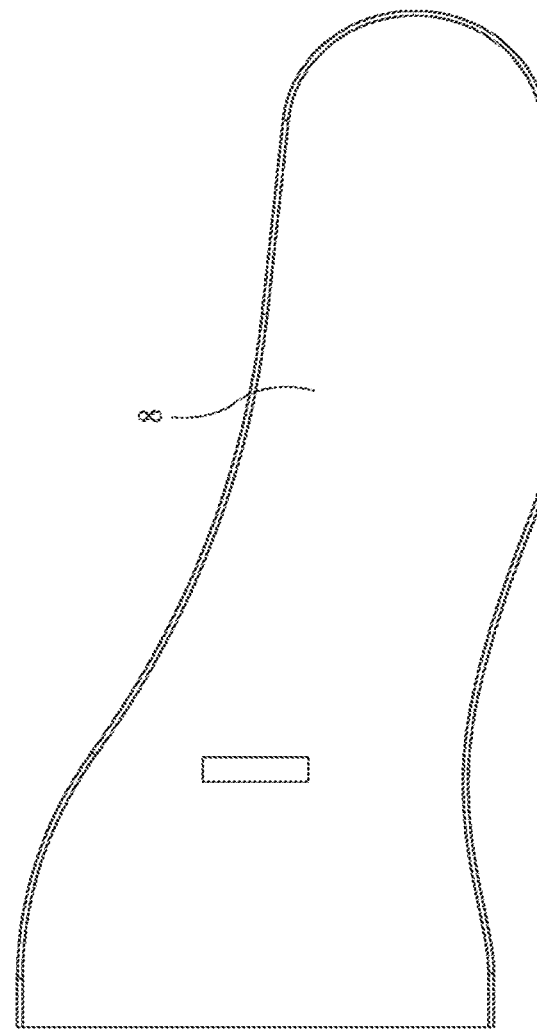
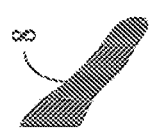
FIG. 17A
FIG. 17B
FIG. 17C

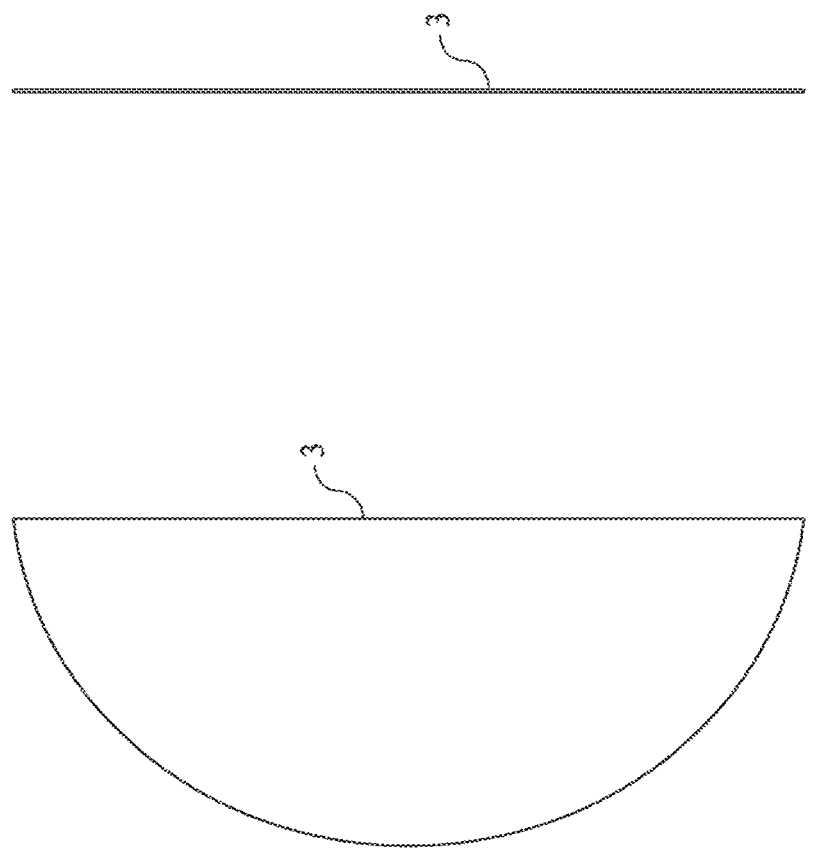
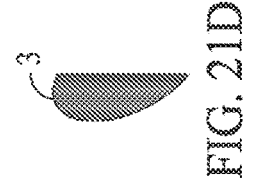

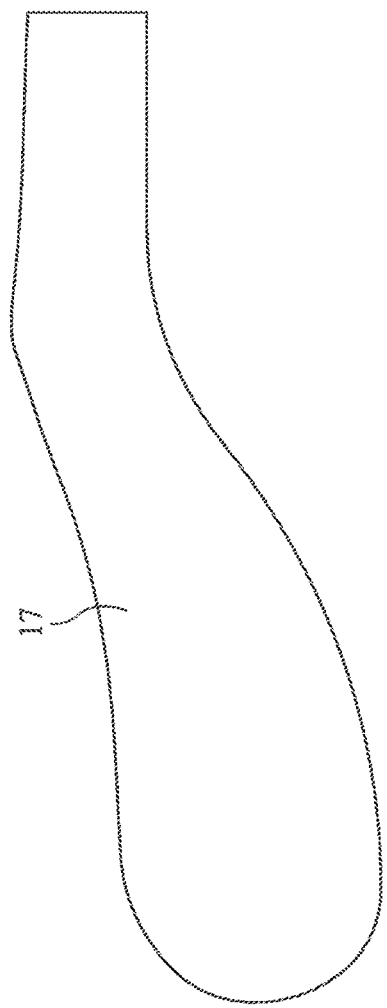
FIG. 22A
FIG. 22C
FIG. 22B
FIG. 22D

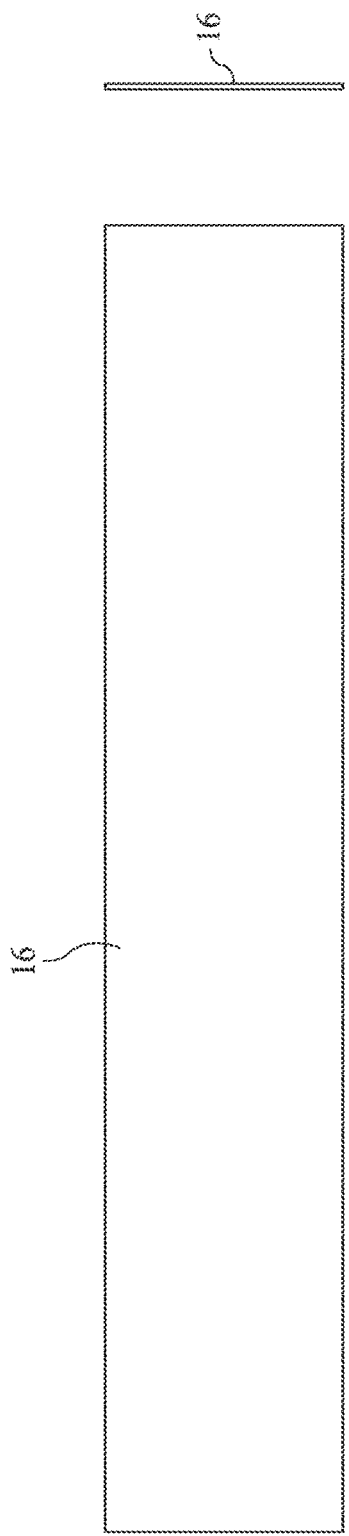
FIG. 23A
FIG. 23B
FIG. 23C
FIG. 23D

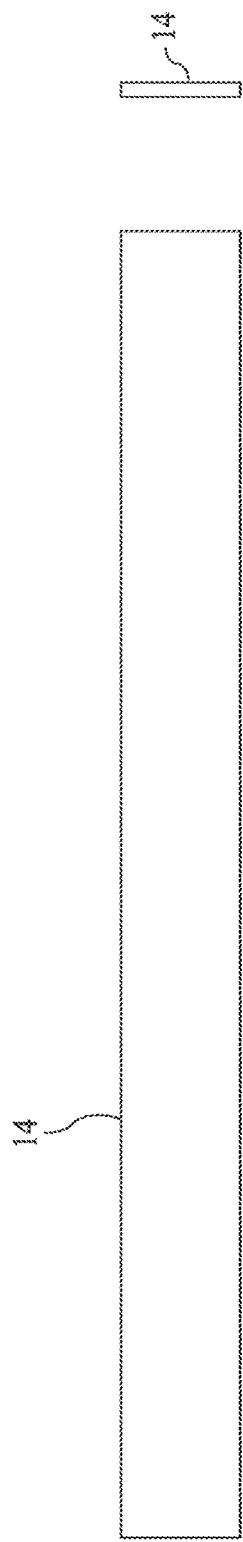
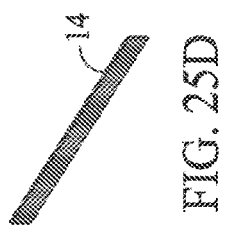
FIG. 25A
FIG. 25B
FIG. 25C
FIG. 25D

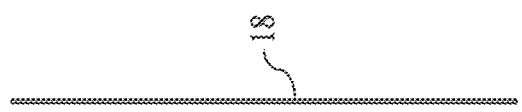
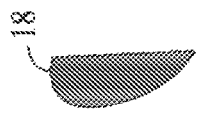
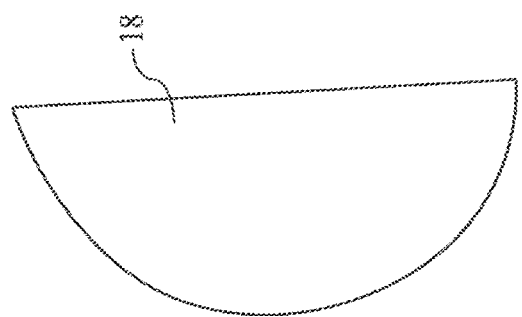
FIG. 28A  FIG. 28B  FIG. 28C  FIG. 28D

FIG. 55

Internal View of Force Vectors During Adjustment Process BabyBrace™

| Forces | Forces |
| --- | --- |
| Adjustment arm-Elastic –Pulley System- Main arm | Adjustment arm-Elastic –Pulley System- Main arm |

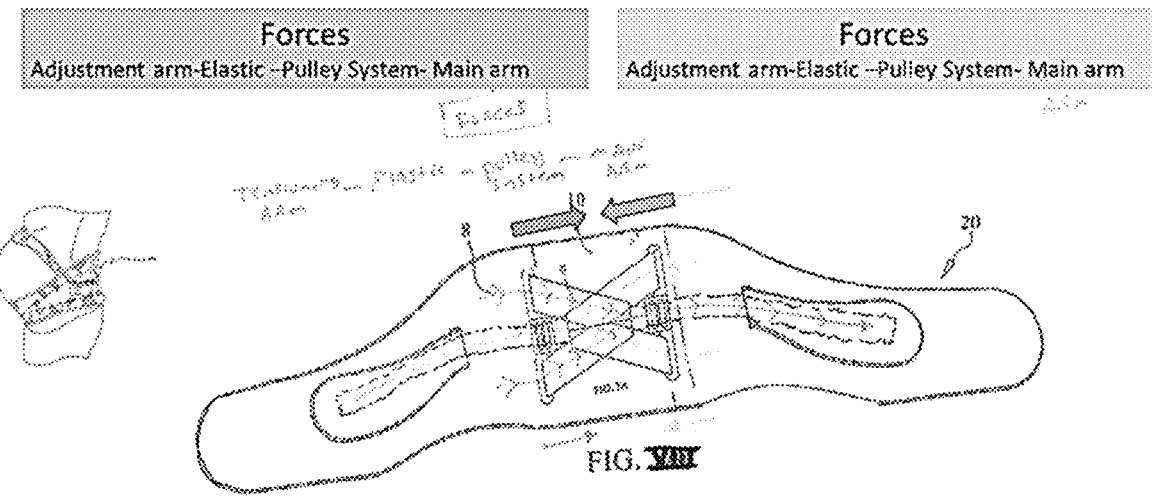

FIG. 56

Cross-section of BabyBrace™ Pulley System(Expanded)

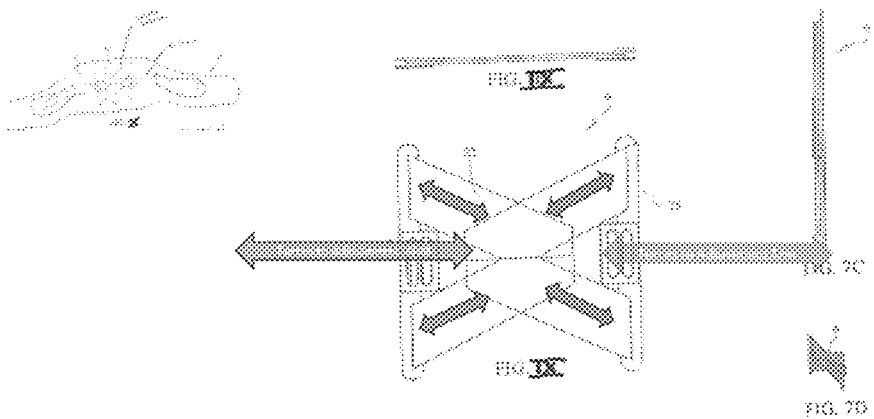

The design and elastic material within the pulley system reduces the pressure exerted by the posterior brace. The pulley system will reduce lordosis without excessive compressive posterior force exertion via the back of the brace.

1) The elastic material within the pulley system will also pull in both directions distributing forces to the adjustment arms and main arms of the brace (Equilibration Process).
2) More Force is transferred from the pulley system back to the anterior bracing arms (all 4) because of the orientation & separation of the pulleys, their material, and their elastic connection to the adjustment arms
3) The resistance properties of the pulley systems material will alter the type and strength of the forces produced by the braces.
4) Simply changing orientation of the pulley system connections, or using different materials within the Adjustment arm Pulley system: This will alter its vector of pull, type of forces and overall function of the brace.

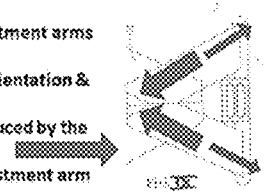

Brace Extender Attachment with Velco to increase Size & Expand BabyBrace ™

FIG. 75

BabyBrace® (Detailed) Fitting Instructions

- 1) Measure the Waist Circumference
- 2) Sizing Scale should be used to Guide sizing process
  - A) can use sample braces to Confirm Size and Fit
  - B) In the first and second trimester size up 1 size from table
  - C) In the Third trimester (True to size based on scale to right)
- 3) Before fitting: Pull the brace main arms taught so the adjustment arms are within their opening *This "Unloads" the braces Adjustment System and you Should not see the elastic)*

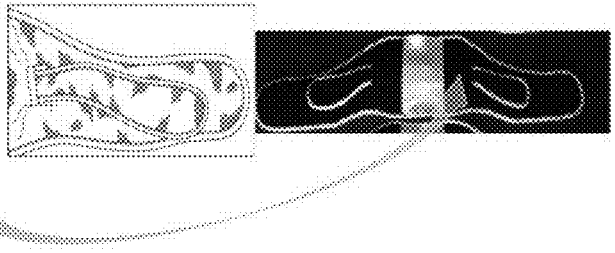

FIG. 76

BabyBrace® (Detailed) Fitting Instructions

- 4) Place left Main brace arm on the lower belly (below the Umbilicus)
- 5) close (Seal) the main arms by using Velcro attachment, the brace be should lay on the lower abdomen below the umbilicus and be comfortable...never too snug (tight)
  - (And should have a minimum 5-6" Main Brace Arms overlap)
- 6) Let the patient pull both adjustment arms: rest the left arm on the upper (or mid-) abdomen and then use the Velcro to attach (seal)the Right Are
  - The adjustment arm should always attach to one another
  - *Preferably on upper abdomen or Mid-Abdomen over umbilicus is ok too*
- 7) The Adjustment arms can then be readjusted to the most comfortable position. The patient should be instructed to do this. (See Example to left)

① Seal the main straps

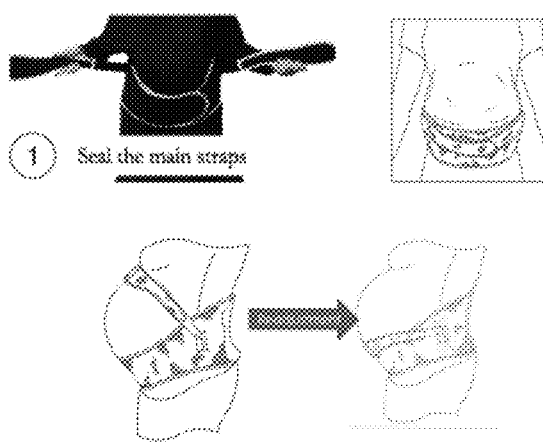

FIG. 77

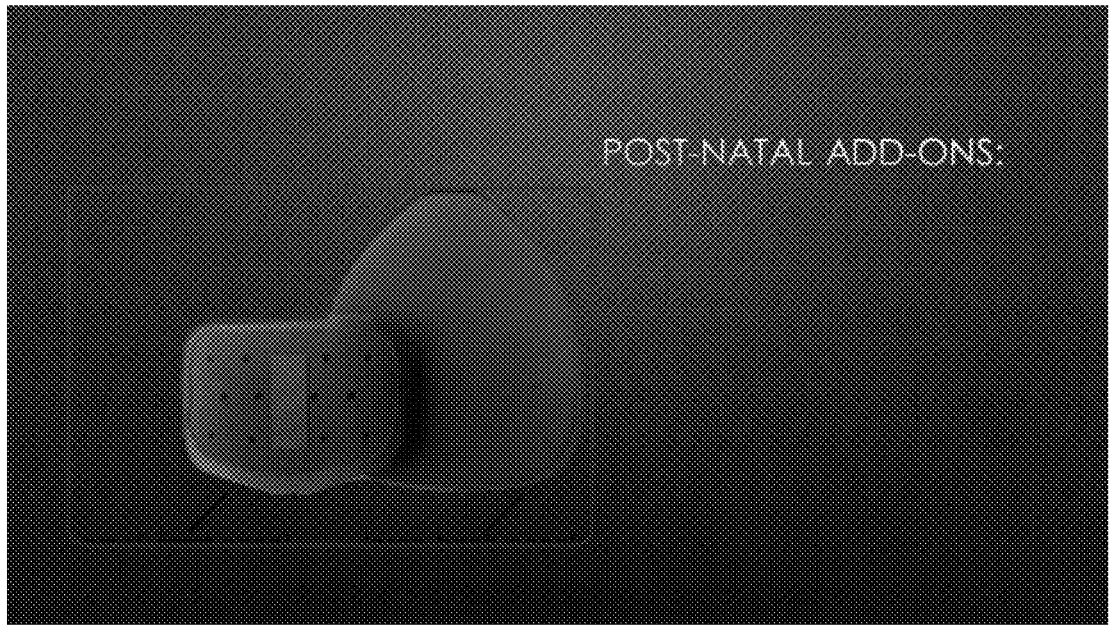

FIG. 78

BRACE ADD-ONS (POSTERIOR PANEL)
- 1) The Posterior Panel can be used at the discretion of the prescriber and / or Physician
  - (But must be custom Fit By a medical professional without exception) It is pre-molded already but can be adjusted if necessary
- 2) The posterior panel should ALWAYS be placed on the inner posterior aspect of main brace and attached via the Velcro square
- 3) The posterior panels extra padding should be removed, and a heat gun can be used to heat up the panel for customization
- 4) once the brace is heated the thermoelastic plastic can be hand molded to custom fit the patient.
- 5) The panel should be allowed to cool and then reattached to the brace (Step 2 above)
- 6) The Posterior Panel is often very helpful in an obese pregnant patient.

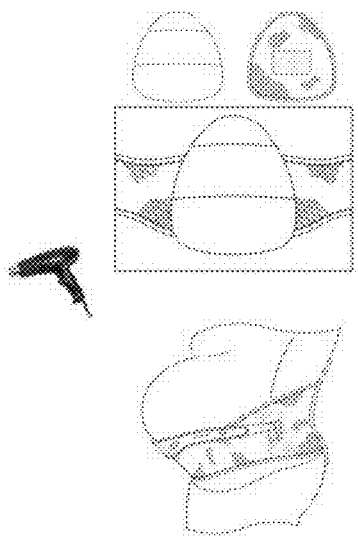

| ITEM NO. | PART NAME | MATERIAL | QTY. |
|---|---|---|---|
| 101 | MESH PADDING | COTTON MESH | 1 |
| 102 | BRUSHED NYLON | BRUSHED NYLON | 2 |
| 103 | SLIT BONING | HDPE | 2 |
| 104 | CENTER PIECE | COTTON | 1 |
| 105 | NEOPRENE ARM | NEOPRENE | 4 |
| 106 | BRUSHED NYLON FOR ARM | BRUSHED NYLON | 2 |
| 107 | ARM VELCRO | VELCRO | 2 |
| 108 | ELASTIC | STRETCH ELASTIC | 2 |
| 109 | WING BONING | HDPE | 2 |
| 110 | VELCRO | VELCRO | 1 |
| 111 | CORSET ASSEMBLY | N/A | 1 |

RIGHT AND LEFT PIECES THAT ARE MIRRORED.

RIGHT AND LEFT PIECES THAT ARE MIRRORED.

FIG. 91

Maximum Newton of Lift Produced by Different Babybrace® Configurations
(NOTE: Newtons are not the number that will be used. This is an example only of how the brace fitters can use this information to better use the brace maximizing its effectiveness.)

| FORCE OF ANTERIOR LIFT in Newtons | Babybrace™ (No Panels, Adjustment Arm (AA) Mid-High position) | Babybrace™ (No Panels, AA: Low Position) | Babybrace™ (Posterior Panels, AA: All Position) | Babybrace™ (Posterior & Anterior Panels, AA: All Positions) |
|---|---|---|---|---|
| 220 Newtons | | | | AA @High Tension |
| 200 Newtons | | | | AA @Medium Tension |
| 155 Newtons | | AA @High Tension | AA @High Tension | AA @Light Tension |
| 125 Newtons | | AA @Medium Tension | AA @Light Tension | AA @No tension |
| 100 Newtons | AA @High Tension | AA @Light Tension | | |
| 50 Newtons | AA @Medium Tension | | | |

FIG. 92

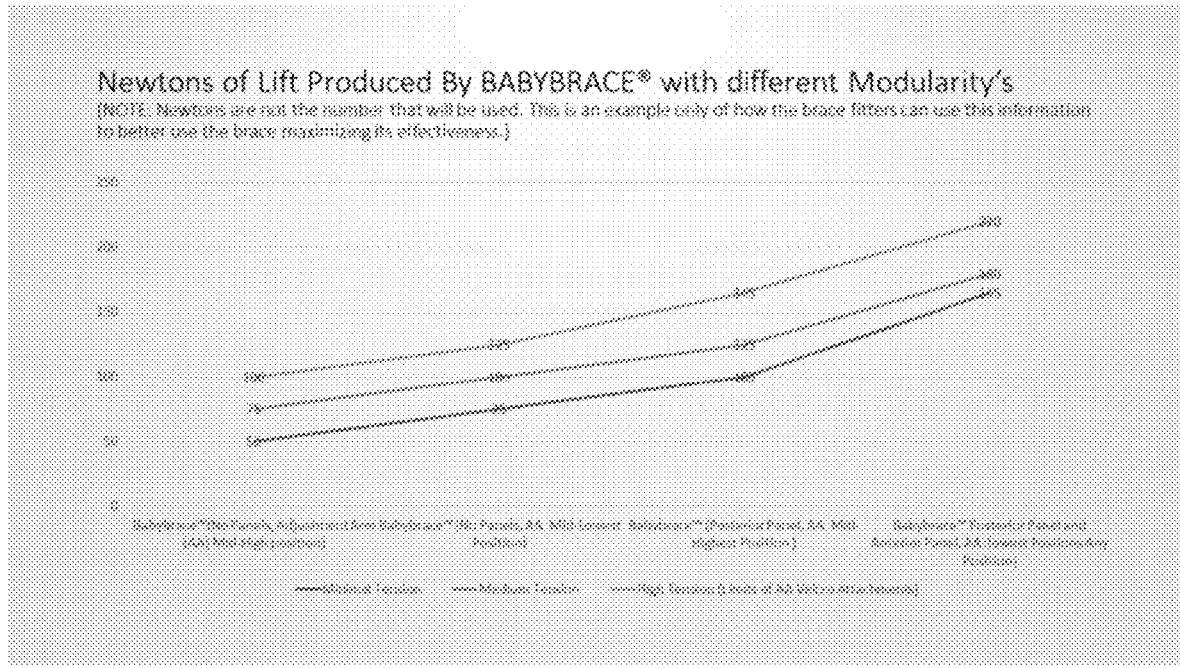

METHODS AND DEVICES FOR REDUCING PREGNANCY-RELATED AND POST-NATAL LOWER BACK PAIN

RELATED APPLICATIONS

This application is a continuation-in-part of U.S. application Ser. No. 14/993,241, filed on Jan. 12, 2016, which claims priority to U.S. Provisional Application No. 62/102,568 filed on Jan. 12, 2015. This application also claims the benefit of U.S. Provisional Application No. 62/610,925 filed on Dec. 27, 2017. Each of these applications is hereby incorporated by reference herein in their entireties.

TECHNICAL FIELD

Present embodiments relate generally to methods and systems for reducing, treating and/or preventing back pain in a person, due to for example pregnancy or post-natal changes to a person's center of gravity, or due to non-pregnancy belly weight, and/or reduced core strength in the person. These methods may employ modular maternity braces (also referred to herein as lumbar support devices). The present methods relate to the use of devices described herein, as well as to the braces/devices described e.g., in U.S. application Ser. No. 14/993,241 filed on Jan. 12, 2016 and U.S. Provisional application No. 62/102,568 filed on Jan. 12, 2015, and U.S. Provisional Application No. 62/610,925. Further provided are the modular maternity braces (lumbar support devices) described herein, including smart lumbar support devices, and kits including such modular maternity braces/lumbar support devices.

BACKGROUND

Back pain is a common complaint during pregnancy. Typically, a woman's body will gain between 15-40 pounds including the baby, larger uterus, larger placenta, amniotic fluid, and increased volume of adipose stores. This additional weight can cause physiological stress to joints, ligaments, and muscles. Ultimately this results in what is defined as pregnancy-related low back pain ((PLBP) Pregnancy Related Back Pain (PRBP)), or the onset pain in the lumbar region diagnosed during pregnancy. (See Pool-Goudzwaard A, Sliekerten Hove M, Vierhout M, Mulder P, Pool J, Snijders C, Stoeckart R. Relations between pregnancy-related low back pain, pelvic floor activity and pelvic floor dysfunction. International Urogynecology Journal. 2005;16: 468-474.)

Approximately 50-72% of pregnant women experience some kind of low back or pelvic pain during their pregnancy (See Pool-Goudzwaard A, et al.; and Ostgaard HC, Zetherstrom G, Roos-Hansson E, Svanberg B. Reduction of back and posterior pelvic pain in pregnancy. Spine. 1994; 19.8: 894-900). Out of the many symptoms of pregnancy, back pain accounts for most of the sick leave in pregnant women (See Essed G. Long-term effectiveness and costs of a brief self-management intervention in women with pregnancy-related low back pain after delivery. BMC Pregnancy and Childbirth 2008; 8:19).

Typical treatments for back pain include administration of anti-inflammatories and other medications/treatments, however such medications must be avoided during pregnancy to avoid any harmful effect to the baby. Non-pregnant persons with back pain may also not be able to, or may not choose to, use anti-inflammatories and/or other medications or available treatments.

One out of ten women also experience PLBP up to two years post-partum, which continues to impact the individual, family, and society (See Torstensson T, Lindgren A, Kristiansson P. Corticosteroid Injection Treatment to the Ischiadic Spine Reduced Pain in Women With Long-Lasting Sacral Low Back Pain With Onset During Pregnancy: A Randomized, Double Blind, Controlled Trial. Spine. 2009; 31.21: 2254-2258). PLBP can also lead to a variety of other complications such as sacroiliac joint dysfunction, posterior pelvic pain, pelvic girdle relaxation, pregnancy-related pelvic girdle pain, and pelvic dysfunction.

Another result of pregnancy and giving birth is that incisions (such as in the case of a C-section) or stretching of lower abdominal muscles (in a vaginal delivery), cause weakened core muscles, which also lead to back pain post-partum.

There is a need for methods and devices to safely reduce, treat and/or prevent back pain in an individual.

SUMMARY

Provided herein are methods and systems for reducing, treating and/or preventing pregnancy-related and/or post-natal lower back pain in an individual. Such methods may include shifting the center of gravity of a person, for example by applying modifiable lifting forces to a lower abdomen of the individual using a poly system, under the belly of the individual toward the desired center of gravity and applying one or more vector forces from an anterior side of the individual toward the desired center of gravity. Methods herein may include applying a lumbar support device (such as a device provided herein) to the individual's back and securing wings of the device around the person's belly, and securing fastening wings to one another.

Also provided herein are brace(s)/device(s) for reducing, treating and/or preventing pregnancy-related and/or post-natal lower back pain.

According to non-limiting example embodiments, the brace(s)/device(s) are adjustable, modular, lumbar support devices that may be used to provide lumbar support. The present methods and support devices are effective at decreasing the stresses on the spine, and improving posture/alignment during activities of daily living.

According to non-limiting example embodiments, support or brace devices provided herein may be used as a maternity brace throughout a woman's pregnancy (even as the woman's anatomy changes throughout the pregnancy). When used as a maternity brace, the present devices may be used both during pregnancy for gestational support and/or post-partum (post-natal support), because they are adjustable and modular and have safety mechanisms therein to prevent over-tensioning. The present devices may also be used as lumbar support braces for persons who have excess belly weight or persons with ascites, etc.

The brace may be modular at least in that it incorporates removable padded, but rigid, anterior and posterior panels.

Also provided are kits that include at least one of the braces/devices provided herein. The present kits may optionally include instructions for proper application, positioning, and/or adjustment of the lumbar support device. Kits may also include e.g., one or more shoulder attachments, removable panels, e.g. for post-partum or other non-pregnancy uses, dial addition, electronic component, and/or an extender or other accessory described herein. The removable panel may include for example, a panel selected from the group consisting of an anterior panel, a posterior panel, and a coronal panel, which may be padded. The removable panels may include a panel that enables the brace to comply with at least one brace code selected from the group consisting of L0631 and L0637 US brace codes.

Further provided are systems of reducing, treating or preventing back pain in an individual during pregnancy or post-partum, that include at least one lumbar support device, which includes electronic component incorporated therein or therein. The electronic component may include for example, electronics that are capable of detecting and/or monitoring one or more maternal and/or fetal vital signs. The electronics may optionally have a method of recording, displaying, and/or communicating such vital signs (or data), for example to a computer or smart device, such as the cell phone or computer of a wearer of the device or person authorized by them (e.g., spouse or other family member, physician, etc).

This application outlines and describes the features and technical advantages of the present invention so that the detailed description of the invention that follows may be better understood. Additional features and advantages of the invention will be described herein. It should be appreciated by those skilled in the art that any conception and specific embodiment disclosed herein may be readily utilized as a basis for modifying or designing other structures for carrying out the purposes of the present invention. It should also be realized by those skilled in the art that such equivalent constructions and/or methods do not depart from the spirit and scope of the invention as set forth herein. The novel features which are believed to be characteristic of the invention, both as to its organization and method of operation, together with further objects and advantages will be better understood from the following description when considered in connection with the accompanying figures. It is to be expressly understood, however, that any description, figure, example, etc. herein is provided for the purpose of illustration and description only and is by no means intended to define the limits the invention.

BRIEF DESCRIPTION OF THE DRAWINGS

Non-limiting example embodiments described herein, with reference to the following accompanying Figures.

FIGS. 1A and 1B depict front/anterior perspective views of an example lumbar support device 20 provided herein. FIG. 1C is a front/anterior view of the lumbar support device 20. FIG. 1D is a side view of the lumbar support device of FIGS. 1A-1C. FIG. 1E is a top view of the lumbar support device of FIGS. 1A-1C. FIG. 1F depicts a perspective view of the example lumbar device.

FIGS. 3A, 3B, and 3C depict a layer 1 of fabric from posterior view (FIG. 3A) of the lumbar support device of FIGS. 1A-2. FIG. 3B depicts a side view of layer 1. FIG. 3C depicts a perspective view of the example layer 1.

FIGS. 4A, 4B, and 4C depict a second layer (from the exploded view of FIG. 2) of the lumbar device of FIGS. 1A-2. In particular, FIG. 4A depicts a padding layer 2. FIG. 4B depicts a cross section of the padding layer 2. FIG. 4C depicts a perspective view of the example padding 2.

FIG. 5C depicts a perspective view of the example wing 4.

FIGS. 6A, 6B, and 6C depict a wing 4 of FIG. 5A with multiple ribs 5 thereon from both a front and a side view (FIGS. 6A and 6B respectively). The wing 4 is depicted with ribs 5 prior to adding another wing 4 thereon. FIG. 6C depicts a perspective view of the example wing ribs 5.

FIGS. 7A, 7B, 7C and 7D depict an example corset pulley system assembly according to non-limiting embodiments of the lumbar device of FIGS. 1A-2. In particular, FIG. 7A depicts an example of the corset pulley system assembly which will be enclosed within the material of the brace (from a front view), FIG. 7B from a top view, and FIG. 7C from a right side view. FIG. 7D depicts a perspective view of the example corset sub-assembly 6.

FIGS. 10A and 10B depict a front and a side view of a corset fabric 24 of a corset assembly according to inter alia, FIG. 8A. FIG. 10C depicts a perspective view of the example corset fabric 24.

FIGS. 11A and 11B depict a front and a side view of one of the one of multiple diagonal corset fabric portions of a corset assembly according to inter alia, FIG. 8A. FIG. 11C depicts a perspective view of the example corset fabric 22.

FIGS. 13A and 13B depict the corset assembly, and in particular, the stitching of fabrics together along the hatched area. FIG. 13C depicts a perspective view of the example left side assembly of the corset fabric construction.

FIGS. 15A, 15B, and 15C depict a front, top and side view, respectively of a clip of a corset assembly according to inter alia, FIG. 8A. FIG. 15D depicts a perspective view of the example clip 21.

FIG. 16A depicts an exploded front perspective view of a wing assembly according to non-limiting embodiments of the lumbar device of FIGS. 1A and 2. FIG. 16B depicts a perspective view of the example wing assembly. It should be noted that none of the colors indicated herein are meant to be limiting or binding and further example embodiments include other colors.

FIGS. 17A and 17B depict a front view and view from the side respectively, of one of the wings 8 from e.g. FIG. 16A. FIG. 17C depicts a perspective view of the example wing.

FIGS. 21A, 21B and 21C depict wing fastener portions 3 (e.g. hook and loop fastener, such as VELCRO® which may attach one wing to the other wing to secure the wings around the belly in a desired location. FIG. 21D depicts a perspective view of the example wing hook and loop fastener.

FIGS. 22A, 22B and 22C depict front, top and side views of arms 17 from the device of FIGS. 1A-2. FIG. 22D depicts a perspective view of the example arm template.

FIGS. 23A, 23B and 23C depict front, top and side view of an elastic arm strap 16, which is a component of each arm, as shown in FIG. 20. FIG. 23D depicts a perspective view of the example arm strap.

FIG. 24A details embodiments of how to assemble the arm when fabricating the brace, i.e., that it is necessary to pull the arm through the blue square slit hole prior to sewing it, because once it is sewed in, it will be impossible to get the arm through.

The complex relationship between the adjustment arms, their elastic material, their position, shape, the fact that they exiting through the main arms (via slit), and the elastic pulley system are all distinct features of the present invention. This complex relationship allows the brace to conform to multiple patient's body habitus is well at the same time having protective mechanisms to avoid excessive increased hydraulic pressure is within the abdominal cavity. (unwanted in pregnancy) The anterior panel can be placed between the adjustment arms and main panel to provide additional support but not excessive pressure. The anterior panel may be configured to be adjusted with hook and loop fasteners to allow positioning by a user in a desired area for comfort.

Figure 20:
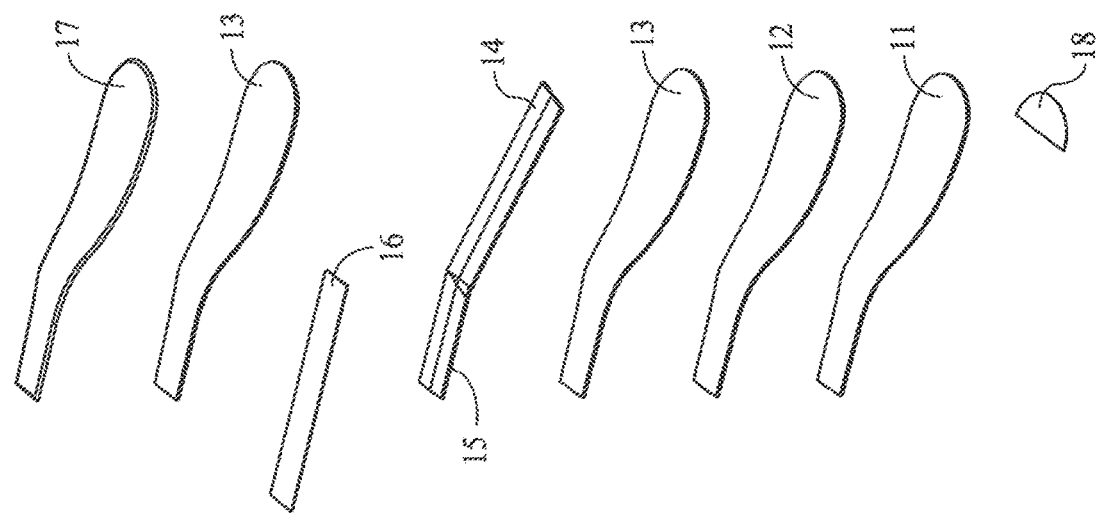
FIG. 20 depicts an exploded view of an example embodiment of one or two arms having layers 11-17 and an attachment 18 to enable attachment of the arm to a second arm in accordance with the device of FIGS. 1A and 2 et seq.

FIGS. 25A, 25B and 25C depict front, top and side views of an arm bone component of the arms according to non-limiting example embodiments of the present invention as shown in FIG. 20. FIG. 25D depicts a perspective view of the example arm bone 14.

Figure 26A:
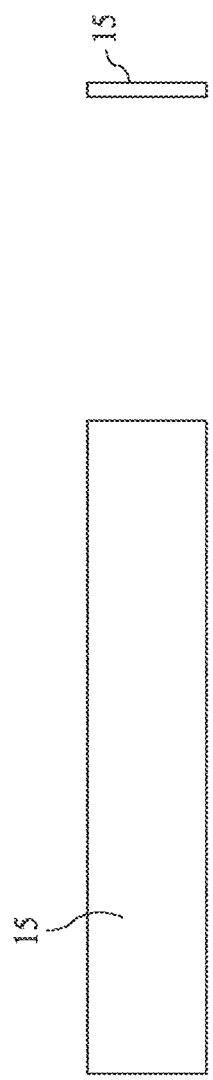
Figure 26C:
Figure 26B:
Figure 26D:

FIGS. 26A, 26B and 26C depict front, top and side views of a second arm bone of the arms of the present invention. FIG. 26D depicts a perspective view of the example arm bone 15.

Figure 27A:
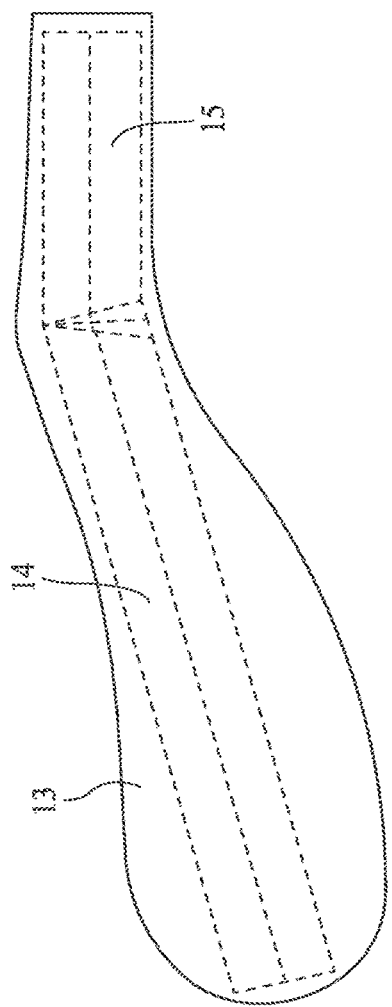
Figure 27B:
Figure 27C:
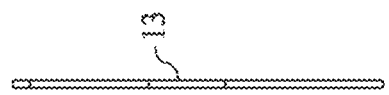
Figure 27D:

FIGS. 27A, 27B, and 27C depict front, top and side views of mesh arm 13, with relative placement of arm bones 14 and 15 shown. FIG. 27D depicts a perspective view of the example arm bone placement in the mesh arm.

FIGS. 28A, 28B and 28C depict arm fastener portions 18 (e.g. hook and loop fastener, such as VELCRO®.) which may attach one arm to the other arm to secure the arms around the belly. FIG. 28D depicts a perspective view of the example arm hook and loop fastener.

FIGS. 29-34 depict, removable padded, but rigid, anterior and posterior panels, which may be added or removed from the device of FIG. 1 et seq. by the user; e.g., during post-partum or other non-pregnancy use.

Figure 29:
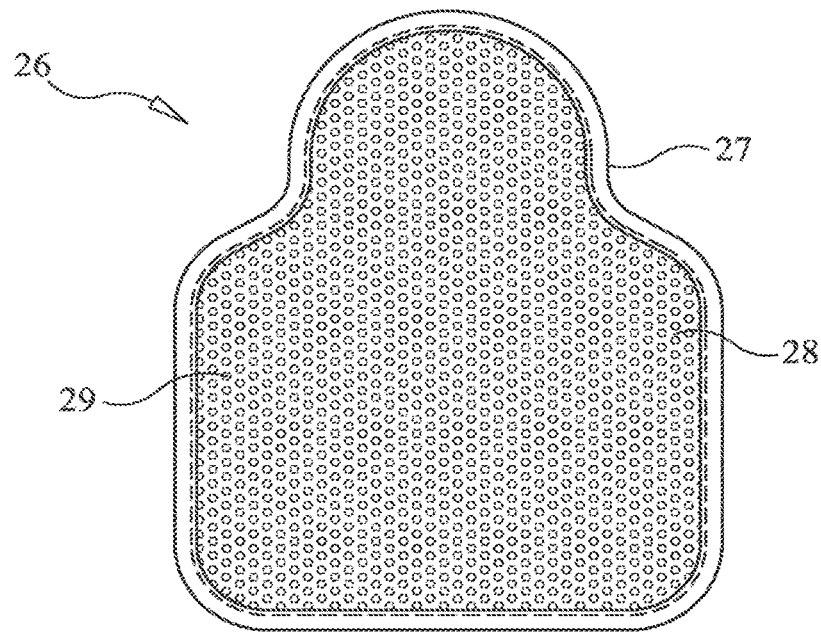

FIG. 29 depicts a front view of a removable padded, but rigid, posterior panel in accordance with non-limiting example embodiments.

Figure 30:
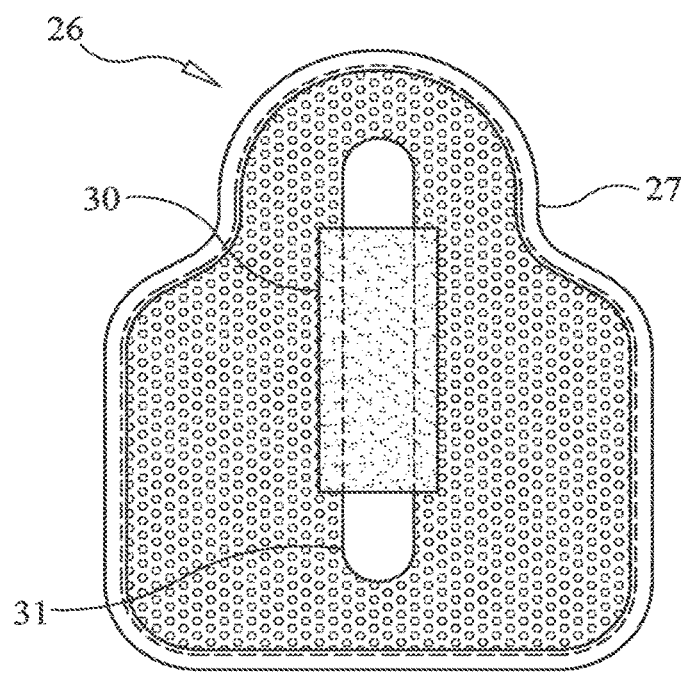

FIG. 30 depicts a back view of the removable padded posterior panel of FIG. 29.

Figure 31:
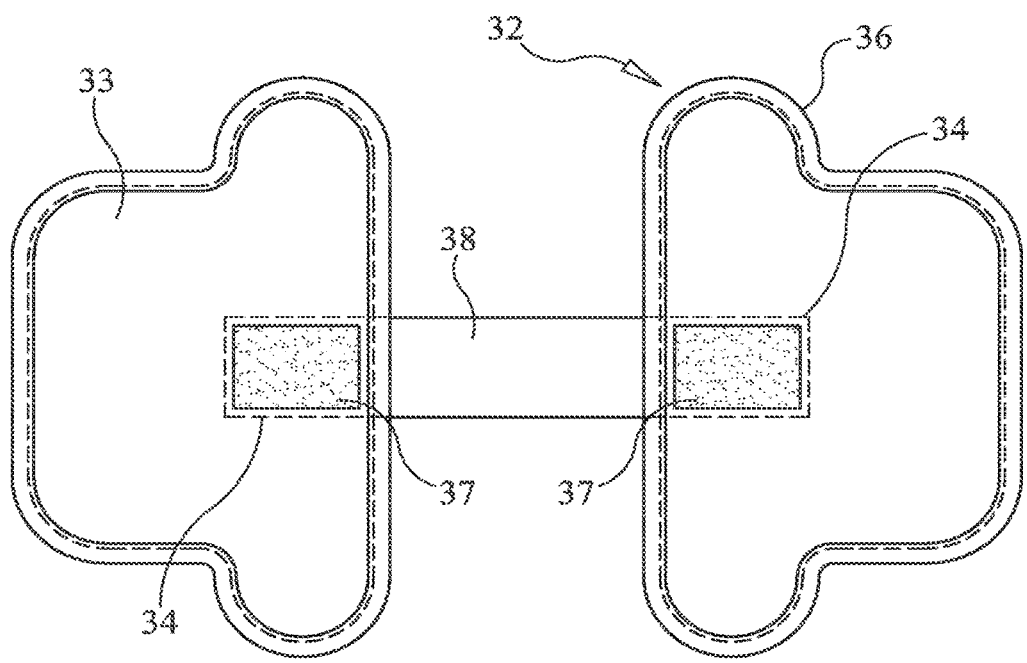

FIG. 31 depicts a front view of a removable padded, but rigid, coronal side panel in accordance with non-limiting example embodiments.

Figure 32:
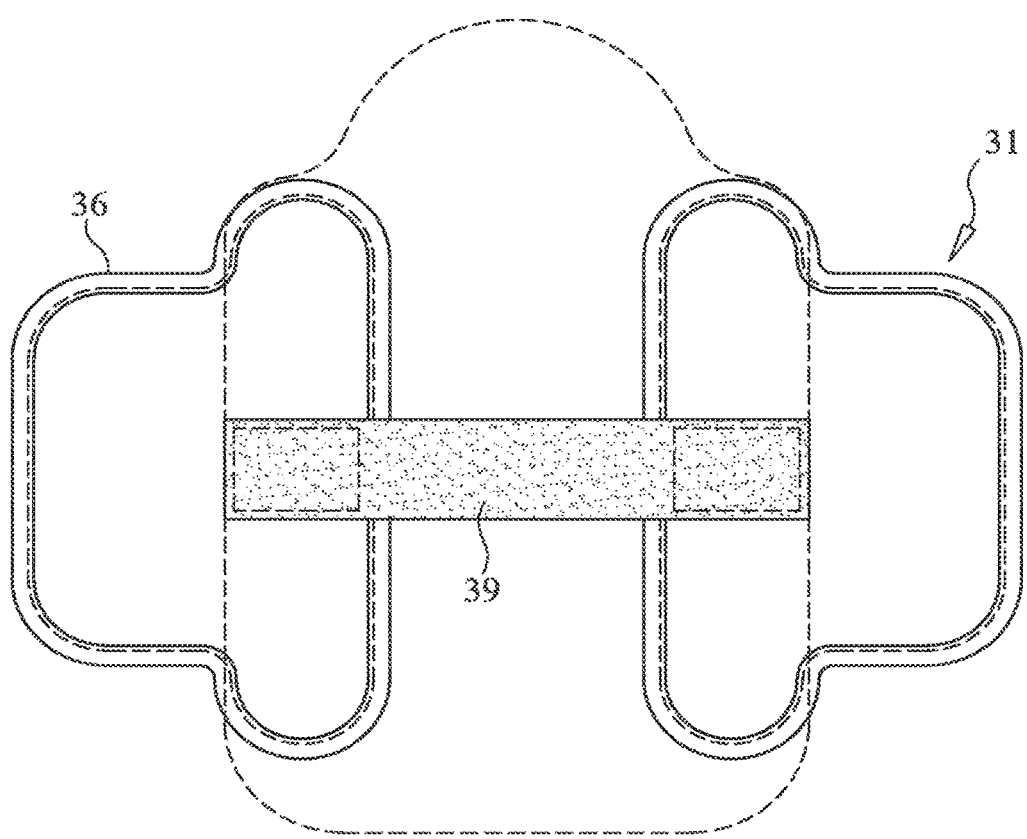

FIG. 32 depicts a back view of the removable coronal side panel of FIG. 31.

Figure 33:
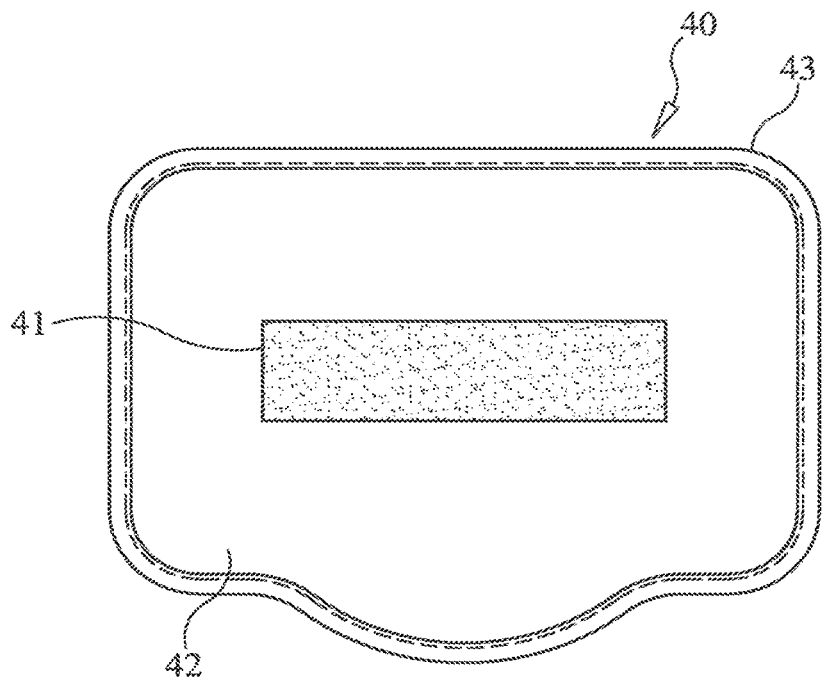

FIG. 33 depicts a front view of a removable padded, but rigid, anterior panel in accordance with non-limiting example embodiments.

Figure 34:
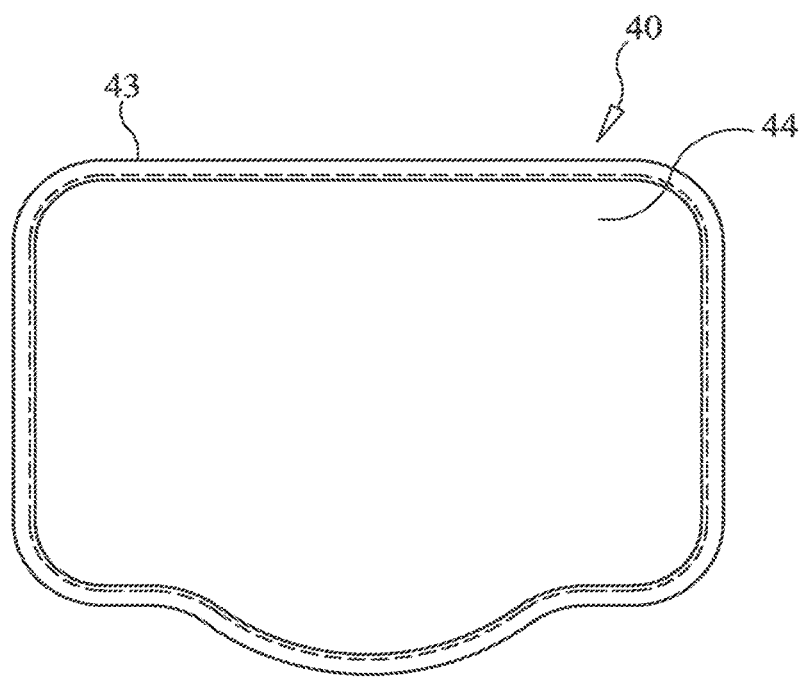

FIG. 34 depicts a back view of the removable anterior panel of FIG. 33.

FIGS. 35-40 depict example embodiments of a device of FIG. 1 et seq., and depict the device in use by various users, in accordance with non-limiting examples.

Figure 35:
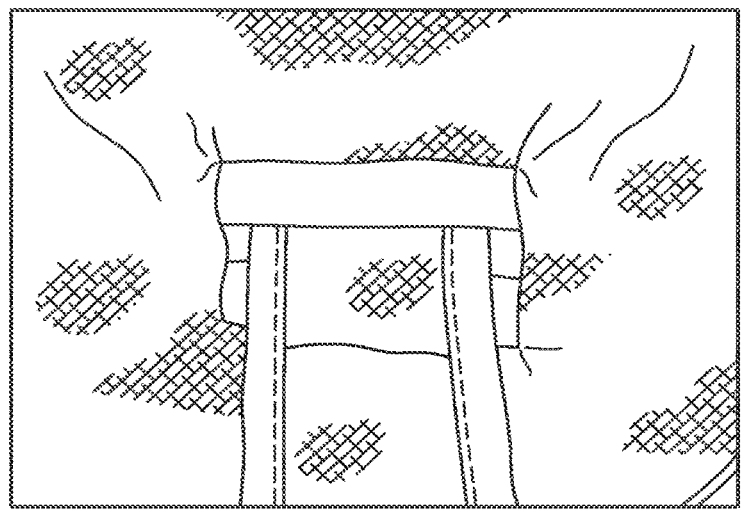

FIG. 35 depicts a close up view of a portion of a lumbar support device in accordance with non-limiting example embodiments. In particular, depicted is an arm emerging from a slit in a wing of the support device.

Figure 36:
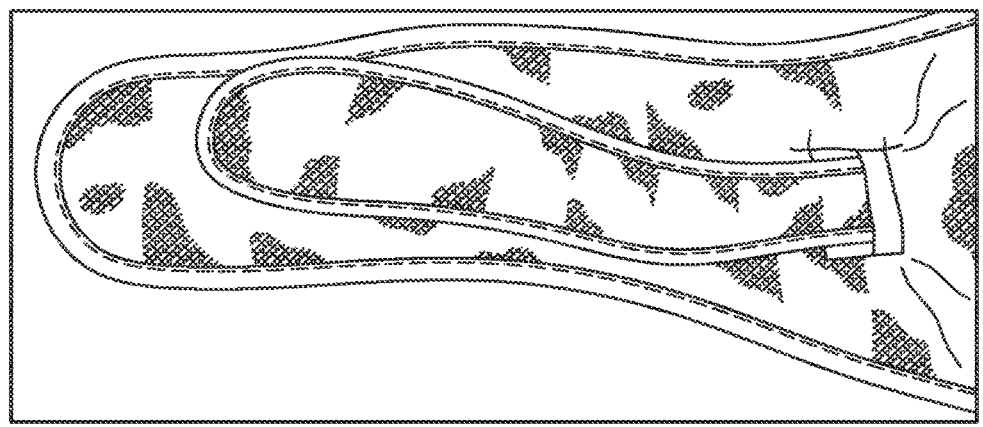

FIG. 36 depicts a drawing of one side of a lumbar support device in accordance with non-limiting example embodiments of the present invention. As shown in FIG. 36, an arm emerges from a slit in the corresponding wing.

Figure 37:
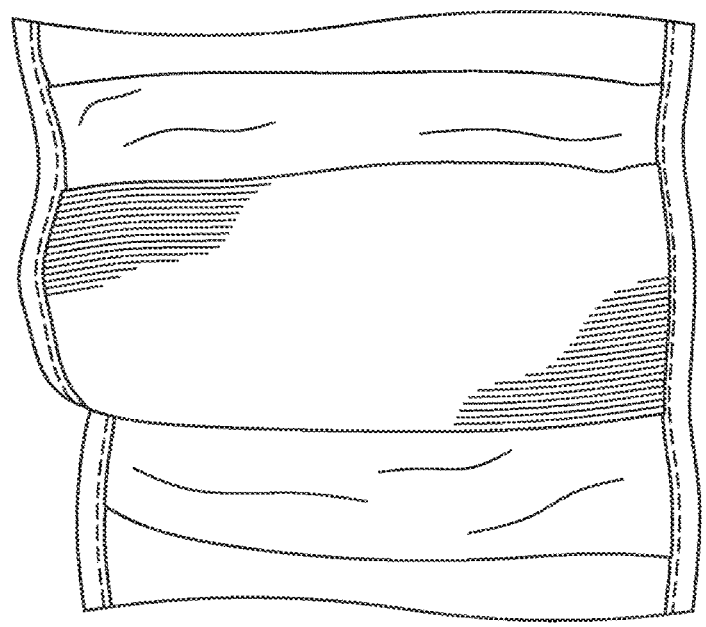

FIG. 37 depicts a drawing of a middle portion of an underside of the lumbar support device in accordance with non-limiting example embodiments.

Figure 38:
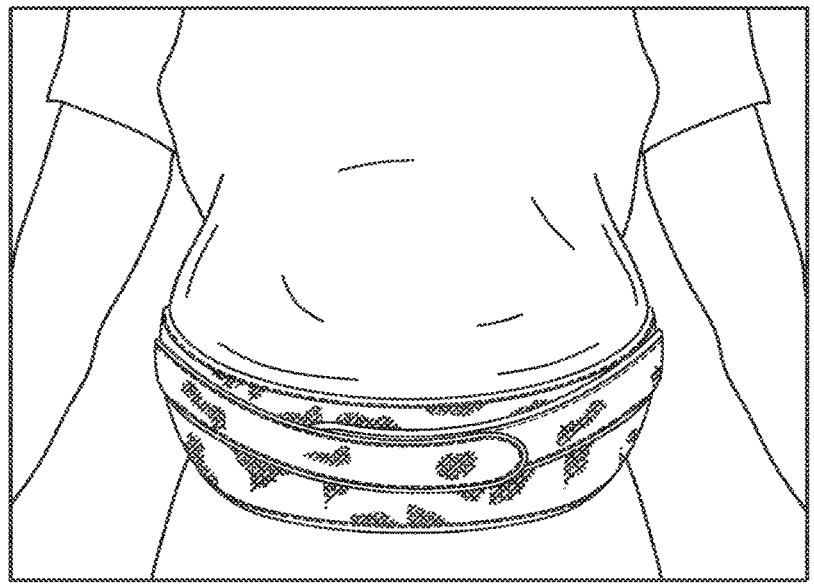

FIG. 38 depicts a device in accordance with the present invention in use as applied to a pregnant user. In the depicted embodiment, the wings are first applied over the belly and attached to one another with sing fasteners, and the arms are applied and positioned over the wings and attached to one another with arm fasteners.

Figure 39:
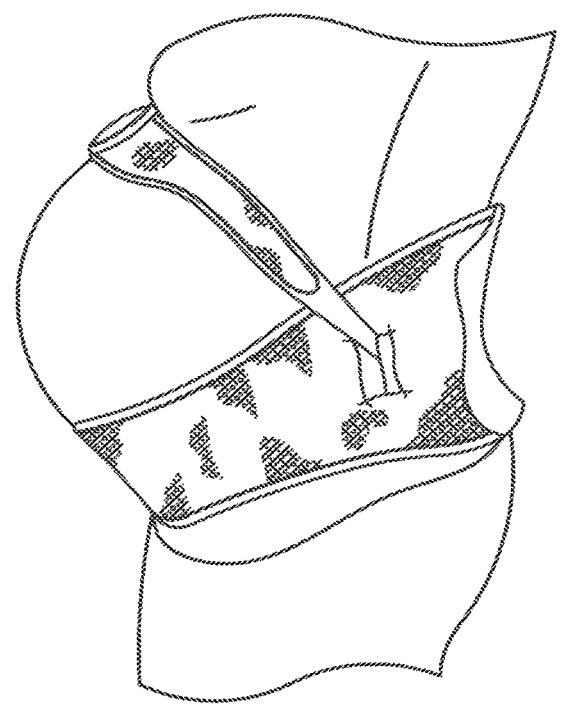

FIG. 39 depicts a device in accordance with the present invention in use as applied to a different pregnant user than in FIG. 38. In this embodiment, the wings are applied toward the bottom of the belly and attached to one another and the arms are positioned over the top of the belly and attached to each other with arm fasteners in that position.

Figure 40:
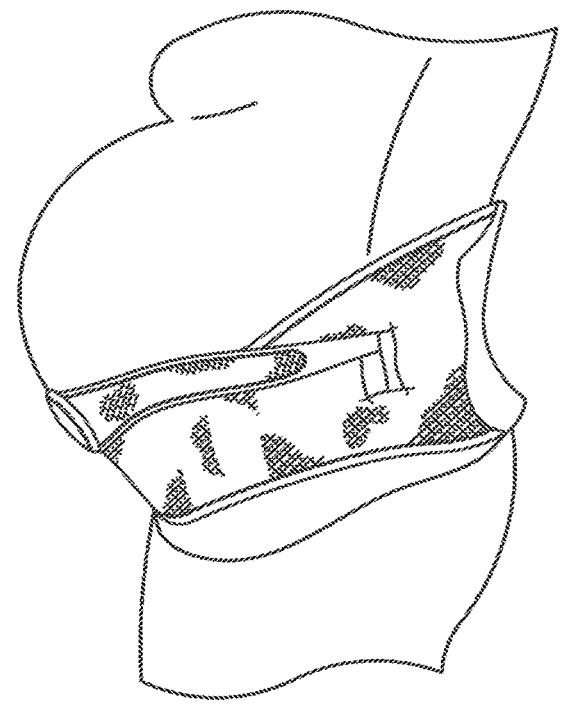

FIG. 40 depicts a device in accordance with the present invention in use as applied to a pregnant user. In the depicted embodiment, the wings are first applied over the belly and attached to one another, and the arms are applied and positioned at least somewhat over the wings and attached to one another over the wings with arm fasteners.

Figure 41:
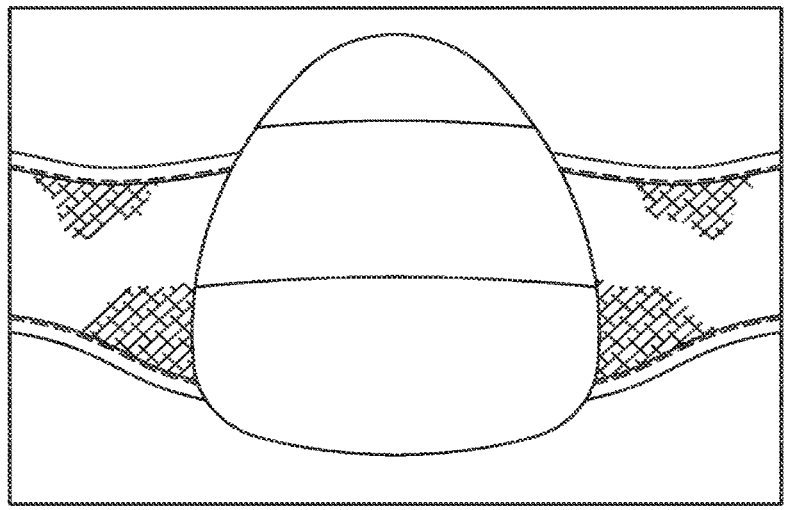

FIG. 41 depicts the front of a posterior panel in accordance with non-limiting example embodiments.

Figure 42:
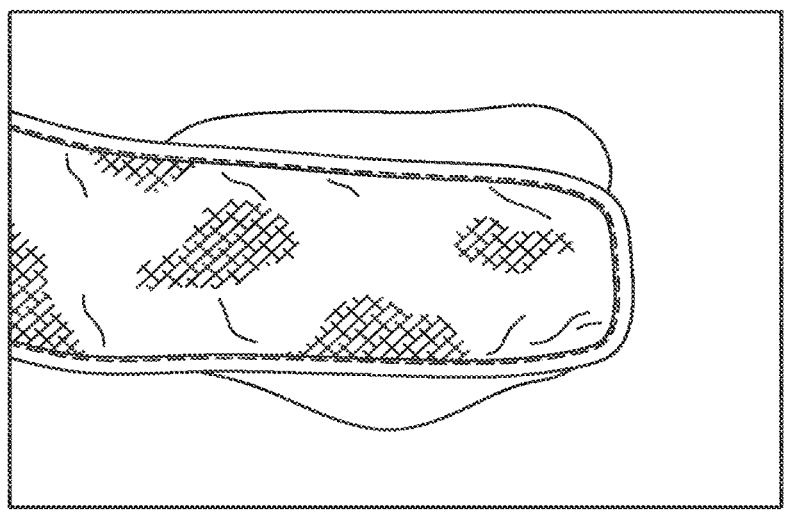

FIG. 42 depicts an anterior panel attached to an arm of the present device, in accordance with non-limiting example embodiments.

Figure 43:
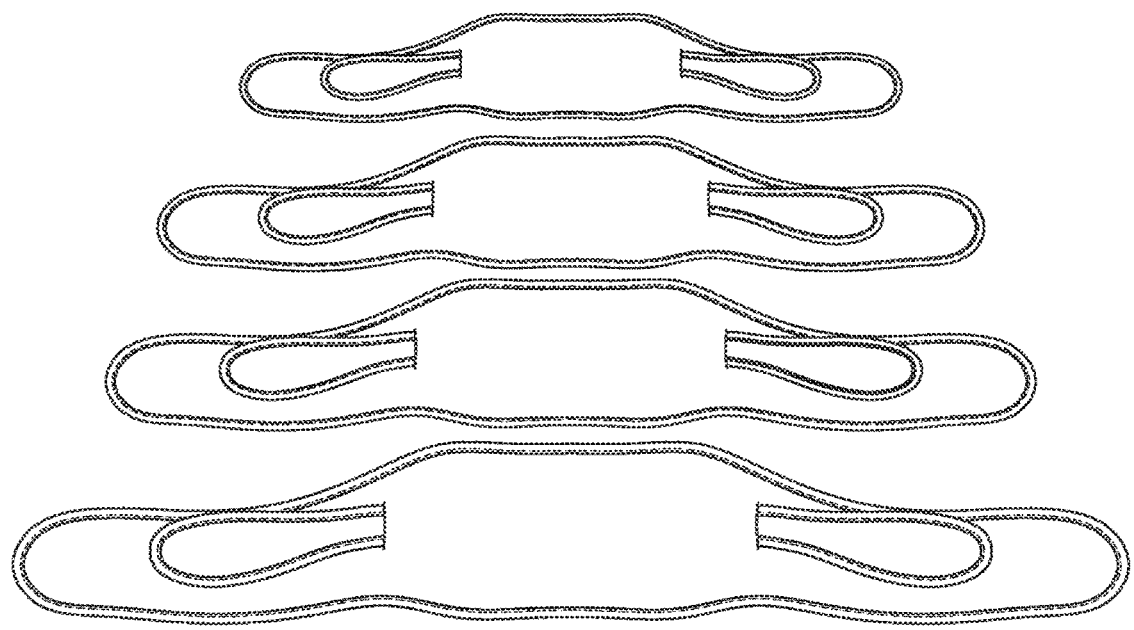

FIG. 43 depicts drawings of example lumbar support devices of the present invention, of various sizes, in accordance with non-limiting example embodiments.

Figure 44:
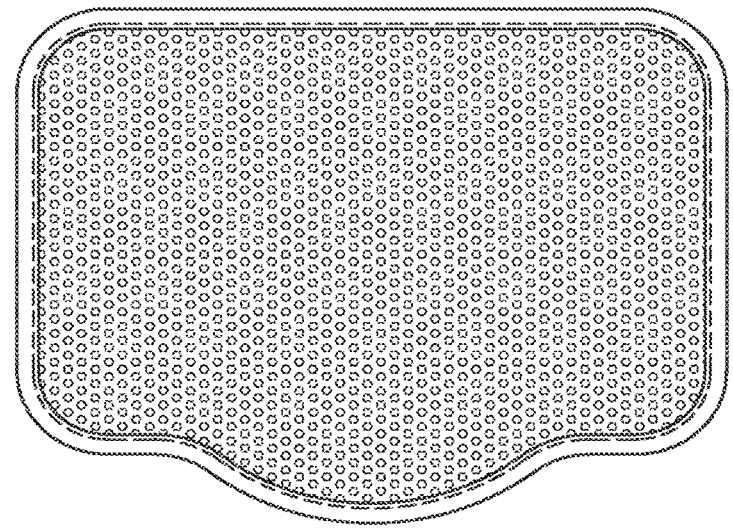

FIG. 44 depicts an anterior panel in accordance with non-limiting example embodiments.

Figure 45:
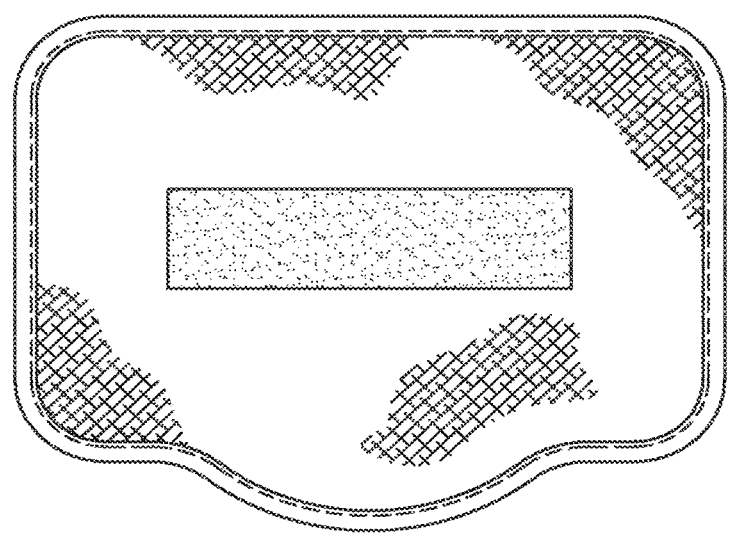

FIG. 45 depicts an opposite side of an anterior panel of FIG. 44, in accordance with non-limiting example embodiments. The rectangular portion in the middle is a portion of a hook and loop fastener. According to other example embodiments, the device may include a loop fastener or other suitable fastener.

Figure 46A:
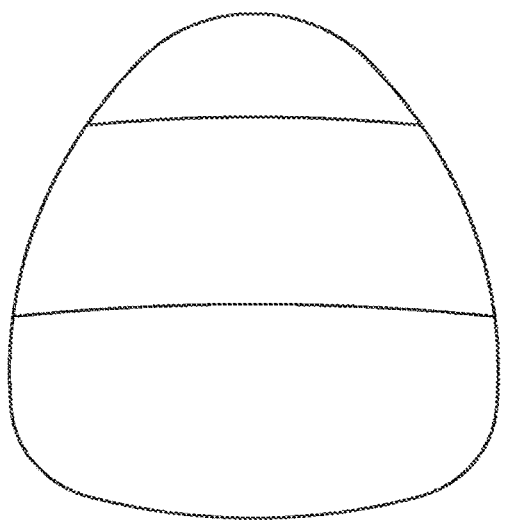
Figure 46B:
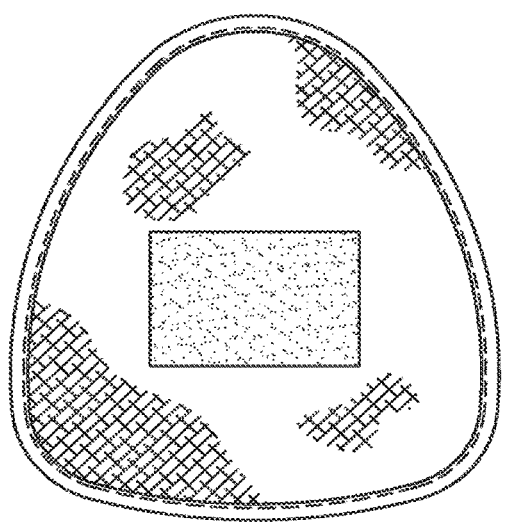

FIG. 46A and 46B depict the front and back of a posterior panel in accordance with non-limiting example embodiments of the invention.

Figure 47:
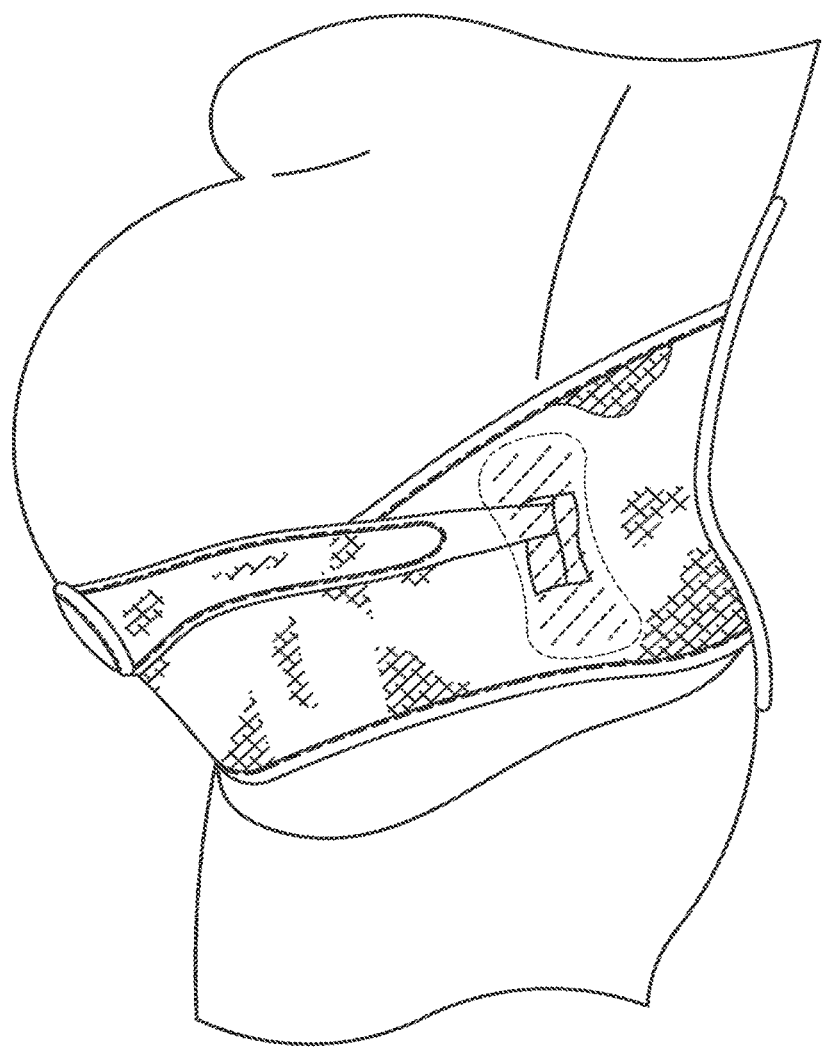

FIG. 47 depicts a non-limiting example of a support device/brace in accordance with the present invention, having one or more coronal panels. In particular, the figure depicts a support device/brace in use on an individual, which has coronal panels inserted (slid in) on both sides.

Figure 48A:
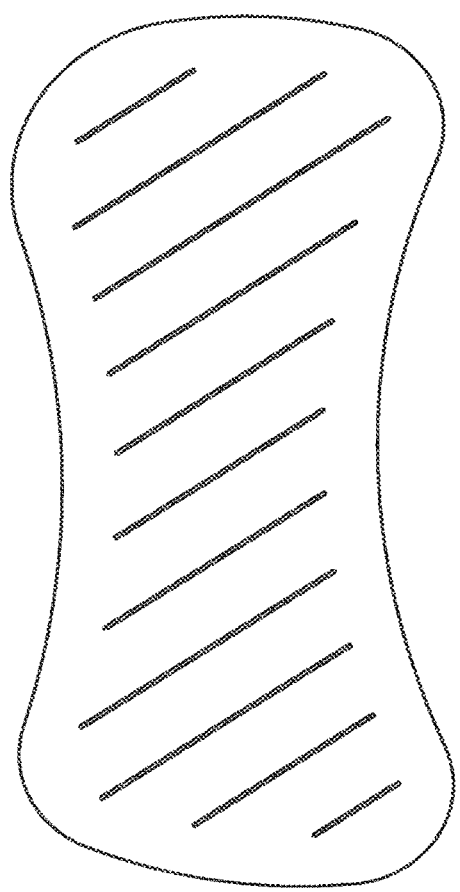
Figure 48B:
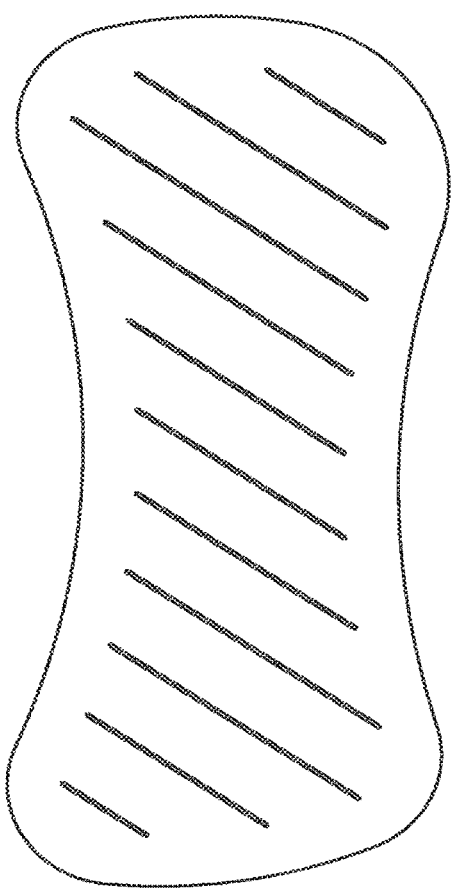

FIGS. 48A and 48B depict non-limiting examples of coronal panels that may be used in conjunction with example support devices of the present invention.

Figure 49:
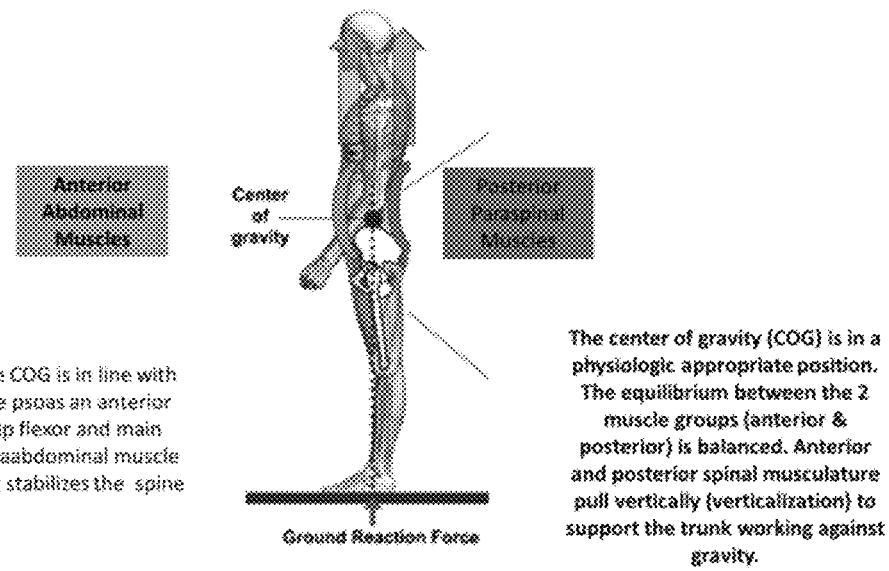

FIG. 49 depicts the center of gravity in an individual.

Figure 50:
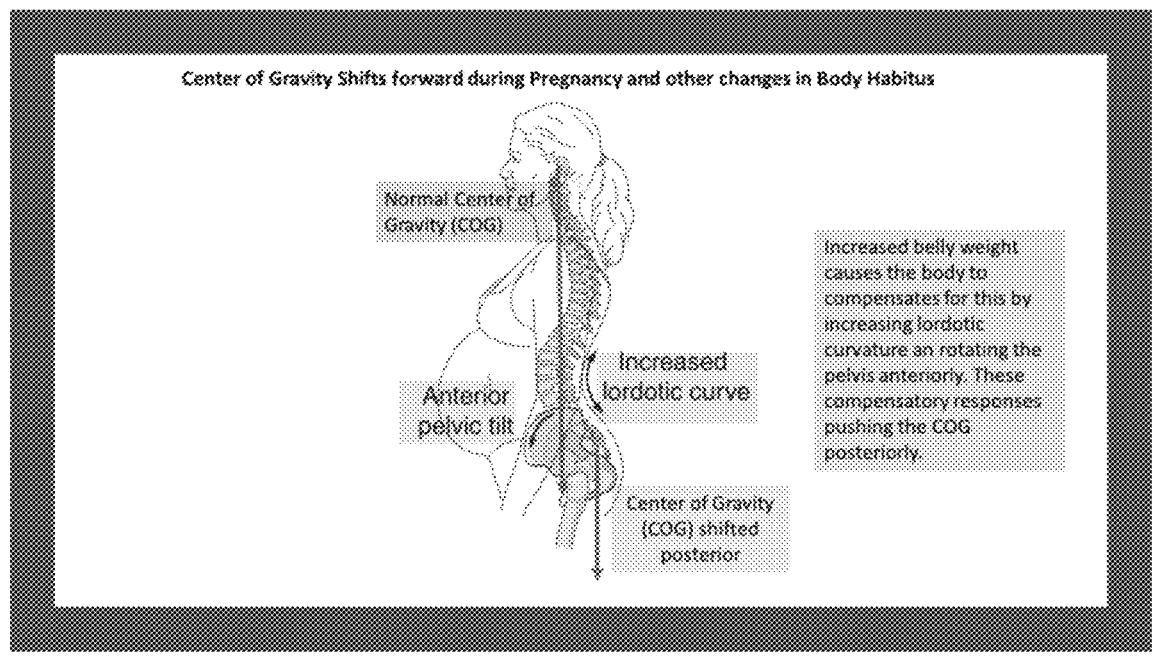

FIG. 50 depicts a center of gravity shift forward during pregnancy and other changes in body habitus.

Figure 51:
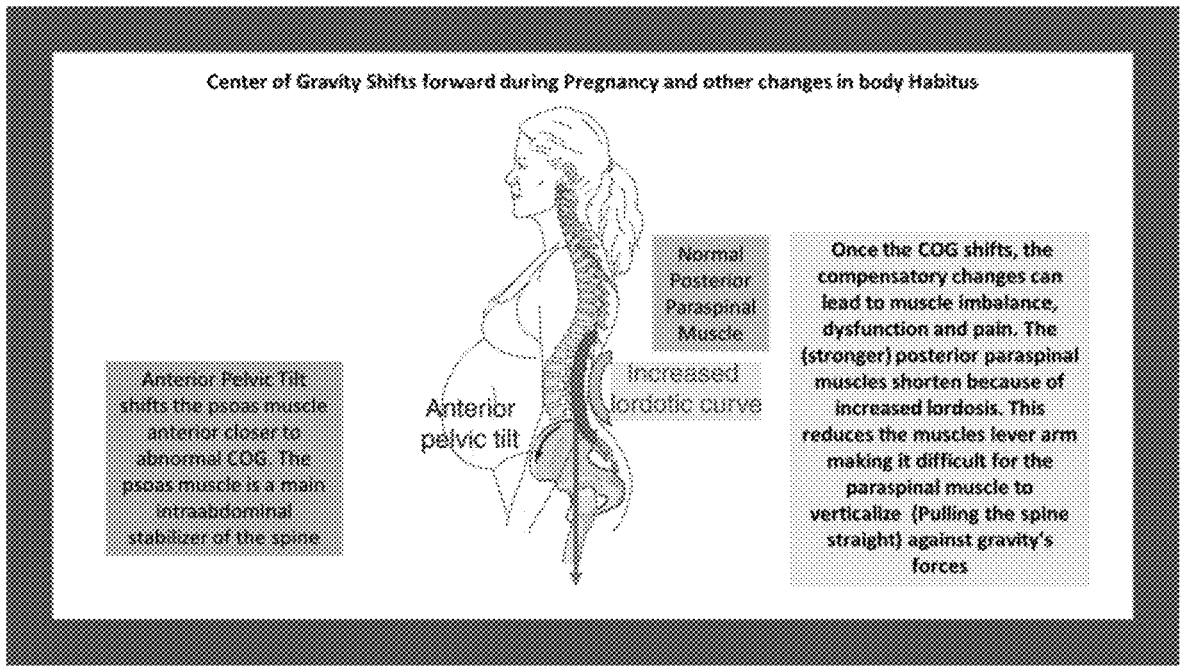

FIG. 51 depicts a center of gravity shift forward during pregnancy and other changes in body habitus.

Figure 52:
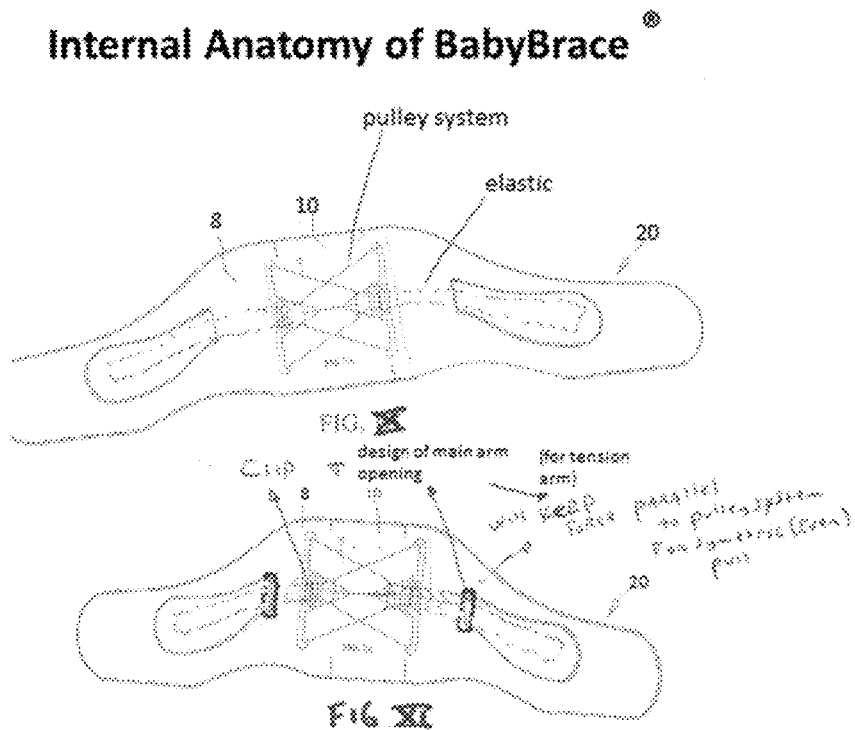

FIG. 52 depicts the internal anatomy of a device in accordance with the present invention.

Figure 53:
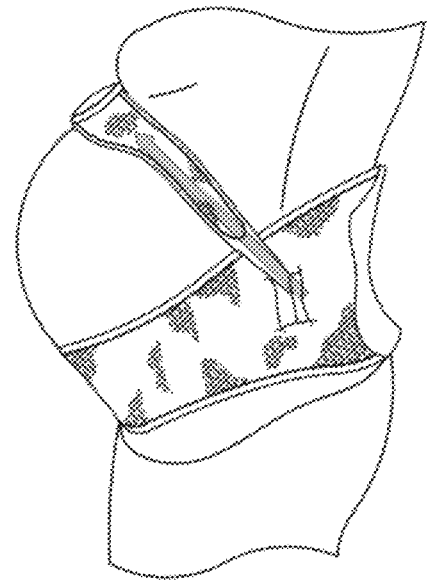

FIG. 53 depicts force vectors during the adjustment process of a device in the present invention with the straps over the belly. In particular, in FIG. 53, vertical tensioning results in less force into pulley system.

Figure 54:
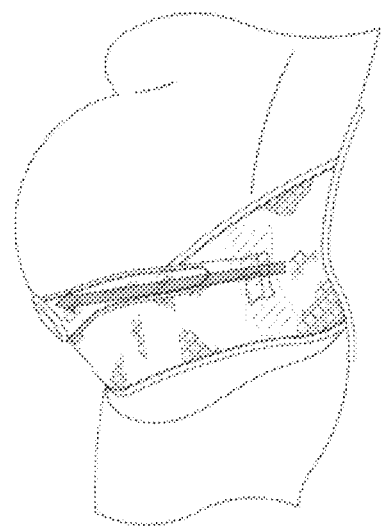

FIG. 54 depicts force vectors during the adjustment process of a device in the present invention with the straps under the belly. In particular, in FIG. 54, parallel adjustment results in more force into pulley system.

FIG. 55 depicts an internal view of force vectors during the adjustment process during use of a device in the present invention. FIG. 55 shows the corset pully of FIG. 7A in use in the present devices, and how the forces work in the pulley system.

FIG. 56 depicts a cross-section of the present devices and forces produced during use.

Figure 57:
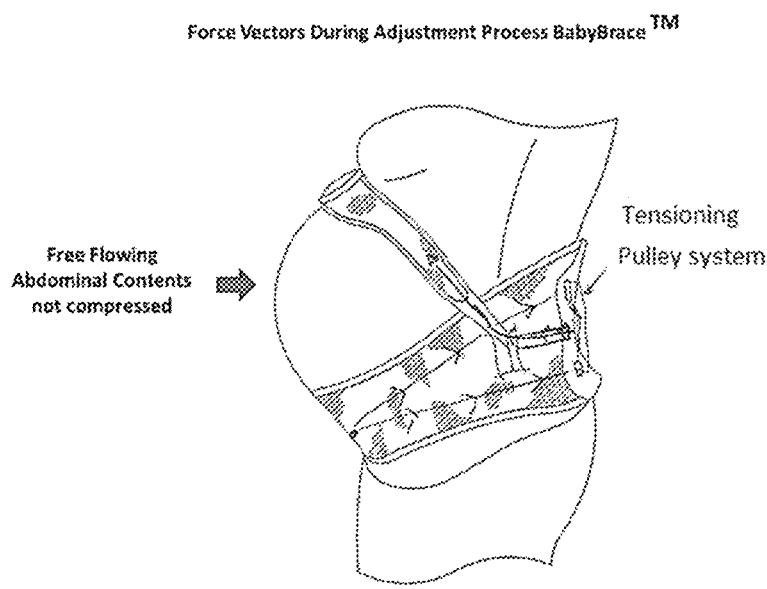

FIG. 57 depicts force vectors during the adjustment process of a device in the present invention with the straps over the belly.

Figure 58:
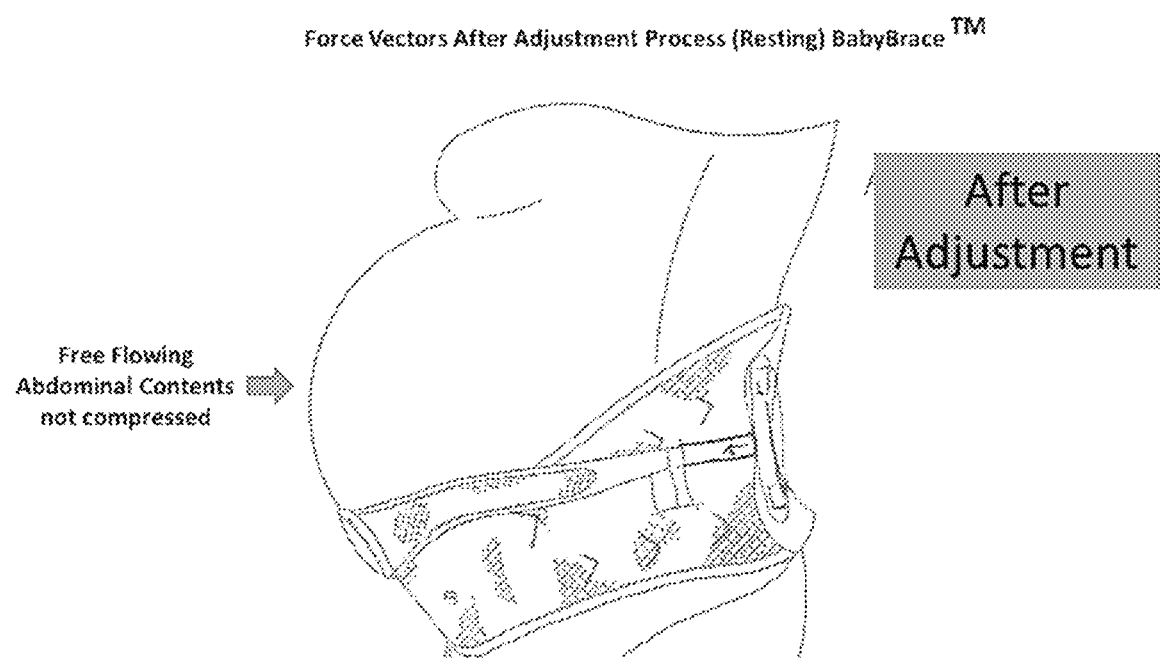

FIG. 58 depicts force vectors after adjustment of a device in the present invention.

Figure 59:
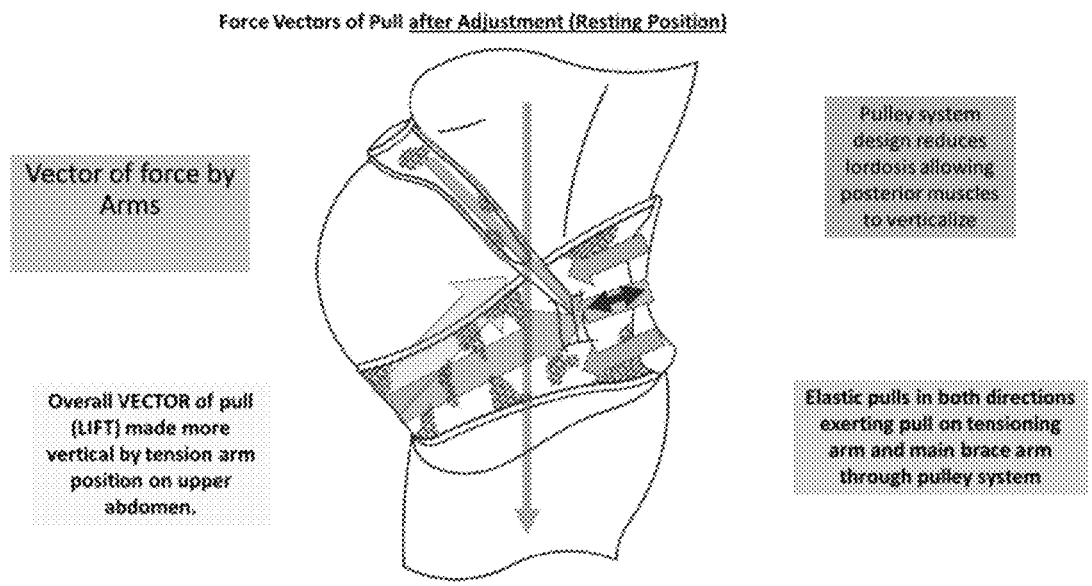

FIG. 59 depicts force vectors after the adjustment process of a device in the present invention with the straps over the belly.

Figure 60:
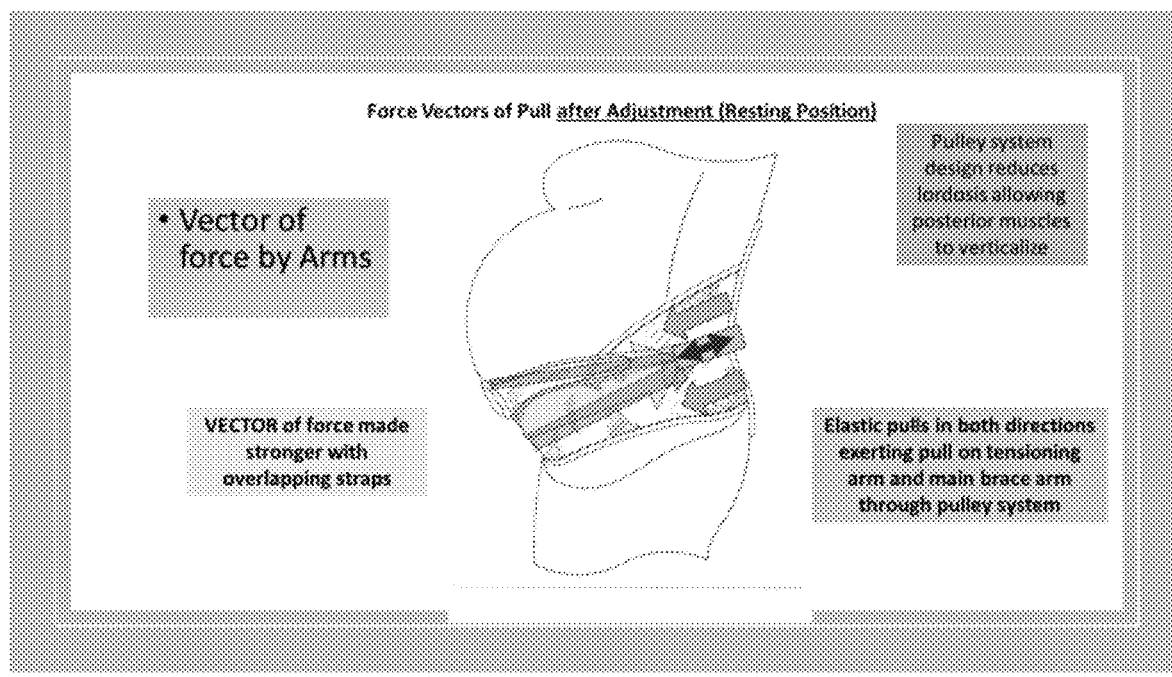

FIG. 60 depicts force vectors of pull after the adjustment of a device in the present invention, in a resting position.

Figure 61:
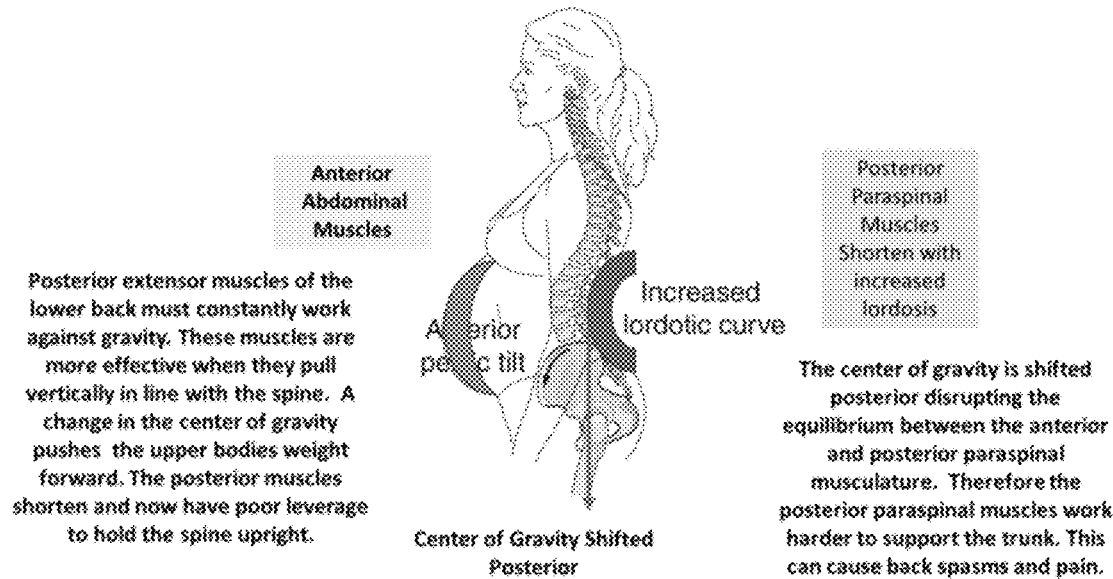

FIG. 61 depicts equilibrium disruption between anterior and posterior spinal support musculature.

Figure 62:
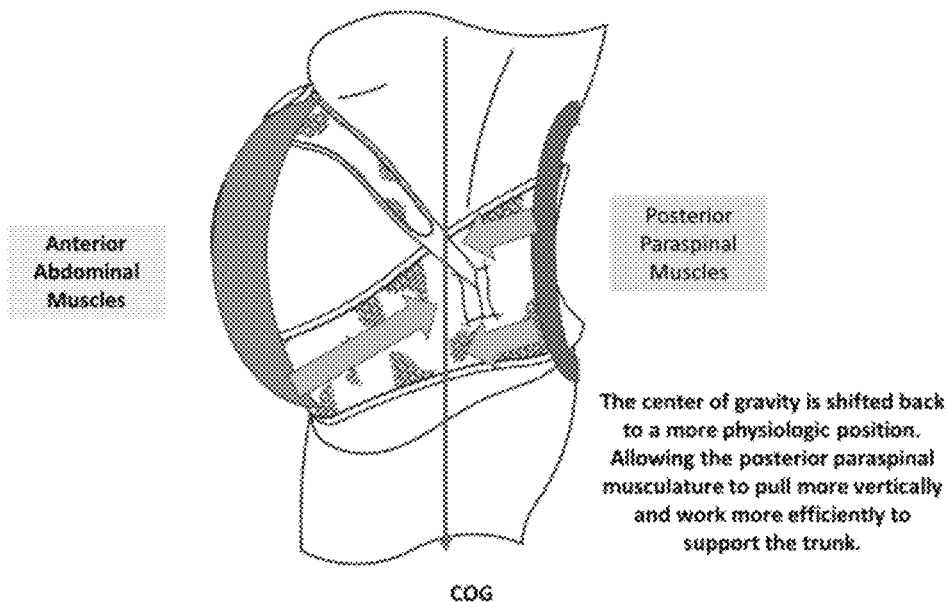

FIG. 62 depicts equilibrium restoration between anterior and posterior spinal support musculature.

Figure 63:
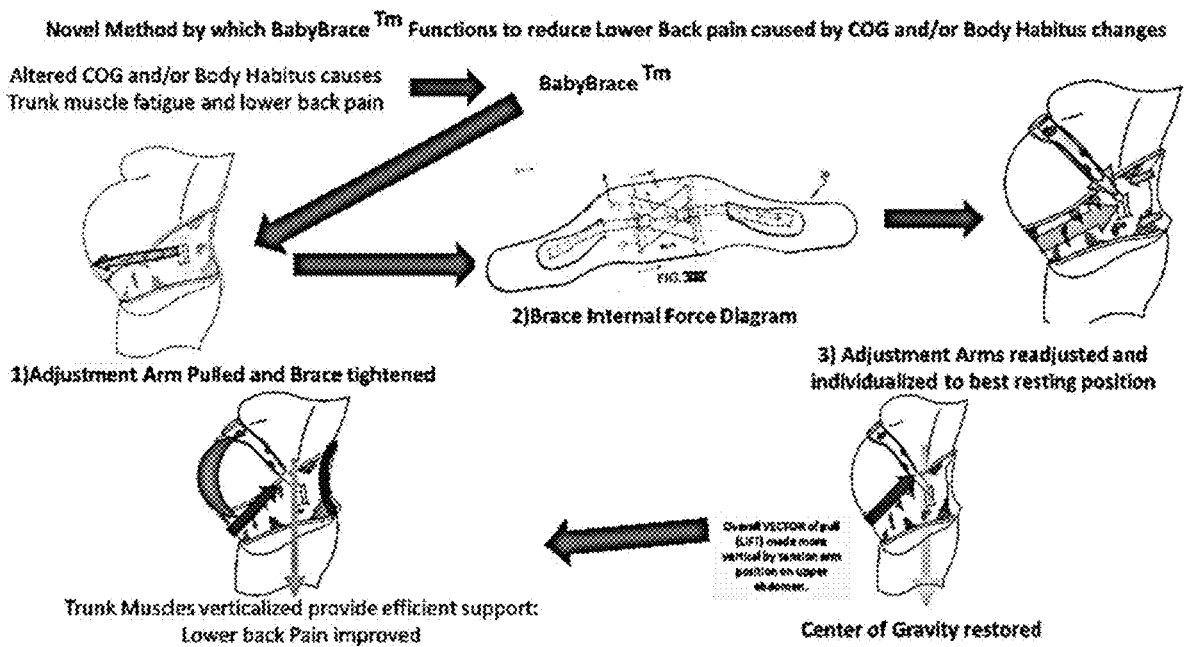

FIG. 63 depicts a method by which the present devices function to reduce lower back pain.

Figure 64:
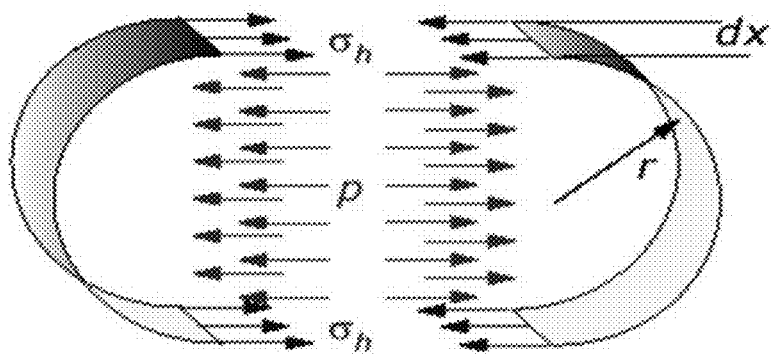

FIG. 64 depicts a diagram of hoop stresses in a cylinder.

Figure 65:
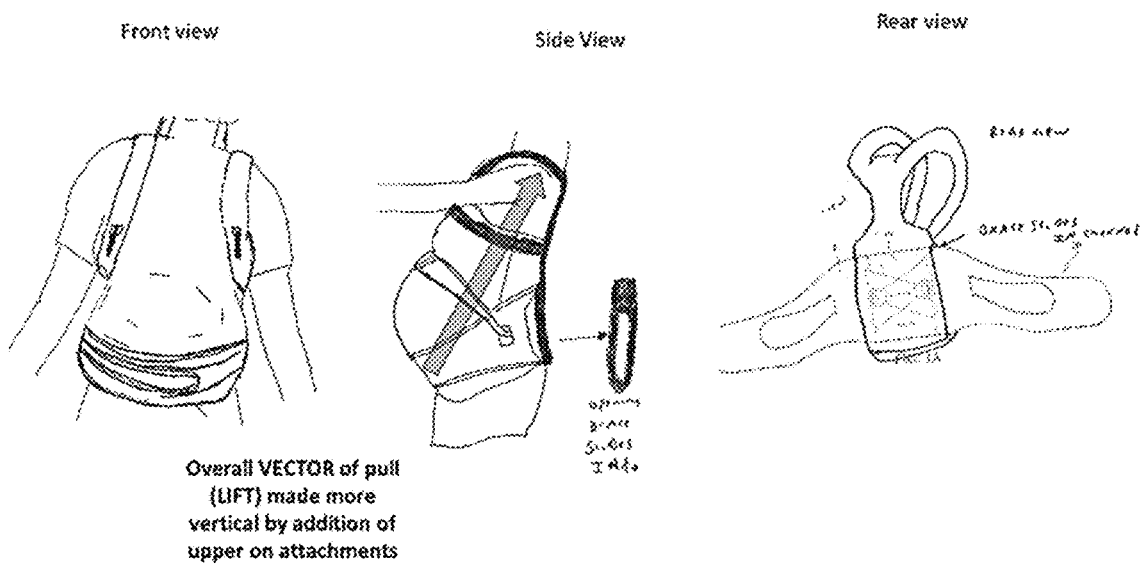

FIG. 65 depicts a diagram of an over the shoulder optional attachment to the present invention.

Figure 66:
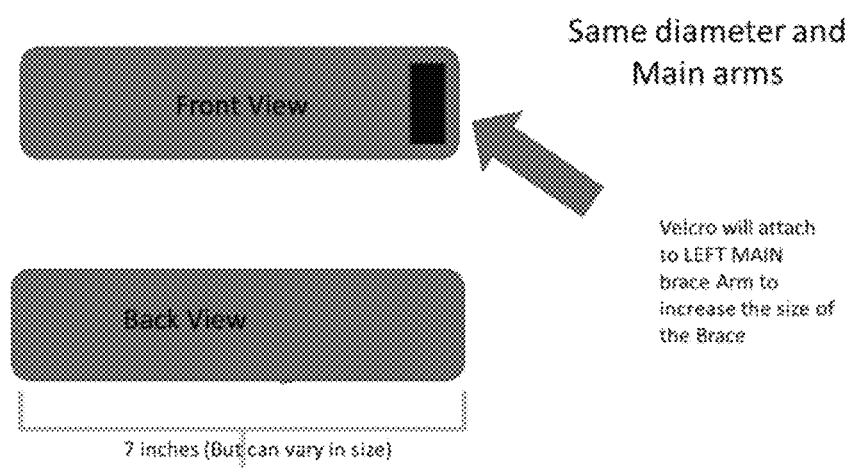

FIG. 66 depicts a brace extender attachment for use with the present invention.

Figures 67, 68:
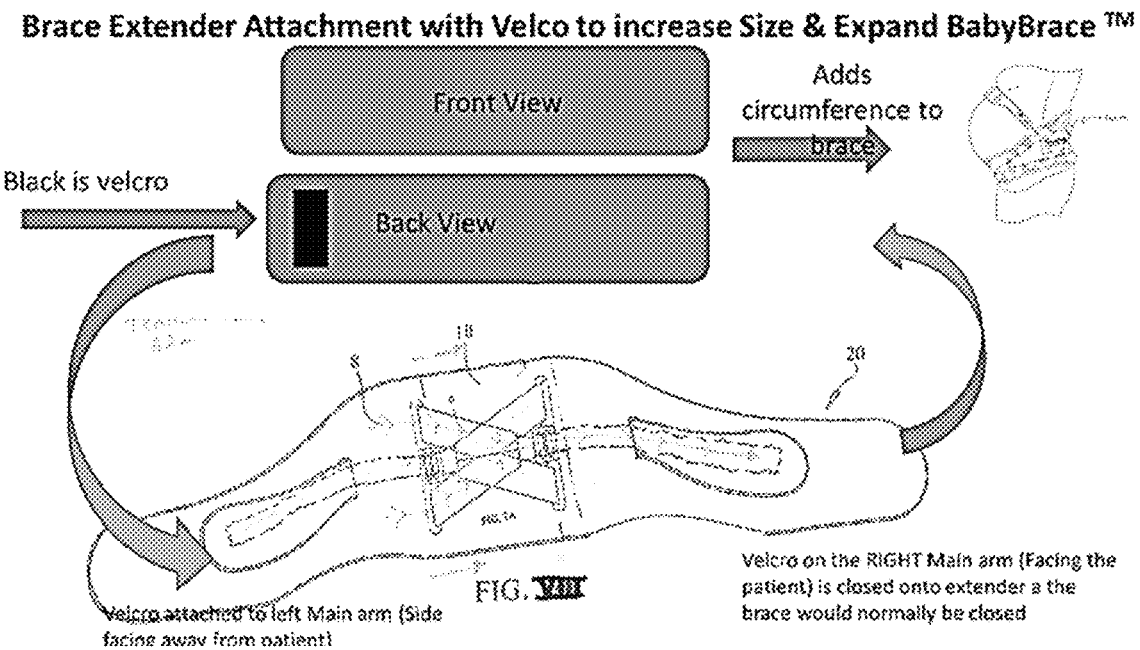

FIG. 67 depicts how a brace extender attachment, as in FIG. 66, may be used with the present invention.

FIG. 68 depicts a brace device for use with the present invention, that has been modified for athletics.

Figures 69, 70:
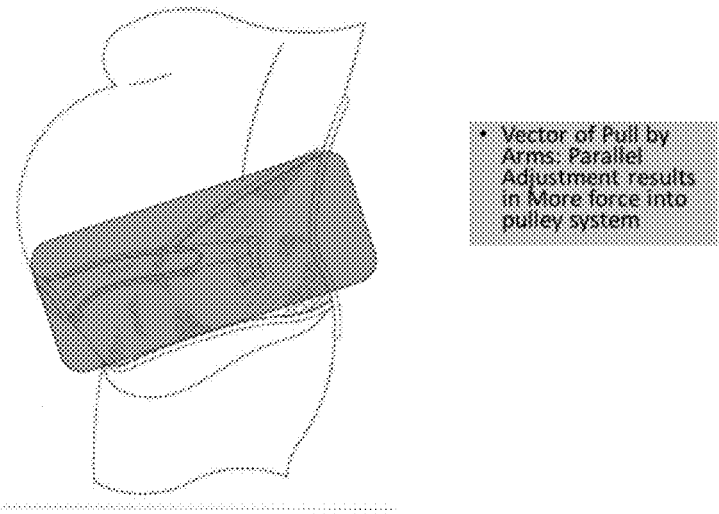

FIG. 69 depicts a brace device for use with the present invention, showing pull forces, which has been modified for athletics.

FIG. 70 depicts a brace device for use with the present invention, showing force vectors of pull after tensioning.

Figure 71:
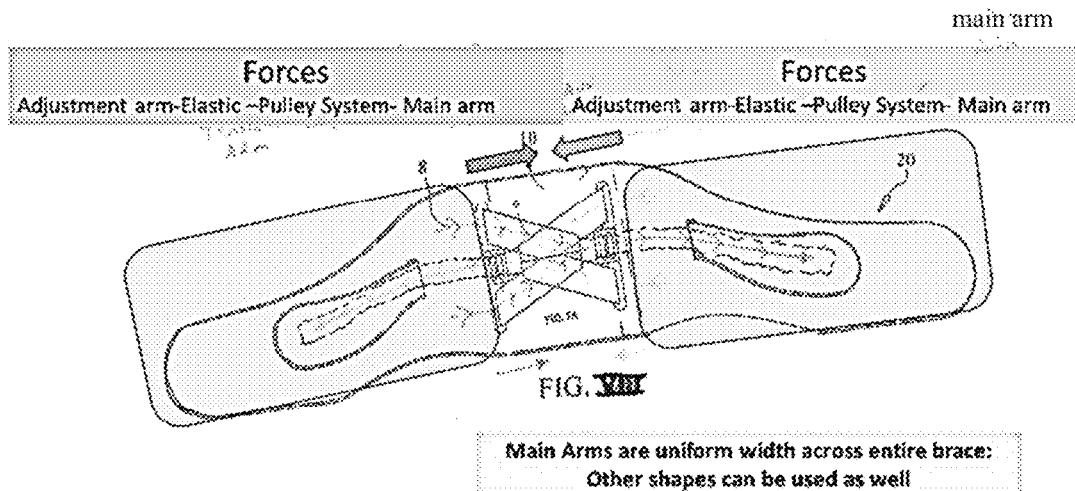

FIG. 71 depicts an internal view of an alternative brace, with an arm shape modification for golf.

Figure 72:
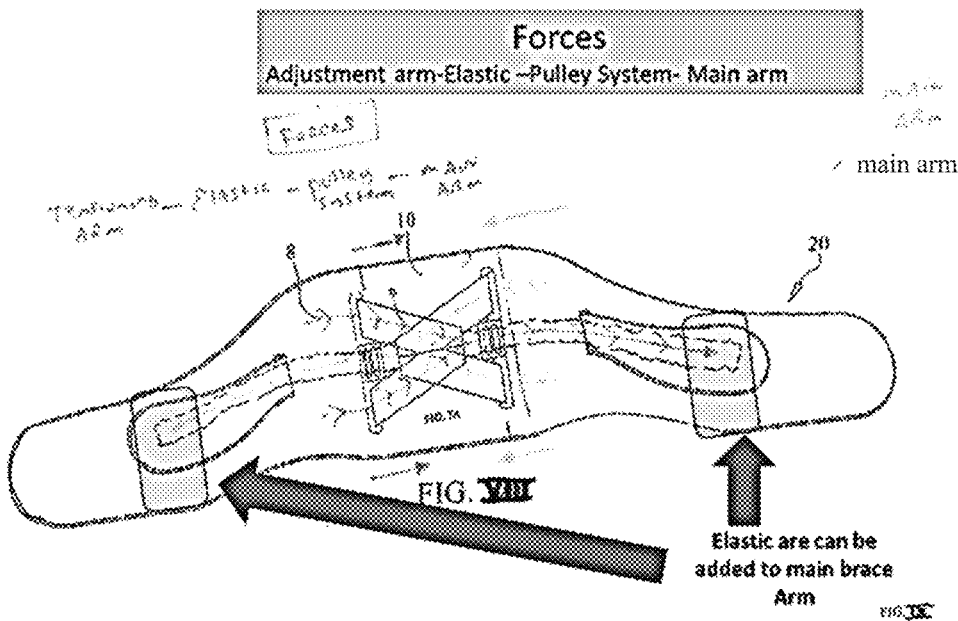

FIG. 72 depicts a cross section of an alternative brace pully system in accordance with example embodiments of the present invention. The example pully system has an added elastic section in the main arm.

Figures 73, 74:

FIG. 73 depicts a non-limiting example of a device in accordance with the present invention.

FIG. 74 is a sample size chart for sizing the baby brace of the present invention.

FIG. 75 provides further fitting instructions.

FIG. 76 provides further fitting instructions.

FIG. 77 depicts extra pads that may be used in connection with embodiments of the invention.

FIG. 78 depicts extra pads and possible add ons that may be used in connection with embodiments of the invention.

Figure 79:
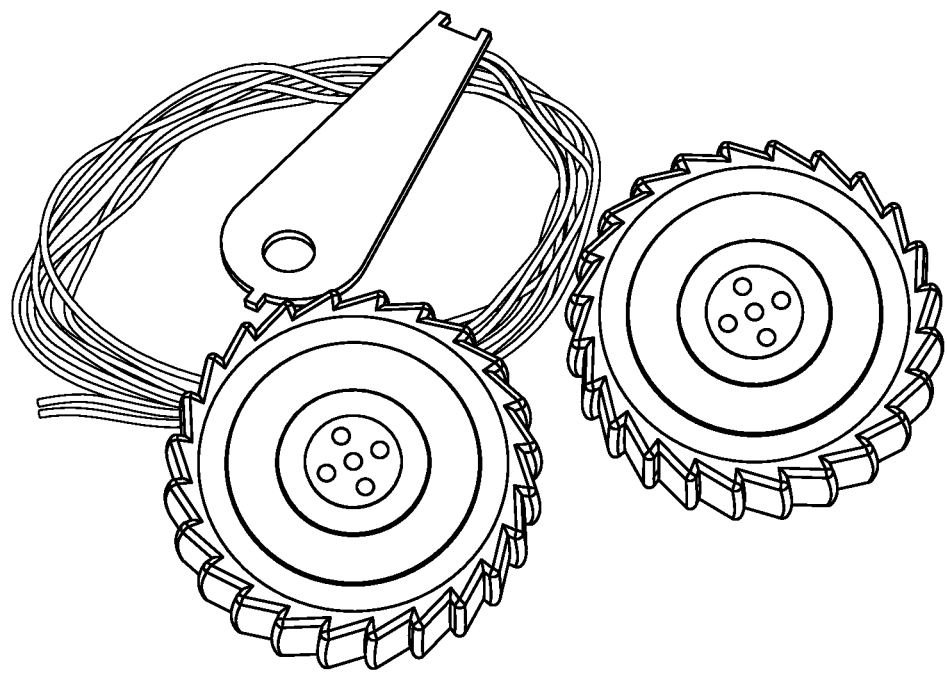

FIG. 79 depicts gears/wheels that may be used to help dial the appropriate device tensioning.

Figure 80:
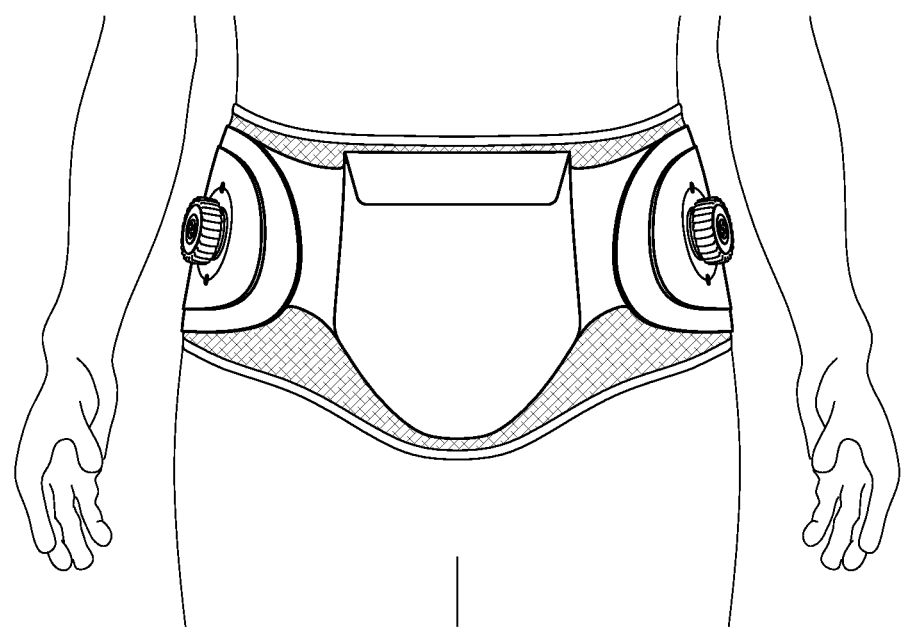

FIG. 80 depicts a belt adapted for use with the gears/dials of FIG. 79.

Figure 81:
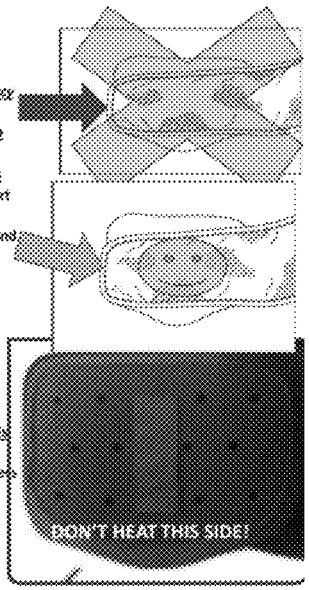

FIG. 81 depicts further add ons to example brace devices.

Figure 82:
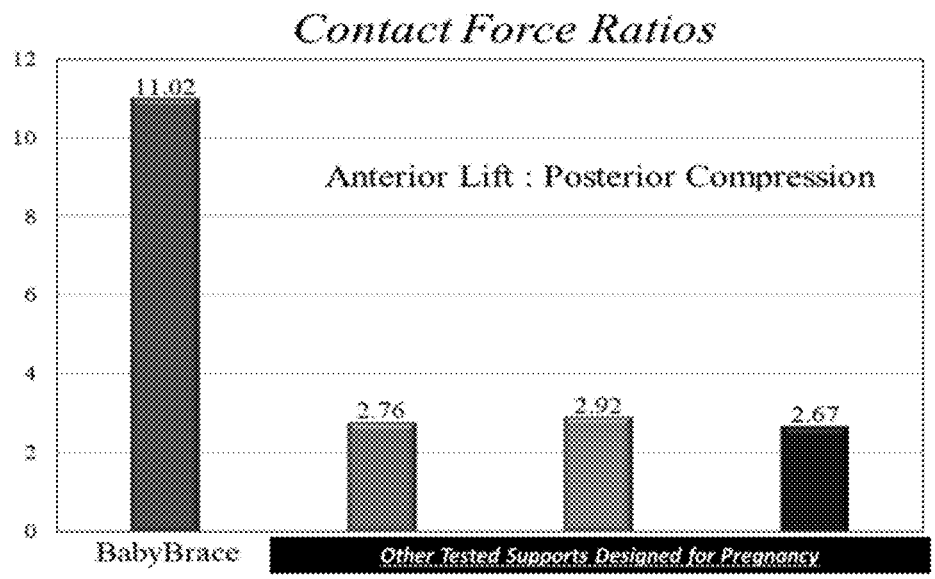

FIG. 82 depicts results of an experiment that shows advantageous results achieved by the present invention.

Figure 83:
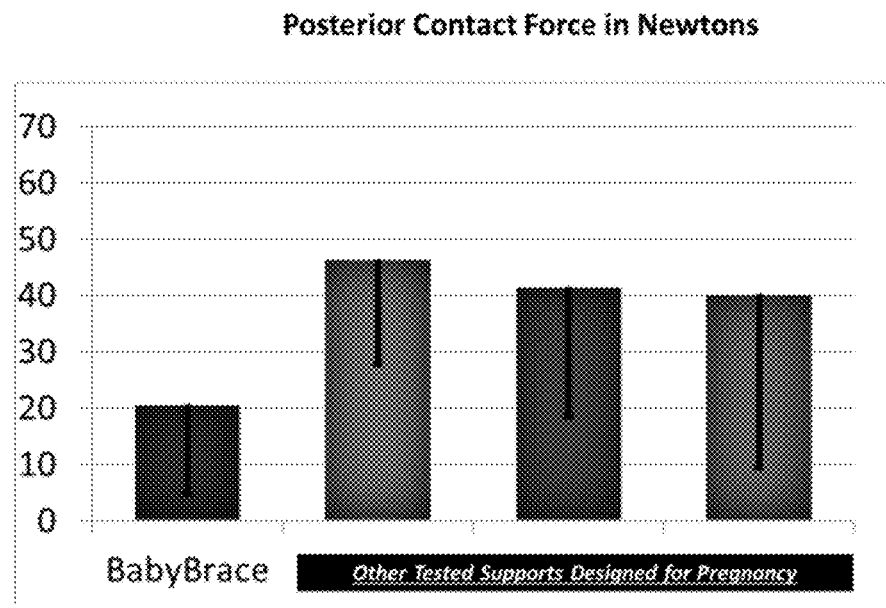

FIG. 83 depicts results of an experiment that shows a reduction in force achieved by the present invention.

Figure 84:
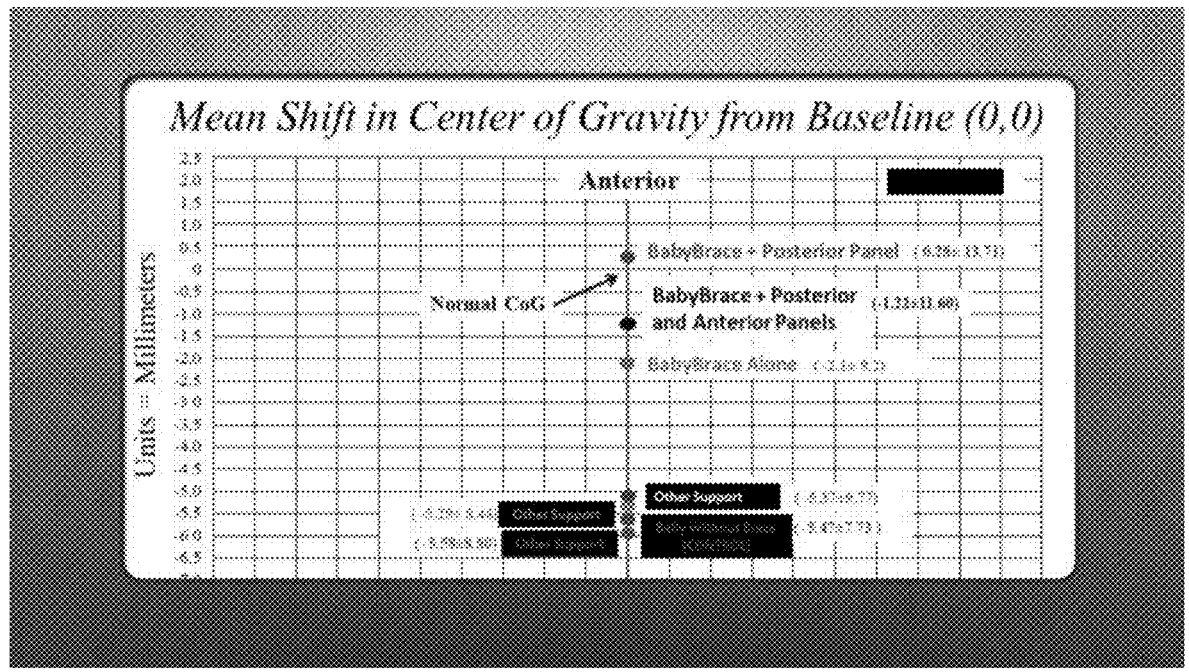

FIG. 84 depicts results of an experiment that shows advantageous results achieved by the present invention.

Figure 85:
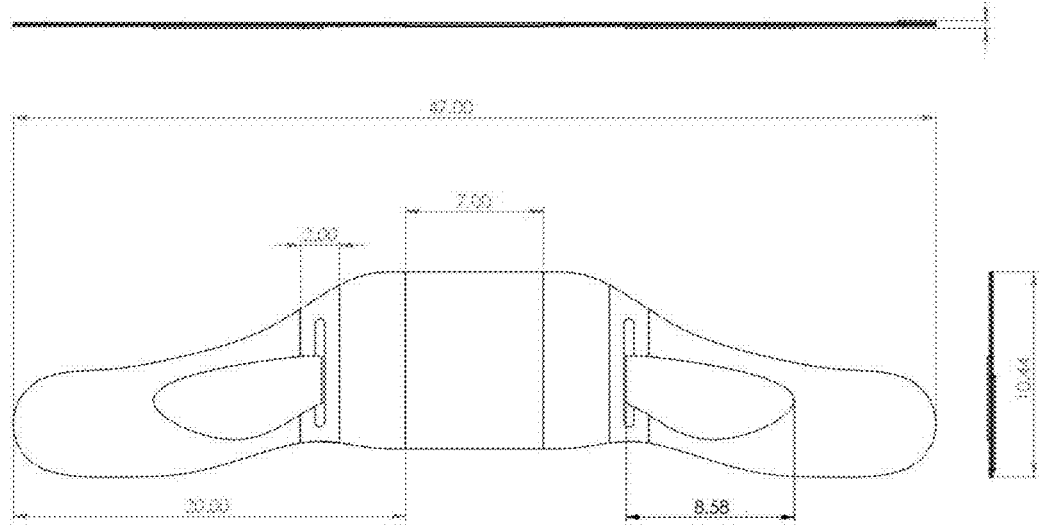

FIG. 85 depicts another non-limiting example embodiment of the present invention. This embodiment shows slits in the wings that are longer than the portion of the arms emerging from the slits in the wings. This configuration allows the arms greater movement for fitting the present devices.

Figure 86:
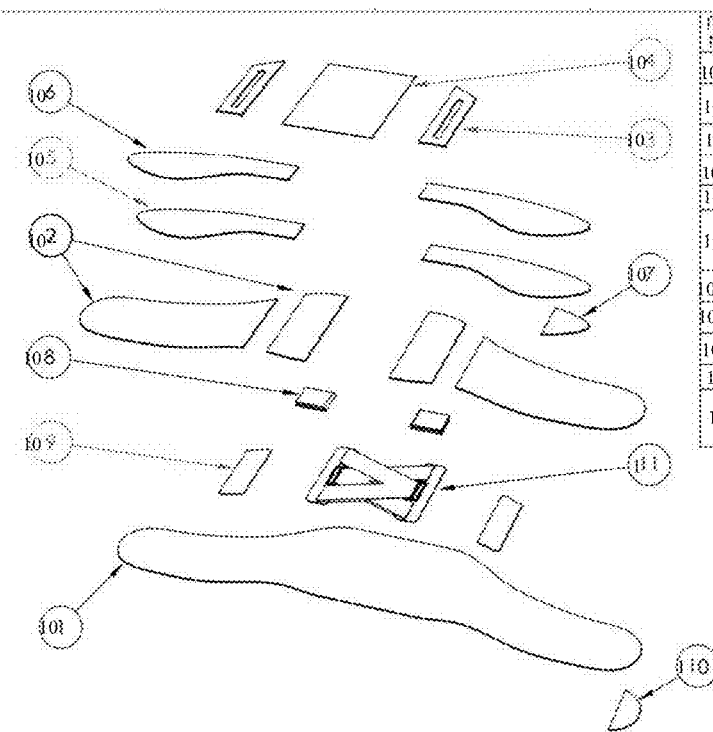

FIG. 86 is an exploded view of the device embodiment of FIG. 85.

Figure 87:
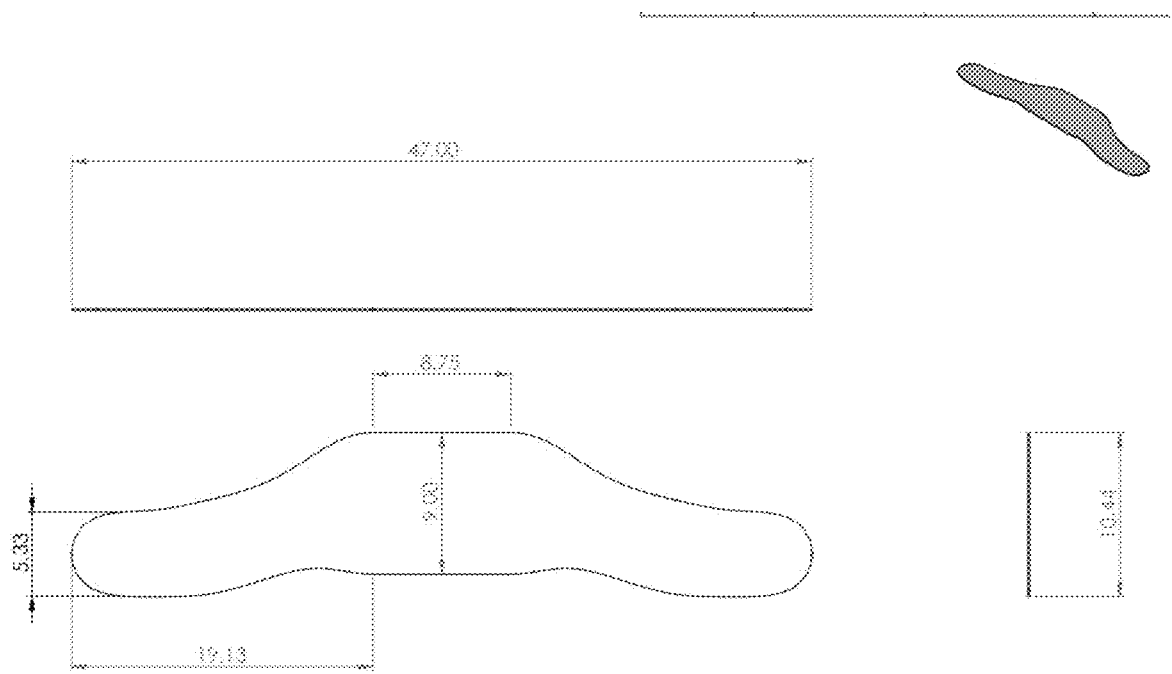

FIG. 87 is a wing assembly of the present embodiment of the present invention.

Figure 88:
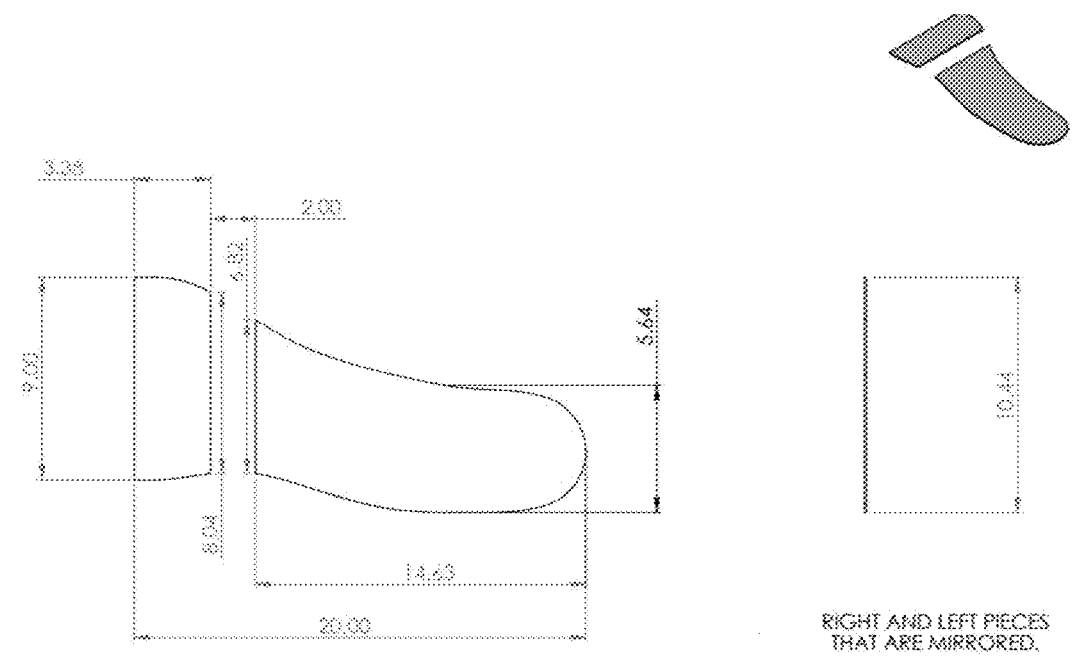

FIG. 88 depicts a portion of the wing assembly of the embodiment of FIG. 85.

Figure 89:
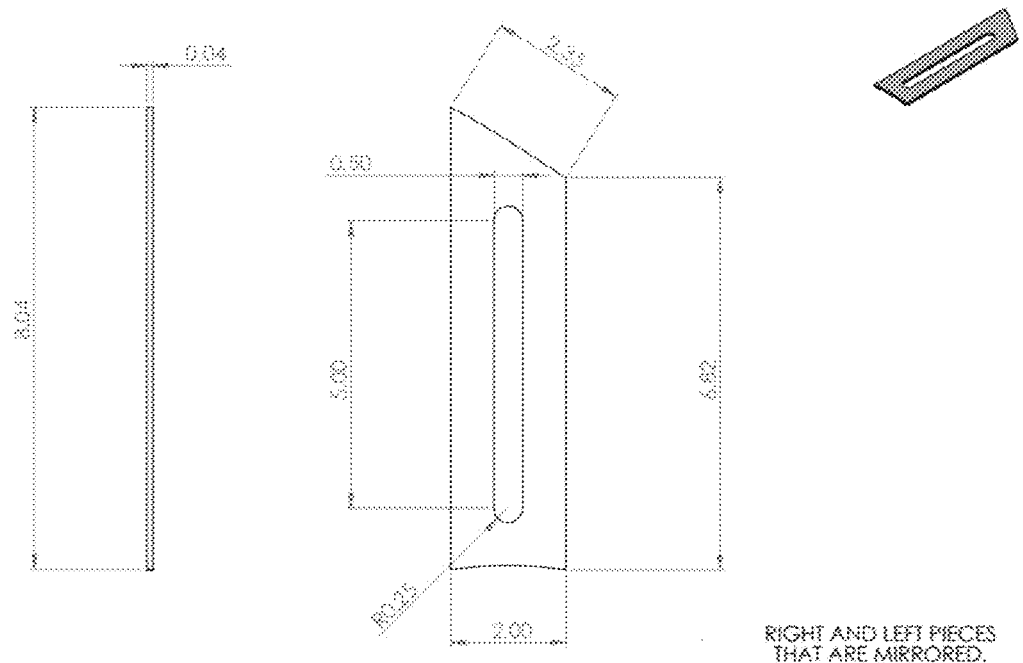

FIG. 89 depicts a portion of the present device, having slit boning.

Figure 90:
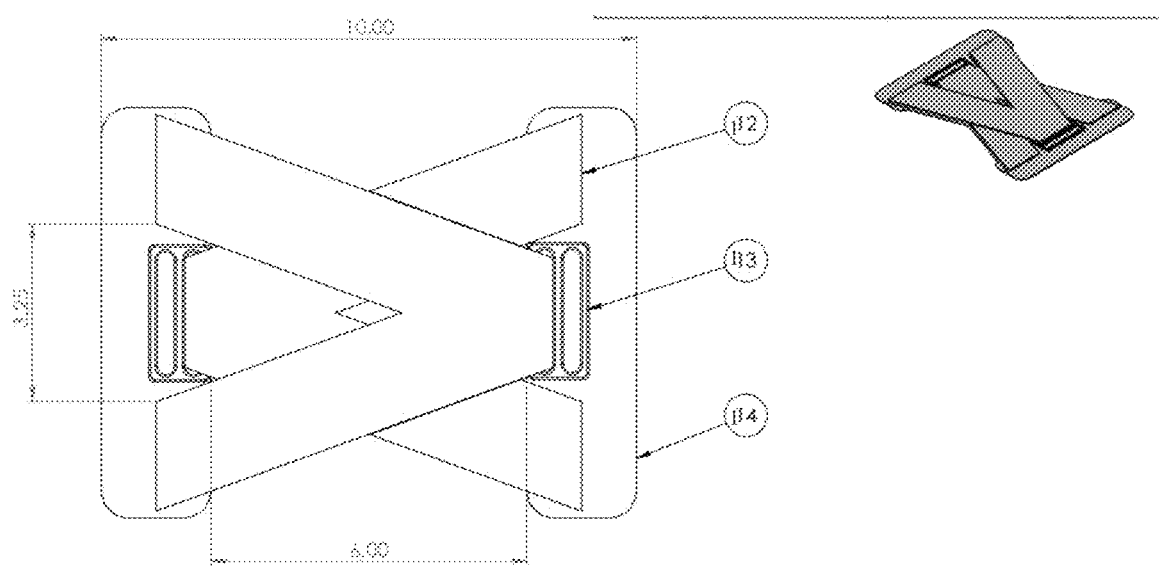

FIG. 90 depicts an example corset pulley system assembly according to non-limiting embodiments of the lumbar device of FIGS. 85. The corset pulley system assembly will be enclosed within the material of the brace.

FIG. 91 shows how customizations may be patient specific and fitters can use to tables to better instruct patients improving the brace effectiveness at reducing back pain.

FIG. 92 shows how customizations may be patient specific and fitters can use to tables to better instruct patients improving the brace effectiveness at reducing back pain. Fitters can optimize the brace effectiveness at neutralizing the negative effects of belly weight by using the tables three settings: adjustment arm tension, adjustment arm position and panel use. Fitters can recommend above different brace modifications base on tables.

DETAILED DESCRIPTION

Generally provided herein are methods and systems for reducing, treating and/or preventing back pain in an individual. Also provided are support devices that may be useful for prevention and/or treatment of back pain in a person. By way of non-limiting example, the present embodiments may include devices for prevention of back pain in pregnant female humans or post-partum individuals, or other persons that may for example, have excess belly weight, or persons that may have for example, Ascites.

Also provided herein are kits that include the present devices, and methods of preventing and/or reducing back pain in a person that include applying the present devices to a person in need thereof. A person in need of the present devices may include for example, pregnant female humans, persons having ascites, and/or persons having excess weight or bulk around the belly area.

Additional aspects, advantages and/or other features of example embodiments will become apparent in view of the following detailed description, taken in conjunction with the accompanying drawings. It should be apparent to those skilled in the art that the described embodiments provided herein are merely exemplary and illustrative and are not limiting. Numerous embodiments of modifications thereof are contemplated as falling within the scope of this disclosure and equivalents thereto.

Any references mentioned in this specification are indicative of the level of those skilled in the art to which the invention pertains. Any references herein are incorporated by reference to the same extent as if each was specifically and individually indicated as having been incorporated by reference in its entirety.

Any reference to color herein is exemplary and is not intended to be optional, and not limiting. The present devices and components thereof may be in any desired color(s). Any colors indicated herein are exemplary only and are not intended to be limiting.

Pregnancy causes the body's hormones to fluctuate causing many physiologic changes throughout the body. The key hormones that dramatically fluctuate during pregnancy are estrogen, progesterone and relaxin. Fluctuations in both estrogen and progesterone are necessary for a woman to become pregnant and for an expecting mother to carry her baby to term. During pregnancy, high progesterone levels function to maintain a healthy internal environment for the baby. However, as the progesterone and relaxin levels increase during pregnancy, joints, ligaments, tendons and tissues throughout the body relax and stretch. After the joints and ligaments relax, the lower back becomes more flexible and the body naturally changes the spinal alignment to compensate for the excess "belly weight" throughout pregnancy.

However, the added "belly weight" is like carrying a heavy object in front of the lower pelvis. In objects with an irregular or changing shape, as in the human body during pregnancy, the center of gravity ("COG") changes throughout different stages of pregnancy, as seen for example in FIGS. 49-51. As indicated in FIG. 51, the center of gravity shifts forward during pregnancy. Once the center of gravity shifts, the compensatory changes can lead to muscle imbalance, dysfunction and pain. FIG. 52 shows the internal anatomy of the present devices, with a pully system and elastic. FIG. 52 also shows that present embodiments may keep force parallel to the pulley system for a symmetric (even) pull.

The body's center of gravity is a single point at which gravity exerts its downward force (see FIG. 49). For one to balance and stand without falling over, a person's center of gravity must be balanced by coordinating and using their different muscle groups (especially core muscles and psoas muscle). In a normal, healthy standing individual, the center of gravity is typically located about 1 cm behind the junction of the lumbar spine and sacrum. However, during pregnancy (and for persons who are obese or have other medical conditions like ascites) excess "belly weight" shifts the center of gravity anteriorly (forward) several inches. The body compensates for this change by increasing the lower back's natural curvature to a more backward curvature, a condition called lordosis. Lordosis is a backward curvature of spine and helps to counter balance the change in the center of gravity.

This combination of increased belly weight, increased spinal flexibility, shifted center of gravity, and altered lumbar lordosis creates a delicate equilibrium (e.g., during pregnancy). Any additional activities or postural changes that create undue stress on the lumbar spine can lead to imbalance in the equilibrium. Ultimately, these changes can cause muscle imbalance leading to muscle fatigue. This muscle fatigue is a common cause of pregnancy related back pain and can develop into a more serious spinal disorder if untreated. Even in fit women, lower back pain is a painful reality that will affect 50-80 percent of all pregnant women.

Post-partum back pain can also occur because of weakened core muscles from stretching of lower abdominal muscles during vaginal delivery or abdominal incisions during Cesarean section delivery. Described herein are the methods and biomechanics by which the present invention functions to improve or reduce lower back pain (in pregnancy and other conditions that alter the center of gravity "COG").

The present device dynamically contours to the patient, placing the COG in a more natural and physiologically appropriate position. This reduces stresses on the spine's supporting muscles, thereby alleviating pain. The present invention includes a system and device designed to improve the COG changes that cause back pain, adjust to patient (size & shape) changes, adapt to the body habitus variations during pregnancy, and provide modularity for post-natal use, as described further herein.

Unless otherwise noted, technical terms are used according to conventional usage.

As used herein, "a" or "an" may mean one or more. Also, as used herein in the claim(s), when used in conjunction with the word "comprising", the words "a" or "an" may mean one or more than one. As used herein "another" may mean at least a second or more. Furthermore, unless otherwise required by context, singular terms include pluralities and plural terms include the singular.

The braces/devices described and used herein may be collectively referred to under the trademark BABYBRACE®. Accordingly, when used herein the term BABYBRACE® is intended to encompass the present invention. The terms "Modular Maternity Brace", "BABYBRACE®", "brace", "lumbar support device", and "device" as used herein, relate to the braces/devices described and depicted herein.

The present methods involve the use of the brace(s) to reduce the incidence of pregnancy related, post-natal, and golf or other sports, or work-related lower back pain: by using uplifting vector forces via an adjustable and variable tension pulley system.

Traditional treatments for back pain in general include administration of anti-inflammatory drugs and other medications. However, most medications cannot safely be used in pregnancy.

Bracing is a common treatment for lower back pain in general. However, most of the current commercial braces on the market are contraindicated in pregnancy. Current treatments targeting pregnancy-related low back pain include elastic bands to support the sacroiliac joints or lower back in combination with physical exercises recommended by the ACOG. Maternity braces currently on the market target pain during the third trimester, do not have a variable (or any) pulley system, and they are not modular. This limits their effectiveness at treating back pain because they cannot conform to the physiology changes throughout the stages of pregnancy (and/or post-partum).

Maternity braces currently being used are made mostly of elastic type materials that lack the substance to support and stabilize patients of variable sizes and body habitus. Other maternity braces on the market do not focus on improving physiologic changes that have resulted from changes in the center of gravity.

In contrast, traditional lower back braces used to treat non-pregnant patients use compressive forces and indiscriminately tighten. Because these braces indiscriminately tension the back brace without restriction, there are no protective mechanisms to adjust and modulate excessive forces produced with tightening. These traditional lumbar braces are therefore contraindicated in pregnancy. These braces tighten via tensioning mechanisms that increase abdominal stresses which are potentially harmful to the fetus. Most braces increase intra-abdominal pressure via hydraulic forces exerted on the anterior and posterior trunk. The increase in abdominal pressure may provide some relief of back pain, but also produces hydraulic forces that support the lower back anatomy.

Examples of braces that are L0637 and/or L0631 compliant but are contraindicated in pregnancy include, for example: Donjoy EXOS brace, Donjoy LSO brace, Aspen LSO brace, Mueller Lumbar Brace, etc. None of these braces however, may safely be used during pregnancy.

Typically, these braces are constructed of stiffer and ridged materials, which are less forgiving when forces are applied across them. Because these products are constructed of stiffer materials and have a pulley system that has no protective mechanism to safeguard over tensioning and subsequently excessive compression, they are contraindicated in pregnancy. These devices alone (without the add on panels) all indiscriminately compress increasing intrabdominal pressure and this is not desirable in pregnancy. In contrast, the present brace is constructed of softer and more pliable material to limit force transduction. But at the same time the panels (which are rigid) can be safely added to the present BABYBRACE® devices to provide additional support because of its design. This is because of the combined interaction between pulley system and less stiff material used. The panels will stiffen up the present devices to provide restriction and more support, but without the danger of excessive compression pushing on those panels seen with traditional LSO's which are designed to primarily squeeze.

The present methods, systems and braces are advantageous over general purpose braces, at least because they have protective mechanisms to avoid excessive forces produced with tightening prior braces. The present methods, systems and braces also avoid applying undue abdominal pressure. Further, the present braces are made of materials that do not transfer excessive force intra-abdominally via compression to the abdomen. Accordingly, the present braces are L0637 and L0631 compliant (as those brace codes are determined in 2018), but are specifically configured for use during pregnancy and may be advantageously used during pregnancy, as opposed to previous compliant back braces that are contra-indicated during pregnancy. Preferably, if the brace code(s) chance, the present devices may be modified by those skilled in the art to continue to meet the design codes.

Additionally, other supports fail to help most patients because they are not designed to improve the bio-mechanics (center of gravity) which causes the back pain. The present devices improve the center of gravity changes that cause lower back pain by creating under-belly lift and eliminating the ability to produce excessive forces. COG shifts posterior in most pregnant patients.

The second most common reason supports do not adequately help patients is that they do not fit appropriately, particularly the one-size-fits-all supports.

The present invention was invented to reduce lower back pain occurring in pregnancy and post-partum, and other disease processes that are caused by muscle dysfunction, changes in body habitus and changes in the center of gravity. The present invention was invented to address the two main issues that alter the pregnant females' normal muscle physiology during pregnancy causing lower back discomfort. These two main issues are a change in body habitus and a shift in the center of gravity (COG) leading to muscle dysfunction. By shifting COG in the individual to their more natural desired position. Although initially invented for these purposes, it is considered and contemplated that the present invention brace configuration is also useful for prevention, reduction and/or treatment of other conditions as well.

The present methods and devices, which are medical grade devices, available by prescription only, offer a patient back comfort and support during the stresses of pregnancy. A majority of pregnant women report experiencing back pain at some point during their pregnancy. The present invention addresses this painful issue by correcting the bio-mechanical deficiency, thus reducing symptoms.

Among the present methods, included herein are methods that include reducing, treating and/or preventing lower back pain in an individual (for example during pregnancy or post partum) by shifting the center of gravity in the individual to a desired center of gravity further to the posterior side of the individual, comprising applying modifiable lifting forces to a lower abdomen of the individual using a pully system, under the belly of the individual toward the desired center of gravity; and applying one or more vector forces from an anterior side of the individual toward the desired center of gravity. Depictions of the disrupted equilibrium and restored equilibrium (using the present methods and devices) are set forth in FIGS. 61-62.

FIG. 63 depicts steps of non-limiting examples of the present methods. In FIG. 63, a brace in accordance with the present invention may be applied to an individual in which the center of gravity and/or body habitus is causing back pain. The adjustment arms of the device are pulled and the brace tightened. Then the adjustment arms may be readjusted and individualized to the best resting position, which restores the center of gravity. The trunk muscles are verticalized which provides support and improves lower back pain.

The unique configuration and features of the present invention creates a relationship between the tensioning arms, elastic connection between pulley system and main brace arms that modulates hoop stresses produced by the pulley system (FIG. 64 depicts hoop stresses). Patients can selectively modulate hoop stresses by varying the tensioning arms forces that are transferred to the pulley system. The relationship between the pull of the tensioning arm and the forces transmitted to the brace's pulley system is not linear because of the elastic connection between the two. The degree of force transmission can be patient specific (and adjustable for comfort) by varying the vector of the tensioning arms' pull, the resting positioning of the tensioning and main brace arms, and the amount of force applied directly to the tensioning arm. Also, the tensioning arm—pulley system is constructed of material that allows the user to adjust the tension, force and uplifting vector pull. This is accomplished without indiscriminate tightening, which is undesirable and may be dangerous in the case of a pregnant patient. Described herein (including in the figures) are the unique methods by which the present invention functions. This brace uses an adjustable and variable tension pulley system to produce an uplifting vector (via hoop stress forces) and corrects the physiologic dysfunction caused by the changes described above.

The elastic between the adjustment arms and the pulley system creates a dynamic lift between the main brace arms and the adjustment arms that can be modified easily for patient comfort. This is a main advantage of the brace.

It is a goal of the present invention to provide a unique method of lumbar support using the present invention device (as shown for example, in FIG. 73) by using adjustable and variable force vectors to decrease the stresses on the spine improving posture/alignment. The present invention uses a uniquely configured tension-pulley system to create adjustable and variable tensioning. This method of tensioning a brace produces vector forces that are not excessive, but delivers the underbelly lift required to move the center of gravity to a physiologic position. The present braces will improve a pregnant (or other) patient's posture reducing the stresses that can lead to muscle fatigue and pain. This will improve overall core stabilization, spinal alignment and posture (e.g., during pregnancy), thereby reducing lower back pain during pregnancy caused by paraspinal muscle fatigue. It works by supporting the under-surface of the belly (like cradling hands), improving the patient's bio-mechanics and center of gravity.

According to further non-limiting example embodiments, unique methods are provided for producing and adjusting a lumbar brace's anterior "Lift" for pregnant patients. Also provided are unique methods of maximizing a brace's effectiveness at neutralizing excessive truncal body weight and abdominal weight gained during pregnancy. These methods and results achieved thereby may be accomplished by using a combination of patient specific measurements, estimating truncal body mass and cross-referencing research data on the present invention, specifically how this devices customization/modularity effects lift. The present devices have a unique design that allows patient specific customizations that are be used to create underbelly lift reducing back pain in pregnancy. The present invention produces underbelly lift without primary compression forces and with protective limits that reduce maximal compression. This method improves the center of gravity alterations (which is seen in patients with excess abdominal weight as well) is seen in pregnancy and other disorders ultimately the major contributing factor causing lower back discomfort.

The present embodiments include the following features: 1) Preventing over-tightening. The adjustment arm design and adjustment arm-pulley complex's interaction "limits out" tension within the brace as a safety feature to avoid too much pressure. Elastic (or other stretchable) materials are used. In addition (or alternatively), a torque-limited tightening device such as a precision fit dial (see e.g. FIG. 79 and FIG. 80), positioned between the adjustment arm and the pulley system, reduces the amount of tension the brace can produce and reduces overall maximum tightness within the closed brace. This was scientifically tested and proven. Pulling on the adjustment arm will produce a non-linear tension transmission to the main arms, such that the present invention can only be tightened so much. 2) Adjustment arm overlap also limits max tension. The adjustment arms must be fastened by hook and loop fastener together to wear the brace appropriately. If the adjustment arms are pulled too much, one will not be able to link the adjustment arms via the hook and loop attachments and close the brace correctly. These are two protective mechanisms built into the brace to avoid excessive tensioning. This is desirable in pregnancy to avoid excessive compression forces.

In contrast, other products do not have these two modes of protection built into them. Other devices, like many traditional braces with pulley systems are contra-indicated in pregnancy because there is no limit on the amount of "squeeze" compression the brace produces. Lastly, the other braces designed for use in pregnancy attempt to limit the compression the brace products by primarily using elastic materials which results in a brace that is too flimsy and cannot biomechanically achieve anterior "Lift" when its needed; especially in larger patients (obesity or just larger stature). The elastic band type supports that the inventor biomechanically tested all could not achieve the anterior newton forces: "Lift" that the present invention did: The main reason for this was inherent to the braces design which produces lift with substantial compression forces (which is not desirable in pregnancy for obvious reasons). The non-present invention products tested are also not a durable. They failed and 3-4 of each of the other braces were required to get through testing due to the failure. By comparison, only one product according to the present invention was used during biomechanical testing with no functional decline). The anterior lift to posterior compression ratio was calculated, and the present invention advantageously provides greater lift with less compression to produce the same lift:

In the present methods, "Lift "can be adjusted without opening the main arm of brace via the adjustment arms, which can easily modify the lift be two methods:
  A) The adjustment arms can be opened and retightened to apply more pull to the pulley system: and subsequently to the main arms producing lift, and/or
  B) The adjustment arms can be placed in different positions on (over) the main arms or above the belly to increase or decrease lift respectively. This is a very unique method of improving lift that is not known to be present in any other brace device.

In summary: "Lift" is adjusted via the tension within the adjustment arm pulley complex AND via the adjustment arm end position. This method and devices used to achieve such method, is unique to the present invention device. This is a novel method of creating and easily adjusting lift (with the brace main arms still closed). The present invention therefore, produced easy adjustable patient specific lift because the main arms remain closed.

When using the present devices, its configuration allows for multiple methods of producing anterior "Lift" preferential as opposed to unrestricted hydraulic compression forces seen with traditional braces. (This was scientifically tested and proven with basic science research).

The present device modularity (panels) and adjustment arm pulley complex unique design will produce patient specific lift after the main arms are closed. This will translate into customized lift after main arms are closed improving COG (Center of gravity). (This was scientifically tested and proven with clinical research). As indicated above, there are other braces with panels that are contraindicated in pregnancy. The present invention had a unique method of using the panels with the brace arms and pulley system to modify the physiologic alterations which lead to lower back pain in pregnant women. The combination of the present invention with the panels allows an additional method of preventing swayback (From belly weight), varying Anterior lift and improving COG alterations:

The Posterior Panel extends above T9. Therefore, it prevents the patient from going into hyperlordisis (sway back) because of the excessive pregnancy belly weight. It is known that pregnant women compensate for the belly weight by increasing the lumbar lordosis and this will result in muscle fatigue and lower back pain. The Posterior panel is placed between the brace and the patients back, so it disperses forces across the back reducing posterior compression (and compression overall). The posterior panel also acts a fulcrum and allows the present invention to provide move underbelly lift. (This was biomechanically tested). The present invention will improve center of gravity alterations in patients with excessive abdominal weight. The underbelly lift provided is easily adjustable, so patients can "Dial-In" patient specific lift based on their size/body habitus. (This was scientifically tested and proven).

A complex relationship between the shape of the brace, adjustable pulley system, the panels and brace materials allow the present unique methods of providing underbelly (anterior) lift without the indiscriminate circumferential "hydraulic" compression forces (that other braces produce). This was biomechanically tested as well.

The present invention was specifically designed for pregnant women but can be used for other applications to help patients with lower back pain (Truncal Obesity). The adjustment arms and variable adjustable pulley system complex of the present invention was scientifically tested and proven to provide patient specific "lift" for pregnant patients improving their COG. The adjustment arm position tension, modularity (with or without posterior panel) and end position of the adjustment arms (over or above the main brace arms) can accomplish this goal without opening up the main arms and re-tensioning the system. Opening the main brace arms and readjustment is the typical method other pregnancy braces function. It is well documented in the medical literature that that a women's COG changes during pregnancy because of excessive belly weight. A pregnant patients COG is displaced posteriorly in pregnancy but can move in other direction depending on the individual. The present invention adjustable variable pulley system complex allows the patient to customize the lift created within the brace improving COG. This has been scientifically tested and proven. The inventor's research also shows that by using the present invention to support the underbelly weight the COG will improved toward its natural position.

A traditional brace is tightened via a pulley system that indiscriminately tightens increasing compression and subsequently hydraulic force.

The present invention can function like a traditional LSO brace with its rigid panels. However, the adjustment arms, variable adjustable pulley system and modularity reduces (compression) forces which are undesirable in pregnant patients and maximizes lift (which is desirable in pregnant patients). (This was scientifically tested and proven).

This unique adjustment arm and (AV) pulley system also allows the patient to "dial" in lift based on their size and body habitus. This unique system also "limits out" the maximum tension because of the elastic connection better the adjustment arm and the pulley system in the back of the brace.

The lift is dialed in and customized (after the main brace arms are closed by varying adjustment arm orientation and tensions. These variations produce the desired lift without purely using compression forces seen with traditional braces. The adjustment arm has the ability to vary its end position because of the elastic connection to the pulley system and/or the large opening where that connection exits from the posterior brace. (The retail version described herein and depicted e.g. at FIGS. 85-89, has a large opening). The Applicant also contemplates that a torque-limiting dial, such as a BOA® DIAL may be used in place of elastic between the adjustment arms and the pulley system. Accordingly, such embodiments are included herein.

The BABYBRACE® method of improving back pain in pregnant patients does not exclusively use unrestricted compression and hydraulic forces like typical back braces. There are elastic "Ace bandage" type pregnancy supports that can provide some lift, but these products do not have the panels nor do they have a variable adjustable pulley system to "dial" in patient specific lift. The main way lift is adjustable with these products is with closing the main arms under different tensions.

Once BABYBRACE® main arms are closed the adjustment arms modulate lift via tension and adjustment arm end position (this is a unique methodology). Testing shows BABYBRACE® can produce comparable lift with less compression than other products and higher maximal lift in general (without linearly increasing compression). BABYBRACE® Variable Adjustable pulley system interaction with the adjustment arm limits maximum transmission to brace. Despite this fact BABYBRACE® still is able to achieve two times or greater lift when compared to other products.

In the methods of the present invention, changing the center of gravity may be achieved by applying a lumbar support device to an individual, the lumbar support device including at least two wings having wing fasteners to enable the wings to fasten to each other across a belly of a user; and at least two arms connected to each other by an elastic corset assembly, wherein the arms emerge from slits in the wings, said arms having arm fasteners to enable the arms to fasten to each other across, over, or under the belly of the user; and securing the lumbar support device to the individual by fastening the wings to one another and fastening the arms to one another.

Also provided herein are adjustable, modular lumbar support devices which include at least two wings having wing fasteners to enable the wings to fasten to each other across a belly of a user; and at least two arms connected to each other by an elastic corset assembly, wherein the arms emerge from slits in the wings, said arms having arm fasteners to enable the arms to fasten to each other across, over, or under the belly of the user; and wherein the support device is configured with a tension-pulley system to create adjustable and variable tensioning.

The forces required to change the center of gravity (COG) may be determined based on variations in patients belly weight gain, height and patient size. Additionally, the device size and shape may be determined based on variations in patients belly weight gain, height and patient size. Although a particular shape and size of the brace device herein and components thereof are depicted, other shapes and sizes may be suitable as well. For example, the brace may come in various sizes for differently sized people (by height and or weight). The brace may come in for example, small, medium, large, and extra large sizes. By way of non-limiting example, the sizes may be for belly sizes within a particular range. For example, size Small may be 28.5-43.1 inches, Medium may be 30.4-47.1 inches, Large may be 33.3-52.4 inches, and Extra Large may be 36.5-57.6 inches. These examples are non-limiting and those skilled in the art would recognize that other sizes such as XS and XXL may be used, as shown for example in FIGS. 74-76. Belly size may be determined for example, by taking a circumferential measurement of the patient's waist, starting from the hips to the umbilicus.

A sizing scale (as shown in FIGS. 74-76) should be used to guide the sizing process. The appropriate size may also be determined by taking into account how far into the pregnancy a user is. For example, if it is early in a pregnancy, a user may wish to obtain a brace that is one size larger than the measurement indicates. In the third trimester, the sizing may be true to size based on a sizing scale. Sample braces may be used to confirm size and fit. Before fitting, one may pull the brace main arms taut, so the adjustment arms are within their opening. (See FIG. 75).

In fitting, place one of the main brace arms on the lower belly (below the umbilicus), close (seal) the main arms using hook and loop attachments, the brace should lay on the lower abdomen below the umbilicus and be comfortable (never to snug). Pull both adjustment arms, resting the left arm on the upper abdomen and then use the hook and loop attachments to attach the right arm, preferably on upper abdomen. The adjustment arms can then be readjusted to the most comfortable position. (FIGS. 75-76).

The device may also be shaped in any way so as to provide a suitable fit to a wearer. By way of example, the device may have a somewhat straight bottom, or a bottom that is not straight across, but rather has two curved indents at the portions that may correspond to the location of hips of the wearer. According to non-limiting embodiments, the bottom shape may be straighter or have a greater curvature than that depicted. Other variations in shape may be contemplated by those skilled in the art with the present application in mind, so as to provide comfort and/or better fit to the wearer of the device. For the brace to work most effectively, it must be fitted to the patient.

Thus, according to non-limiting example embodiments, the device can be easily adjusted to conform to patients of different sizes, stature, and body weight, including through the course of pregnancy and post-natal changes.

According to non-limiting example embodiments, the support may be used for specified periods of time. According to non-limiting example embodiments, the present support devices may be used for example on a pregnant, human female throughout a woman's pregnancy, e.g., daily (e.g., 8 to 10 hours a day, 5 to 7 days a week), weekly (for example, several hours a day, one or two days a week), periodically (e.g., for four hours every morning or evening, or for increasing periods of time as the pregnancy progresses) or occasionally (for example during a portion of the day, when at work, when standing, when sitting for long periods of time, e.g., at the computer, on long car rides, when leaning over for greater than five minutes, when performing house chores, when gardening, when back pain starts to arise, or during other times of excess stress on one's back). In embodiments in which the present support or brace devices are used during a woman's pregnancy, the device may be adjusted to naturally contour/conform to the woman's anatomy, which changes throughout pregnancy.

The present lumbar support devices may optionally include one or more electronic components incorporated therein (e.g. incorporated in the fabric or between layers of fabric, or attached thereto), which are capable of detecting, measuring, calculating, and/or monitoring one or more maternal and/or fetal vital signs. Non-limiting examples of such vital signs may include, but are not limited to, fetal heart rate, maternal heart rate, fetal and maternal respiratory rate, placental blood flow and fetal/maternal electrocardiogram (ECG or EKG).

According to non-limiting example embodiments, electronics may be incorporated into or onto the device that may include a timing and/or distance counter (e.g. pedometer) which may determine e.g., the length of time the brace has been worn on a particular day, and/or the distance or number of steps that a wearer has walked while wearing the device. An example timer may either count up or down, to e.g. simply indicate to a user how long the device has been worn (so as not to exceed recommended wear time), or to count down the amount of time worn.

The electronic components may have a method of recording, displaying, and/or communicating such vital signs (or data). Data or calculated information (e.g. relating to vital signs, timing and/or distance) may be communicated to the wearer or other person (e.g. a nurse, doctor or family member) e.g. by viewing a display for example on the device, or viewing the information on e.g. personal electronic device, such as a smart phone, fitness tracker, or other device to which the information is communicated (e.g. using BLUETOOTH or other wired or wireless communication method), or on a computer to which the data has been communicated. Other methods of communication are also known in the art, including for example vibrations, lights, sounds and other methods for communicating information. For example, if fetal or maternal vital signs are not within a preferred range, a sound may be made, or a vibration made, or a message may be sent by email or text to the wearer or a medical professional.

The "electronic" component or device may take any suitable size or shape as would be apparent to those skilled in the art in view of the present application. The electronics may include electronic devices such as detection and/or monitoring devices for maternal and/or fetal vital signs. Example electronic devices are well known in the medical field. Additionally, the electronic devices may be incorporated e.g. in the fabric or between layers of fabric. The specific location of the electronic device on the lumbar support device may be determined e.g., based on which vital signs are being monitored, or the location may not be critical (for example in the case of a pedometer or a measurer of how long a device has been worn). The present application is not intended to be limited to the type, size, location of such an electronic device or component by including it in the figures.

Either raw or calculated data collected from the device may be provided to a medical professional, either directly (without additional affirmative action), or sent by the user (e.g. via email or internet connection—such as transferred by BLUETOOTH in the doctor's office), so that software may process the information to ensure that vital signs are within a desired range and to potentially diagnose potential abnormalities or medical issues with the mother and/or baby.

According to non-limiting example embodiments, lumbar support devices of the present invention further include at least one electronic component capable of measuring, calculating, monitoring, and/or adjusting one or more forms of data selected from the group consisting of maternal vital signs, fetal vital signs, time, distance, force, lift, and pressure.

Further provided are systems that include at least one lumbar support device, which includes electronics incorporated therein or thereon. The electronics may be for example, capable of detecting and/or monitoring one or more maternal and/or fetal vital signs as discussed above. The electronics may have a method of recording, displaying, and/or communicating such vital signs (or data). The systems may also include a smartphone or computer app or software that is capable of communicating with the lumbar support device either wired or wirelessly via a cord, wireless internet connection, BLUETOOTH or other method.

Non-limiting example embodiments of the present braces/support devices have multiple pressure sensors adapted to allow a user to dial in a exact force required to change the COG: The pressure sensors may be built in to the device/support. The pressure sensors may function for example, via a BLUETOOTH app (possibly the fetal monitoring incorporated too). In example embodiments, the device tensioning may be configured such that it may change in response to the force set by the user, e.g. in a computer, phone or other device app. Non-limiting example embodiments are directed to devices that include at least one of a BLUETOOTH pressure sensor, HR monitor, or ECT, for the forces the main brace arm "Lift" the underbelly. This will allow optimization of a smart device. Data may be gathered based on height, weight, hip thigh ratio and the pressure sensor data."

The following are example advantageous features of using a present device in accordance with example embodiments of the present invention:

The present device has tensioning arm attachments that control the forces transferred to its pulley system. The present invention has the following three main methods of varying the amount of forces transmitted within the brace thus creating variable lift. First, the two tensioning arms are connected to the pulley system via an elastic material (see e.g., FIGS. 4 and 7), which reduces the amount of energy transmitted to the pulley system, and subsequently to the main arms. This is important because it produces a non-linear transfer of forces from the tensioning arm to the pulley system. (See FIGS. 4 and 7).

A second method of varying the forces is placing elastic between the tensioning arm and pulley system also will produce pulling forces on both the tensioning arms and the pulley system/main arm at rest. The tensioning arm can increase the uplifting forces by being placed in different overlapping positions on the main arm. The elastic (between the tension arm—pulley system) distributes the tension forces across all the arms within the brace. The overall tensions can be customized and varied by pulling the tension arms tighter or altering their resting position on the abdomen.

Third, the tensioning arms can be placed in multiple positions during the tightening process therefore altering the vector of pull. By changing the tensioning arm position during tightening it will alter the amount of forces transmitted though the tensioning arms elastic connections to the pulley system. This will also change the amount of force and subsequent energy transmitted to the pulley altering the forces distributed system (throughout the brace). For example: (see FIG. 6) which shoes that pulling the arm in line (parallel) with the pulley system will transmit the greatest energy to the pulley system whereas pulling the arm in an upper ward position (see FIG. 5) will transmit less force and subsequently less energy to the pulley system.

The pulley system configuration and material reduces the forces transmitted from the tensioning arms to the main brace arms. This prevents over tensioning of the device by reducing circumferential stresses. The pulley system material distributes the pressure across the tensioning arms and main brace arm balancing hoop buttress forces. (See Figure of Pulley FIG. 8.)

Figure 12C:
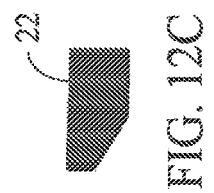
FIG. 12C depicts a perspective view of the example right side assembly of the corset fabric construction.

Another advantage of the present invention is that the shape of the main brace arms facilitates a position of comfort on the lower abdomen below the umbilicus. This position will also promote "uplifting" forces when the tensioning arms are tightened. The tensioning arms can easily be adjusted by the patient customizing resting position, lifting force and fit. The present invention allows the user to individualize the vector force transmitted through the brace arms without creating excessive post-tensioning stresses. (See e.g., FIGS. 11 and 12)

According to example embodiments, the lumbar support device is configured such that a fastened arm position, with respect to an individual to whom the lumbar support device is applied, is variable. According to example embodiments, the arms are positioned with respect to a user such that the arms are fastened to one another so as to rest over the fastened wings. According to other example embodiments, the arms are positioned with respect to the user such that the arms are fastened to one another so as to rest on an upper abdominal belly of the user.

The present invention is configured to reduce compressive hydraulic forces and maximize under belly lift via hoop buttressing forces. The uplifting support pushes the center of gravity while leaving the abdomen free flowing. This method of force transmission using a brace is novel because the configuration avoids excessive hydraulic forced compression and maximizes uplift via hoop buttressing forces. This device reduces compressive forces using the novel techniques/methods described e.g., in FIGS. 4, 7, 8, 11 and 12.

The present invention is configured specifically for use in pregnancy, but may also be used in connection with obesity, such as truncal obesity) and other diseases that shift the center of gravity anteriorly because of changes in body habitus. The interaction between the present pulley system, main and tensions arms, as well as the materials in those sub segments allows the present invention to have a unique method of vector force transmission. The tensioning arms, elastic connector strap, pulley system and main brace arms work synergistically to modulate the forces transmitted to the abdominal cavity. Compressive forces are minimized and this creates more beneficial "uplifting" of the lower abdomen.

The present invention is an orthotic stabilization and support which utilizes circumferential uplifting vectors minimizing excessive compressive forces required to do such, because these forces can compress the uterine contents. All braces that squeeze will increase hydraulic pressure, but the present devices are configured to maximize lift. The present invention creates up-lifting vectors that can be modified based on the final resting position of the tensioning arms. There is an elastic strap in between the tensioning arms and pulley system creating additional pull through the tensioning arms after tightening. One can use the tensioning arms final resting position to increase and/or change the vector of force created by the brace. (See e.g., FIGS. 10, 11 and 12)

The present device uses a method of bracing the lumbar spine and musculature while simultaneously allowing free flow of abdominal contents and pelvic contents without excessively increasing the cavity pressure, instead it utilizes hoop buttressing methodology. The tensioning arms, elastic connector strap, pulley system and main brace arms work synergistically to modulate the forces transmitted to the abdominal cavity. Compressive forces are minimized and this creates more beneficial "uplifting" of the lower abdomen. (See e.g., FIGS. 1, 13, 14 and 15).

The modular panels of the present device can be used throughout the different stages of pregnancy for additional support if necessary. If the patient requires additional uplifting forces to shift the center of gravity, then around the shoulder straps 52 can be added on to the main brace, as shown for example in FIG. 65. The main brace 50 slides through a fabric opening 51 in the over the shoulder attachment. This allows vector forces to be pushed toward the shoulders in patients that require such and/or haven't received relief from the other brace attachments. Larger patients are more likely to benefit from the over the shoulder addition because more uplift is required to shift their COG. The panels and upper arm straps additions are optional and require trained medical personnel to assure appropriate use.

The present invention utilizes the present devices as a lower abdominal orthotic that is worn below the umbilicus and configured to move the center of gravity to a more physiologic position during pregnancy and other changes in body habitus. The present invention has an adjustable and variable pulley system configured to change the vectors and/or forces applied through the orthotic. The pulley system configuration and materials in the present invention uniquely vary force transmission throughout the device. The tensioning arms, pulley system, and the elastic connection between the two are configured to work synergistically and balance forces within the brace. This allows the user to customize the brace tensions throughout the orthotic without over tensioning and creating excessive abdominal pressure. The present invention produces controlled uplifting of the abdominal contents which shifts the overall center of gravity to a more naturally position. This allows the lumbar core muscles to function in a more efficient manner reducing back pain caused by fatigue.

According to non-limiting example embodiments, the devices provided herein may be used as a maternity brace throughout a woman's pregnancy (even as the woman's anatomy changes throughout the pregnancy). When used as a maternity brace, the present devices may be used both during pregnancy for gestational support and/or post-partum (post-natal support), because they are adjustable and modular and have safety mechanisms therein to prevent over-tensioning. The present devices may also be used as lumbar support braces for persons who have excess belly weight or persons with ascites, or for golfers or others who may experience lower back pain due to weight, weight distribution, athletic activity, or work movement.

Also provided herein are methods of preventing or treating back pain in a person (such as a pregnant, human female or other person who may benefit from support provided by wearing the device) that include applying the devices described herein to a person, such that the person may wear the device. Examples of such devices may include e.g., the devices described herein.

The present methods of preventing or treating back pain in a person, may include applying a lumbar support device to an individual, said lumbar support device comprising at least two wings having wing fasteners to enable the wings to fasten to each other across a belly of a user; and at least two arms connected to each other by an elastic corset assembly, wherein the arms emerge from slits in the wings, said arms having arm fasteners to enable the arms to fasten to each other across, over, or under the belly of the user; and securing the lumbar support device to the individual by fastening the wings to one another and then fastening the arms to one another around the user's belly. The present methods may also include applying the lumbar support device to the individual, where the applying includes positioning the lumbar support device on the individual such that a posterior portion of the lumbar support device is across a back of the individual. Securing the lumber support device to the individual may include positioning and attaching the wings over the abdomen of the individual and fastening the wings to one another, and positioning and attaching arms having an elastomeric corset assembly, together across, over or under the belly to a desired position and tension.

Example methods may include applying a lumbar support device to an individual, wherein the lumbar support device includes at least two wings having wing fasteners to enable the wings to fasten to each other across a belly of a user; and at least two arms connected to each other by an elastic corset assembly, wherein the arms emerge from slits in the wings, said arms having arm fasteners to enable the arms to fasten to each other across, over, or under the belly of the user; and securing the lumbar support device to the individual by fastening the wings to one another and fastening the arms to one another.

Such methods may include positioning and attaching the wings over the abdomen of the individual and fastening the wings to one another, and positioning and attaching arms having an elastomeric corset assembly, together across, over or under the belly to a desired position and tension.

The slits in the wings may advantageously be raised and/or lengthened, to allow the arms to move up and down if desired, for better fitting. The larger opening is beneficial for the adjustment arms. (See FIGS. 52-60)

By way of non-limiting example, the device may be applied to a wearer by a method that includes applying the lumbar support device to the individual comprises positioning the lumbar support device on the individual such that a posterior portion of the lumbar support device is across a back of the individual, and securing the lumber support device to the individual by positioning and attaching the wings over the abdomen of the individual and fastening the wings to one another, and positioning and attaching arms having an elastomeric corset assembly, together across, over or under the belly to a desired position and tension. (See FIG. 63).

As indicated above, provided herein are inter alia, methods of preventing and/or reducing back pain in a person that include the person applying a lumbar support device provided herein to their back and securing the device around their belly. According to example embodiments, the devices may be applied to a person either by the person themselves or with the assistance of another person. The devices may be applied by a method that includes positioning the device on the person such that a posterior panel(s) (when used) or middle portion of the wings is positioned across a back of the person. Such positioning may include for example, overlapping the wings/main straps to one another across the belly of an individual and attaching them to one another around the waist of the user. The wings may be attachable e.g., with buttons, zipper, hook and eye, snaps, hook and loop (e.g., VELCRO®), or another fastener. If a front panel is present, the front panel may be adjusted, e.g. by moving the panel to a preferred position. Once positioned correctly, one may close the wings over the abdomen of the wearer. The present methods also include pulling the arms of the device from their positions through slits in the wings until they are at a desired length to be positioned around, over, or under the belly, and then attaching the arms to one another. See FIG. 63

According to non-limiting examples, when one or more panels are used, the plastic that forms the rigid side in an orthotics oven may be heated e.g., in a heating over, for example, for 15 minutes, such that it is malleable. Alternatively, or additionally, a heat gun can be used to mold the thermoelastic plastic by hand (so it conforms better to the patient customizing the panels fit). After the panels are heated and malleable: it may be positioned against the patient's back and held until the plastic is set to mold to the desired shape. One may want to push the back panel out to achieve lordosis to relieve tension. One may want to push the back panel out to achieve lordosis to relieve tension. The panel would be molded by hand by a medical professional trained to do so (e.g., Physician or orthotist). One would not want to place the hot panel on the patient. FIG. 78 discusses, where an example posterior panel may be placed, how it may be attached to the device (e.g. using VELCRO) and the use of a heat gun to heat up the panel for customization. For example, once the brace is heated, the thermoelastic plastic can be hand molded to custom fit the patient. The panel should be allowed to cool and then reattached to the brace. FIG. 81 depicts an anterior panel and discusses e.g., the heating and molding of such a panel.

After the wings are positioned over a person's abdomen and attached to one another by a fastener, then the wearer may further secure or adjust the device by adjusting the arms. The arms may be secured and adjusted for example by pulling on the respective arms e.g., anteriorly (toward the front), which pulls on the arms and corset, and therefore, tighten the arms over the front of the body to help it conform to the belly and back.

The present invention restores the COG and this optimizes vertical core muscle pull against gravity. The spines supporting muscles groups where intended to function this way, so that they do not fatigue as they maintain upright posture. The restoration of the COG allows the rectus abdominal, paraspinal and psoas muscles all to work more effectively because they have a vertical muscle pull. This improves the muscles lever arm, reduces fatigue and the incidence of lower back pain. This invention capitalizes on a unique methodology.

Other conventional, non-pregnancy, orthotic methods have not focused on restoring the center of gravity and/or correcting muscle imbalances caused by body habitus changes. They also have not attempted to use an adjustable and variable tensioning pulley system to accomplish this goal, maximizing uplifting hoop buttress forces (see FIG. 64) while reducing suboptimal hydraulic compression forces.

The current embodiments embark on a unique method of lumbar stabilization. The present methods restore the center of gravity into a more physiologic location. This is unlike conventional orthotic methods which utilize in discriminant pulley tensioning resulting in equal circumferentially abdominal compression pressure around the entire orthotic. The present novel methods do not depend on anterior abdominal hydraulic pressure to reduce back pain. Uplifting hoop buttress forces can be modulated by the user adjusting the overall tension and or resting position of the tensioning arms. This simply restores the center of gravity, improves muscle efficiency and reduces back pain.

Different versions of the brace can be configured to target different causes of lower back pain (not just pregnancy and/or body habitus changes resulting in lower back pain). The pulley system complex consists of the adjusting arms, elastic attachments between the adjusting arm and the pulley system, and the pulley-system itself with its attachments to the main brace arms. The pulley system complex can be configured to include different materials, in general to target other causes of back pain. By using elastic materials (or other materials) of varying resistances for example (and using other materials in the brace arms), the biomechanics of the brace can be altered (while still retaining the desire able equilibration function). The brace dynamically equilibrates the forces throughout the orthosis.

By using different materials and/or brace shapes on the brace it will change the forces and vectors produced. Also, by varying the shape and/or materials of the main brace arms (to a rectangular shape with rounded edges) it will reduce the lifting characteristics of the brace creating compressive forces (like a traditional brace.) Adding an additional band of elastic to mid-section of both main brace arm will further reduce lifting characteristics.

Biomechanical studies have confirmed the following benefits of the methods, devices and systems of the present invention (see FIGS. 51-60): 1) center of gravity is moved to anatomic position by the present brace (FIG. 51); 2) that the present pulley system yields uniform compression and EQUILIBRATES forces across the brace arms: without excessive forces intra-abdominal (FIGS. 61-62); and 3) showing how the pulley system arm combo is DYNAMIC and adjusts to changes in body when tensioning arms at rest.

FIG. 56 depicts an expanded cross-section of embodiments of the present invention. In FIG. 56, devices are depicted in which the design and elastic material within the pulley system reduce pressure exerted by the posterior brace.

FIG. 57 shows force vectors during the adjustment process of the present devices. FIG. 58 shows force factors after the adjustment process.

FIG. 59 depicts force vectors of pull after adjustment in a resting position. The overall vector of pull (lift) is made more vertical by having the tension arm position on the upper abdomen. FIG. 60 depicts that the vector of force is made stronger with overlapping straps.

FIGS. 61 and 62 show equilibrium disruption between anterior and posterior spinal supporting musculature, and equilibrium restored (due to use of the present device) between anterior and posterior spinal supporting musculature. The device permits the center of gravity to be shifted back to a more physiologic position. This allows the posterior paraspinal musculature to pull more vertically and work more efficiently to support the trunk.

The pulley system may be used as a dynamic elastic brace to be worn during golf swing or other athletic activity (See FIGS. 68-72): the brace still has the same pulley mechanisms: the materials and overall shape would just change because one would want some restriction and to increase abdominal forces in that situation. Golfers have a higher incidence of lower back discomfort secondary to increased stresses on their lower back throughout their golf swing.

The pulley system complex and brace arm shape can be altered by using materials of varying resistance. In example embodiments, the vector of pull may be made stronger with overlapping straps. These material changes will increase tension but still equilibrate the brace throughout the golfer's swing. The present methods and systems can be specifically configured to reduce (and protect) lower back pain in golfers without interfering with their swing. The golf swing rotation is about one or two seconds. The dynamic function of the brace will equilibrate the forces throughout the golf swing optimizing fit and stabilization throughout. However, golfers as opposed to pregnant females require additional support which can be accomplished with simple material changes and/or arm shape variations.

When a brace is used for athletic purposes, the brace may advantageously have symmetric width, as uplift is not required. For example, as shown in FIG. 71, the main arms may be a more uniform width across the entire brace. But the shape is not intended to be limited to this embodiment.

In the athletic versions, pulley system materials and their resistance may be changed somewhat from the pregnancy versions to increase forces but retain the equilibration characteristics of the brace. The "mustache" shape of pregnancy brace has from posterior view may be altered in a golf (or other athletic) type brace. The golf brace will have symmetric width like standard lumbar orthosis because uplift not required. Then it will have a pulley system which functions the same as with the pregnancy brace.

It is contemplated that elastic strings may be used instead of bands in the pulley system in the main arm(s) to dissipate the forces to the main arms through the pulley system, then add the elastic in the brace arm to further dissipate the forces, as shown in FIG. 72. Such embodiments and other modifications within the scope of those skilled in the art should be deemed as being within the scope of this invention.

Further provided herein are upper arm attachments for the present invention such as those depicted in FIG. 65 herein.

Provided herein are adjustable, lumbar support devices. Example embodiments include lumbar support devices that may include one or more detachable padded panels to provide additional support. In particular, provided herein are lumbar support devices that include at least two wings having wing fasteners to enable the wings to fasten to each other across a belly of a user; and at least two arms connected to each other by an elastic corset assembly. The arms emerge from slits in the wings. The arms have arm fasteners to enable the arms to fasten to each other across, over, or under the belly of the user.

According to non-limiting example embodiments, adjustable lumbar support devices are provided, which may optionally include one or more detachable padded panels for additional support if desired. FIGS. 1A-28C depict various views of non-limiting example embodiments of the present adjustable lumbar supports, without depicting the optional modular padded panels which may be added thereto.

FIGS. 29-34, 41-42, 44-46B, 48A and 48B depict example detachable padded panels. FIGS. 35-40 and 47 are drawings of example devices provided herein including drawings of the device in use.

FIGS. 1A and 1B depict front/anterior perspective views of an example lumbar support device 20 provided herein. These views depict, inter alia, first and second right and left wings 8 of the device that are connected there-between by one or more material portion 10. The fabric portion 10 may include various materials including for example lycra and cotton.

The depicted device shows first and second arms 17 that protrude from slits in the wings on either side of the device. FIG. 1C is a front/anterior view of the lumbar support device 20. The arms may be pulled around either side of a user and secured around, above or below a user's belly.

Figure 2:
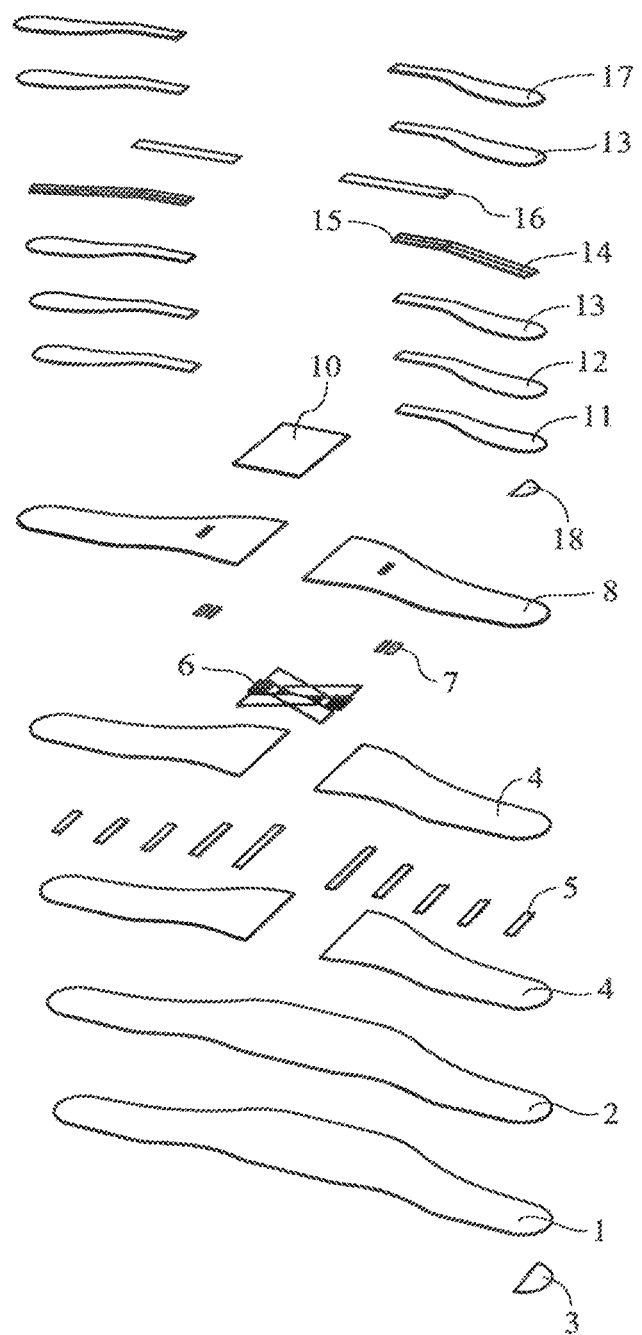
FIG. 2 depicts an exploded view of components of a non-limiting example lumbar support device 20 of FIGS. 1A-1E.

FIG. 2 depicts an exploded view of components of a non-limiting example lumbar support device 20 provided herein. In particular FIG. 2 shows various layers of fabric, mesh, lycra, boning, elastic, and other components of the wings, arms, corset pulley system assembly, etc. of example embodiments.

The depicted embodiments include the following layers: A first cotton layer, which is a base layer of wings of the present device, the bottom side of layer 1 is the portion of the device that contacts a user upon application of the device to a user. Next a padding layer 2 is provided. Next is a wing rib assembly having e.g., four mesh wings 4 with wing ribs 5 there-between. A corset pulley system assembly 6 is provided which attaches to ends of arms (layers 11-17). The arms are fed through slits in wings.

FIGS. 3A and 3B depict layer 1 of fabric (e.g. cotton) from a posterior view (FIG. 3A) of the lumbar support device of FIGS. 1A-2. FIG. 3B depicts a side view of layer 1.

A second padding layer 2 (from the exploded view of FIG. 2) of the lumbar device is depicted in FIG. 4A. The padding layer may be made for example of cotton, and may be formed to essentially be the same size and shape of the fabric layer 1, or may be made to be smaller than such fabric layer 1. FIG. 4B depicts a cross section of the padding layer 2. In alternative embodiments, padding 2 may be eliminated in favor of for example, a thicker layer 1 (if desired). Or according to other embodiments, additional padding layers may be added.

Figure 5A:
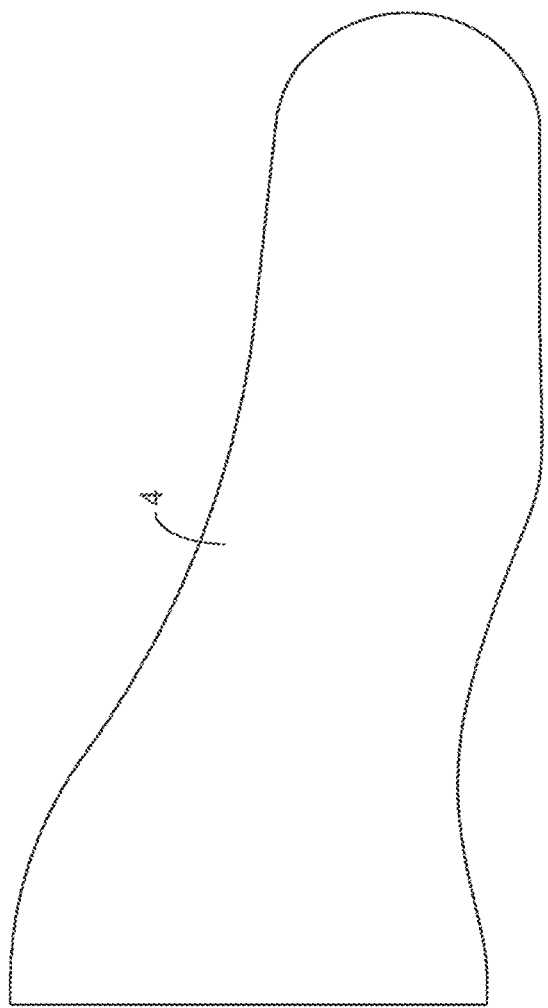
FIGS. 5A, 5B, and 5C depict one of several wings 4 (e.g. mesh wings from front and side perspectives, respectively), which are next in the exploded view (see FIG. 2) of the lumbar support device of FIGS. 1A-2.
Figure 5B:
Figure 5C:
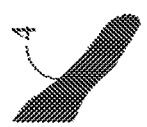

A mesh wing 4 is shown in FIGS. 5A and 5B. The present devices include several mesh wings 4, including e.g., two on each side of the device. The mesh wings 4 may be configured essentially in size and shape to match the padding 2 and/or layer 1 of the padding and wings.

The wings are also configured to receive a rib or boning material between a set of corresponding wings on each of the left and right sides of the device. That is, as shown in the exploded view (FIG. 2), the right side of the device may have a set of layers as follows: wing 4, ribs 5, wing 4, to form a right wing assembly; and the left side of the device may have a set of layers as follows: wing 4, ribs 5, wing 4, to form a left wing assembly.

FIGS. 6A and 6B depict one of the wings 4 with multiple ribs 5 thereon without the corresponding second wing 4 over the top. The ribs may be for example essentially orthogonal with respect to the length of the wings 4 (as shown in FIG. 6A), or the ribs may be in another configuration that is suitable for providing the desired support. By way of non-limiting example, the ribs may be substantially parallel to one another (as shown in FIG. 6A), or they may be in different angles with respect to one another, and they may optionally cross one another.

The present devices include arms that emerge from slit in the wings, which are held together and made adjustable through use of a corset pulley system assembly (or sub-assembly) to which the arms are connected. A user may pull the arms for attachment over or around their belly and the arms and corset assembly provide elasticity and tension such that when the arms are attached to one another, the device provides adequate support to the user.

A non-limiting example of the corset pulley assembly (or sub-assembly) enclosed within the overall support device of the present invention, examples of which are depicted e.g., in FIGS. 1 and 2, is depicted in FIG. 7A. The corset assembly includes, inter alia, multiple pieces of corset fabric 22, which may be formed for example, in an overlapping "V" formation, but other formations or configurations are contemplated. The corset assembly may also include clips 21 or other fasteners for connecting arms and enabling tightening and securing of the arms upon use of the device. The corset assembly may also include and corset bones 25 on either side of the corset assembly. The clips may be formed for example of a plastic or metal, but may be any suitable material. Similarly, the corset bones 25 may be formed from any suitable material that may assist in maintaining the shape, rigidity and support of the corset assembly such as rigilene boning. The clips may be other than the configurations shown, so long as they achieve the goal of attaching the arms in an adjustable fashion.

Figure 8B:
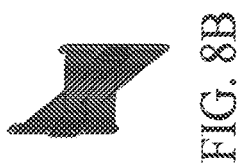
FIG. 8B depicts a perspective view of the example corset assembly.
Figure 8A:
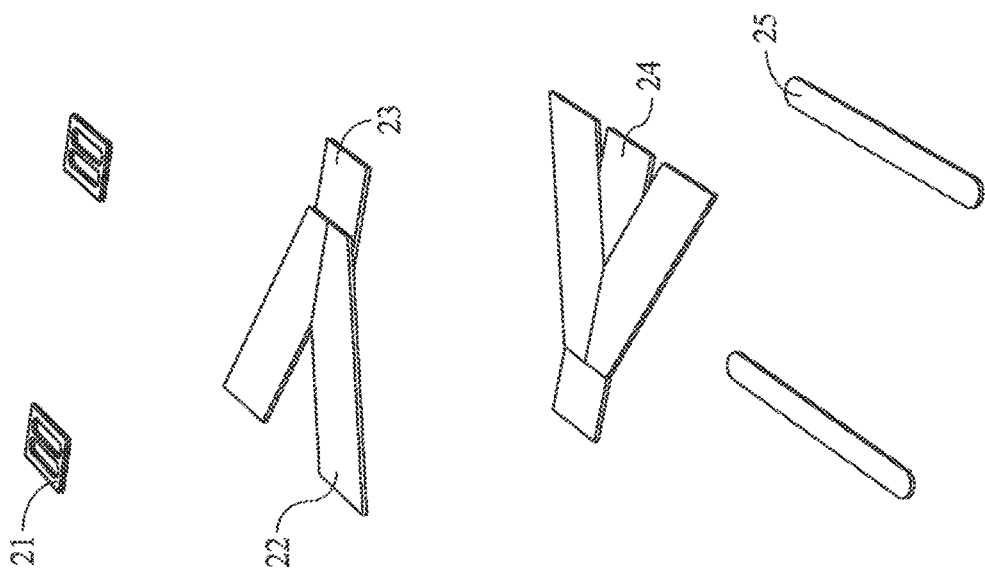
FIG. 8A further depicts the corset pulley system assembly as shown in FIGS. 7A-7C and other FIGS. herein in an exploded view.
Figure 9B:
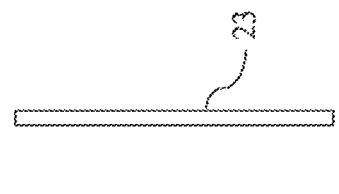
FIGS. 9A and 9B depict a front and a side view of a corset fabric 23 of a corset assembly according to inter alia, FIG. 8A.
Figure 9C:
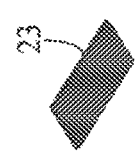
FIG. 9C depicts a perspective view of the example corset fabric 23.
Figure 9A:
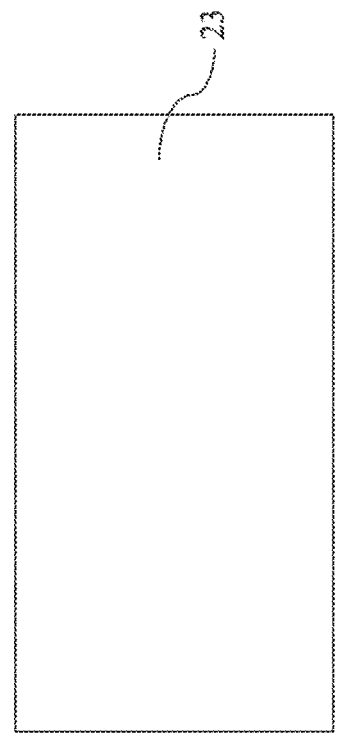

The corset pulley system assembly of FIG. 7A is further shown in FIG. 8 in an exploded view. As depicted in FIG. 8A, the corset assembly may have multiple pieces of fabric 22, 23, and 24 which overlap with one another. The fabric may be formed e.g., of elastic band or other elastomeric or stretch material. The elastic fabrics may be formed for example, into two fabric structures that overlap with one another as depicted. The clips may be configured so that they may attach the corset assembly to the arms. The boning is configured in size shape and placement for support. The fabric structures may include for example two diagonal fabric pieces each to form a "V" shape, and a second fabric piece (23 and 24) to further support holding the corset assembly together and provide further support when the device is in use. Corset fabrics 23 and 24 of a corset assembly according to FIG. 8 are shown in FIGS. 9A and 10A. FIG. 11A shows a diagonal corset fabric portion of a corset assembly according to inter alia, FIG. 8A. According to non-limiting embodiments, two such diagonal portions 22 along with a second corset fabric (23 or 24) form the two fabric structures which overlap with one another in the corset assembly of the present devices. According to alternative embodiments, one or more of the fabric pieces 22, or pieces 22 and 23, or pieces 22, and 24 may be formed from a single piece of fabric, rather than from separate pieces of fabric sewn or otherwise attached to one another.

Figure 12B:
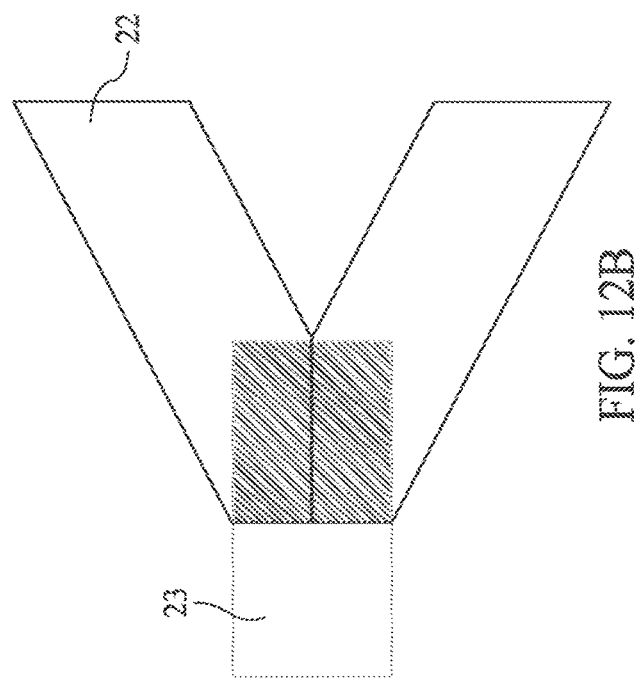
FIGS. 12A and 12B depict the corset assembly, and in particular, the stitching of fabrics together along the hatched area.
Figure 12A:
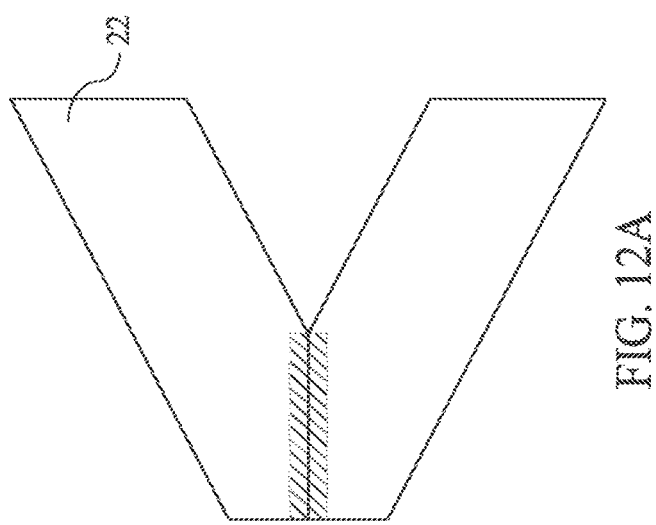

FIGS. 12A and 12B further depict one side of the corset assembly in accordance with non-limiting example embodiments, and in particular, the stitching of fabrics together along the hatched area. FIGS. 13A and 13B further depict the other side of the corset assembly in accordance with non-limiting example embodiments, and in particular, the stitching of fabrics together along the hatched area.

Figures 14A, 14B, 14C:
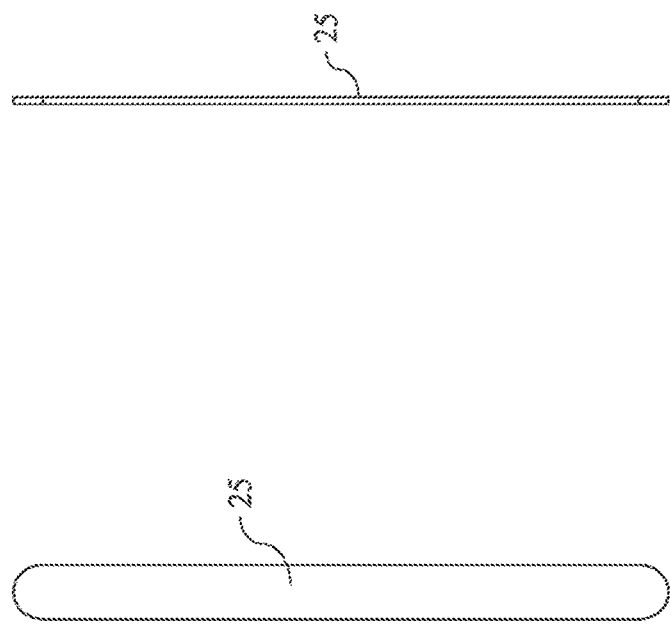
FIGS. 14A and 14B depict a front and a side view of a corset bone of a corset assembly according to inter alia, FIG. 8A.
FIG. 14C depicts a perspective view of the example corset bone 25.

FIGS. 14A and 14B depict a corset bone of a corset assembly according to inter alia, FIG. 8A. As indicated above, the corset bone may be on either side. As indicated above, the correct bone may be on either side of the corset assembly 6, and may be made of e.g., rigilene boning.

FIGS. 15A-15C depict views of a clip of a corset assembly according to inter alia, FIG. 8A.

FIG. 16A depicts a front perspective exploded view of a wing assembly according to non-limiting embodiments of the lumbar device of FIGS. 1A and 2. In particular, FIG. 16 depicts first and second wings 8, which include slits adapted in size and shape for the first and second arms to pass through respective slits. The slits may be reinforced e.g., with slit bones on an underside of the slits. FIG. 16A also shows that the first and second wings may be attached by one or more fabric portions 10. According to the non-limiting example depicted in FIG. 14, the wings 8 are attached with a cotton center fabric 10 One or multiple pieces of fabric may be present and the device is not limited to the depicted configuration. The wings 8 may be made e.g., of fleece, for comfort, although other materials are certainly contemplated and are included herein.

Figure 18C:
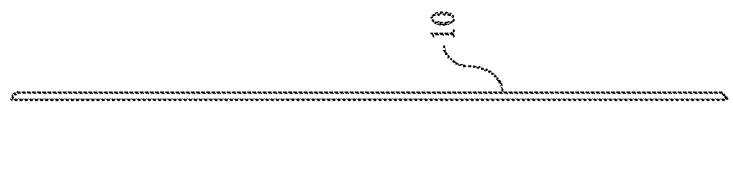
FIGS. 18A, 18B and 18C depict a piece of center fabric 10, from front, top and side views, respectively, arranged between the wings 8 as shown in FIG. 16A.
Figure 18D:
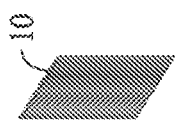
FIG. 18D depicts a perspective view of the example center fabric 10.
Figure 18A:
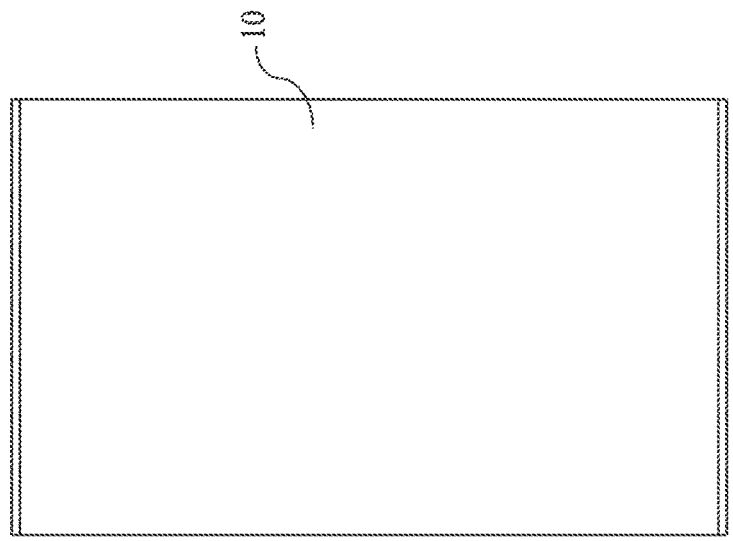
Figure 18B:

One of the wings 8 from e.g. FIG. 16 is depicted in FIG. 17A, which shows the slits through which a respective arm may pass. FIG. 18A depicts a piece of fabric 10, which is a piece of fabric between the wings 8. Multiple pieces of fabric 10 may be used. This fabric may be made e.g. of cotton.

Figure 19D:
FIG. 19D depicts a perspective view of the example slit bone 7.
Figure 19C:
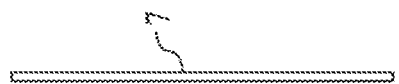
FIGS. 19A, 19B and 19C depict a slit bone 7 from FIG. 16A, arranged from front, top and side views, respectively.
Figure 19A:
Figure 19B:
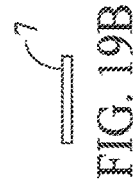

FIG. 19A depicts a slit bone 7, which may be made e.g. of rigilene boning or other suitable material.

The arms of the present devices may be formed from many different layers, as shown e.g., in the exploded view of FIG. 20. By way of non-limiting example, arms of the present devices may include for example, one or more cotton arms 11, one or more arm padding 12 layers, one or more a mesh arm layers 13, arm bones 14 and 15, an arm strap 16, which may be elastic, a fleece arm 17 and (or other fastener). One or more cotton layers 11, one or more padding layers 12, one or more mesh arm layers 13 (two layers are shown), arm bones or boning layer (14 and 15) and an elastic arm strap 16.

As explained herein, the arm attachment 18 (which is a hook and loop fastener depicted in FIG. 20), may be substituted by any removable or detachable attachment for fabric known to those skilled in the art. The arms 17 may be attachable to each other when the support device is in use, by an attachment on one or both of the arms 17, including but not limited to a clip, snap, hook, hook and loop fastener and/or zipper. In the case of hook and loop fasteners, the hook and loop fastener may be attached to one or both of the arms 17, as the material. In example embodiments, a hook portion of hook and loop fastener is attached (e.g. sewn or glued) near the end of one of the arms, and a loop portion of hook and loop fastener is attached near the end of the other arm 17. The precise location, size, and shape of such fasteners is not critical to an understanding of the invention.

It is also possible that only one arm has hook and loop fastener attached thereto (the hook portion), if the arms 17 are made of a material to which the hook portion would attach upon contact therewith.

Although labeled number 17 in e.g., FIGS. 1 and 2, the arms include multiple layers (e.g., 11-17) and components such as those set forth in the exploded view of FIGS. 2 and 20.

The arms include an outer layer 17, which may be made e.g. of fleece. Those skilled in the art would recognize that different materials may be used for each of the layers. For example, the cotton layers and padding may be replaced with other suitable materials, which preferably may provide comfort, cushioning, breathability and/or other advantageous features, as would be apparent to those skilled in the art.

FIG. 23C depicts an elastic arm strap 16, which is a component of each arm. The arm strap is a component for comfort and safety of the user, as it prevents the user from over-tightening the strap and device as a whole—which is of particular concern in maternity use of the device. The present devices should not be over-tightened to the extent where it becomes uncomfortable and/or restrictive.

Figure 24A:
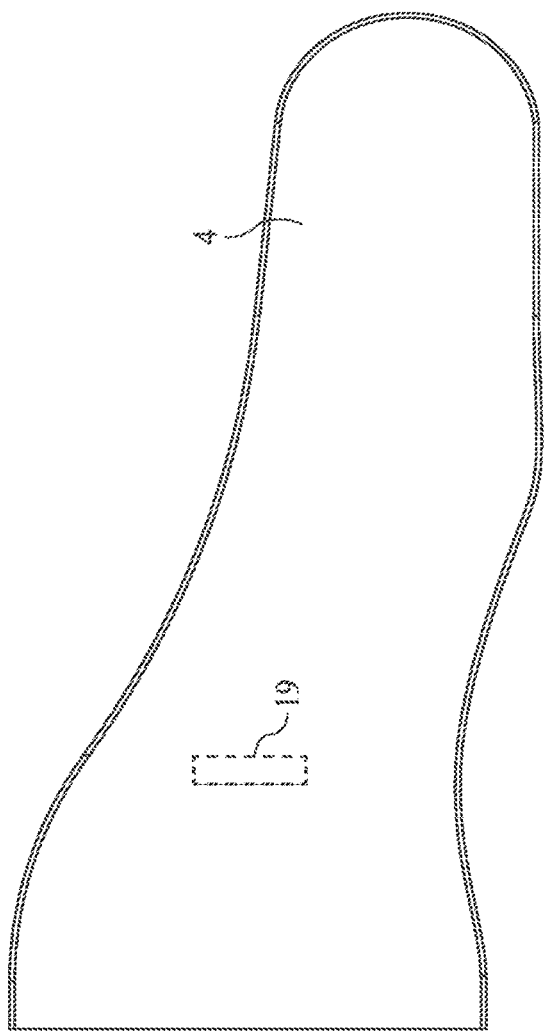
FIG. 24A depicts an example wing 4 configured for assembly. In particular, it is configured such that the arm strap 16 (not shown) must be pulled through the transparent square prior to sewing it to the hatched area on the diagram. The square and slit is transparent and located in the center of the wing 4 for reference. This connects the arm strap when one is building the brace.
Figure 24B:
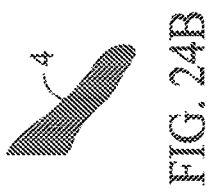
FIG. 24B depicts a perspective view of the example arm strap with blue wing assembly.

FIG. 24A depicts an example wing 4 configured for assembly. In particular, it is configured such that the arm strap 16 (not shown) must be pulled through the transparent "blue square" prior to sewing it to the hatched area on the diagram. The "blue" square and slit is transparent and located in the center of the wing 4 for reference. This connects the arm strap when one is building the brace). FIG. 24A details embodiments of how to assemble the arm when fabricating the brace, i.e., that it is necessary to pull the arm through the blue square slit hole prior to sewing it, because once it is sewed in, it will be impossible to get the arm through. FIG. 24B depicts a perspective view of the example arm strap with blue wing assembly.

The arm may have multiple bones as depicted forth for example, in FIGS. 25A-27C. FIGS. 25A-D show a first example bone 14. FIGS. 26A-D show a second example bone 15. FIGS. 27A-D show an example of relative placement of such bones with respect to a mesh arm 13.

The boning layers(s) may be made e.g., of rigilene boning, metal, plastic or other material that may provide the required support and rigidity and shape keeping features. The mesh layer is for breathing and may include any suitable type of mesh known in the art. Other breathable materials are contemplated however as well.

FIG. 28A depicts arm attachment portions 18 (or "arm fasteners"), which may attach one arm to the other arm to secure the arms around, over and/or under the belly of a user. Although the arm attachment 18 is depicted as a hook and loop fastener in a somewhat semi-circular shape, (e.g., in FIGS. 2, 19, and 28A), other attachments and/or shapes are contemplated and may be used. The essentially semi-circular shape was selected for the depicted embodiment to roughly correspond to the ends of the arms for secure attachment of the first and second arms to one another. The fastener may be attached to the arms, e.g., by sewing or adhesive or other attachment, which may be permanent or semi-permanent. In particular, according to non-limiting example embodiments, a hook portion of hook and loop fastener may be attached to a front or back of one end of a first arm, and a loop portion of the hook and loop fastener may be attached to the opposite side (front or back) of the second arm, such that when one puts the brace on, and pulls the arms around a desired position with respect to the user's belly, one arm overlaps the other and the hook and loop portions at least partially overlap for attachment to one another upon contact, thus securing the arms over a desired portion of a user's belly.

FIG. 21A depicts wing fastener portions 3, (or "wing fasteners") which may attach one wing to the other wing to secure the wings around, over or under the belly in a desired position. Although the wing fastener 3 is depicted as a hook and loop fastener in a somewhat semi-circular shape, (e.g., in FIG. 2), other attachments and/or shapes are contemplated and may be used. The essentially semi-circular shape was selected for the depicted embodiment to roughly correspond to the ends of the wings for secure attachment of the first and second wings to one another. The fastener may be attached to the wings, e.g., by sewing or adhesive or other fastening device, which may be permanent or semi-permanent. In particular, according to non-limiting example embodiments, a hook portion of hook and loop fastener may be attached to a front or back of one end of a wing, and the loop portion of hook and loop fastener may be attached to the opposite side (front or back) of the second wing, such that when one puts the brace on, and pulls the wings around a desired portion of their belly, one wing overlaps the other and the hook and loop portions at least partially overlap for attachment to one another upon contact, thus securing the wings over a desired portion of a user's belly.

By way of non-limiting example, the "female" portion of a hook and loop fastener may be attached to an underside of a right wing and/or right arm and the "male" portion of a hook and loop fastener may be attached to a top side of the left wing and/or left arm that when the straps are folded across a wearer, the "male" and "female" portions come into contact with one another and secure the straps in a desired place/fit. It should be understood however, that the fasteners may be varied and that when hook and loop fasteners are used, the fasteners may be reversed (e.g., "male" on the underside of the wing and "female" on the top of the wing, etc.)

In one or more layers of the device, the first and second wings may be a continuous piece of fabric (see e.g. layers 1 and 2). Other layers of the wings may have the first and second wings formed separately and connected to one another (see e.g. wings 4—mesh) and 8 (fleece). It is contemplated that the first and second arms may include one or more portions or layers that are a continuous material and may contain layers that are separate from one another, e.g., the separate mesh arms and bones. During assembly of the device multiple layers may be pre-attached to one another. The layers depicted e.g., in FIG. 2 do not need to be attached in the order shown. For example, one may assemble e.g, the straps, corset pulley system assembly and/or wing/rib assembly separately, before assembling the entire device.

The present devices may also include at least one panel fastener configured for attachment of at least one padded panel to the device. According to non-limiting example embodiments, a panel fastener may include e.g., one side (e.g., loop) of a hook and loop fastener.

The lumber support devices themselves may further include at least one padded panel selected from an anterior panel, a posterior panel and a coronal panel. The panel may be detachable or removable.

The at least one removable padded panel may be attached to the device by at least one panel fastener. That is, the panel may have e.g., an opposite portion of a hook and loop fastener from a portion included on the main portion of the device.

According to example embodiments, the at least one panel may be configured with an opening to attach the panel to the device by sliding the panel onto the device. Thus, the panel may have e.g., loops or straps.

FIGS. 29-34, 41-42, 44-46B, 48A and 48B depict non-limiting examples of optional, removable padded, but rigid anterior, posterior and coronal panels, which may be added or removed from the present devices by a user. FIGS. 77-78 and 81 also depict example panels in accordance with non-limiting example embodiments. As indicated in FIG. 78, the posterior panel may be place on an inner posterior aspect of the main brace and attached, e.g. using VELCRO. In particular, one or more panels may be desired for use in a post-natal kit, or in non-pregnancy uses. Under a doctor's supervision, one or more panels may be used during early pregnancy, but in no event should the attachable panels be used during late stages of pregnancy.

FIG. 29 depicts a front view of a removable padded posterior panel 26 in accordance with non-limiting example embodiments. As shown in FIG. 29, the edges 27 may be padded with e.g., soft foamy plastic. The front 28 may be added with foam to soften over hard plastic. Additionally, the posterior panel may have multiple holes 29 to allow breathability of the panel. Example embodiments of the panel may be configured such that the top of the panel reaches e.g. the T9 vertebrae (To comply with brace codes L0631 and L0637).

L0631 provides as follows: HCPCS Code Description: Lumbar-sacral orthosis, sagittal control, with rigid anterior and posterior panels, posterior extends from sacrococcygeal junction to t-9 vertebra, produces intracavitary pressure to reduce load on the intervertebral discs, includes straps, closures, may include padding, shoulder straps, pendulous abdomen design, prefabricated item that has been trimmed, bent, molded, assembled, or otherwise customized to fit a specific patient by an individual with expertise HCPCS Code: L0631.

L0637 provides lumbar-sacral orthosis, sagittal-coronal control, with rigid anterior and posterior frame/panels, posterior extends from sacrococcygeal junction to t-9 vertebra, lateral strength provided by rigid lateral frame/panels, produces intracavitary pressure to reduce load on intervertebral discs, includes straps.

The present device is designed to fit the contours of the body, comfortably resting on the back and abdomen. The present device is designed to provide bi-modal orthotic support. The main brace is intended for gestational use and offers support across the T9-sacroiliac junction cord span. The main brace and panels are intended for post-natal use, offering great support to the spine's curvature.

FIG. 30 depicts a back view of the removable padded posterior panel of FIG. 29. As depicted in FIG. 30, the back of the posterior panel may include hook and loop fastener with a removable sleeve (e.g., cloth) configured for the brace to pass through. The posterior panel may be designed e.g., to extend from T9-S1 on the patient. Addition of anterior and posterior panels will advantageously meet the guidelines for L0631 brace code. Posterior panel can also be combined with removable side flanges to enable circumferential coronal and sagittal support and will then meet the guidelines for L0637 brace code used in the USA. Panels can attach e.g., via hook and loop fastener strips and/ or hook and loop fastener strip 30 with cloth sleeve 31. According to example embodiments, panels will strictly be used post-partum or in very early pregnancy before any "belly" develops. The posterior panel will have a pillow-like padding covered in cloth on its anterior side as this will rest against the patients' lumbar region from T9-S1.

FIG. 31 depicts a front view of a removable coronal side panel (front 32) in accordance with non-limiting example embodiments. FIG. 31 also depicts a smooth cloth layer between the hook and loop fastener attachments 37.

FIG. 32 depicts a back view of the removable coronal side panel of FIG. 31. Coronal Panels (back 31) may have rigid plastic 33 covered with significant extra pillow like padding 34 for comfort. The edges 36 will also have foam like plastic covering and padded edges for comfort. The coronal panels will attach to the anterior aspect of the large Posterior T9-S1 panel. The attachment may be e.g., via hook and loop fastener 39, which faces the posterior.

FIG. 33 depicts a front view of a removable anterior panel 40 in accordance with non-limiting example embodiments. The panel in FIG. 33 has padded edges 43, removable hook and loop fastener 41 to attach to the brace, and is made of plastic 42 covered in breathable cloth.

FIG. 34 depicts a back view of the removable anterior panel of FIG. 33. The Anterior panels may have removable hook and loop fastener attachments 41 to the brace itself or can attach via a hook and loop fastener cloth Sleeve. The anterior panel may have a pillow-like padding covered in cloth. This will face posteriorly as it will rest against the abdomen. The anterior panels have padded edges 43 and extra padding 44.

FIGS. 41-42 and 44-46 depict panels of padding in accordance with non-limiting example embodiments of the present invention.

FIGS. 77-78 and 81 also depict non-limiting examples of panels, including e.g. an anterior panel in accordance with embodiments of the present invention.

As discussed herein, additional padding and/or supports may be added to the support devices of the present application. By way of non-limiting example, removable padded panels may be added to the back of the device, e.g., posterior panels as shown in FIGS. 41 and 46, or the front (belly) portions of the device, e.g., anterior panels as shown in FIGS. 42 and 44-45, which may be removably attached to the device, e.g., by attachments, which may include e.g., one or more of the following: VELCRO®, clips, snaps, straps or other connector that permits removal of the padding. Thus, example embodiments further include one or more attachments. Further example embodiments include one or more padded panels.

When brace add-ons, such as panels are used, certain safety precautions should be adhered to. By way of non-limiting example, one or more of the following safety precautions may be advised. 1) Panels should only be used under the advisement and adjustment of a medical professional, typically the prescribing Practitioner; 2) Panels should always be used at the prescriber's recommendations; 3) The anterior panel should never be placed directly on an unhealed C-section wound in a Post-natal patient; 4) The anterior panel should never be used during pregnancy (Especially the later trimesters 2.sup.nd and 3.sup.rd) without being custom fit by the physician/Orthotist, IF USED DURING PREGNANCY THE ANTERIOR PANEL MUST NOT BE PLACED UNDER THE MAIN ARMS; 5) The panels are rigid, and the physician should be immediately notified if there are any increased pressure points or uncomfortable areas from the brace/panels: The brace should also be immediately discontinued until reevaluation by physician or medical professional; 6) Never wear any back brace in bed when at rest lying down; 7) The brace panels should never be HEATED WITH THE PADDING ON NOR HEATED ON THE SIDE WHERE THE HOOK AND LOOP FASTENER IS ATTACHED TO. This will damage the brace; 8) The brace panels should never be placed in a dryer after washing because it will damage it. These and any other safety precautions deemed advisable. May be included e.g. on or with the present devices, such as in example kits herein.

The present devices are advantageous in that they are the only known maternity braces that can be used throughout an entire pregnancy AND post-partum, because of the modular nature of the device, and use of padded, but rigid, anterior, posterior, and/or coronal panels. The present devices also have a unique pulley system that has a unique pulley system with over-tensioning protection. In particular, the elastic in the tightening arms provides over-tensioning protection and also the arms to be positioned in multiple configurations on the pregnant belly. The present devices are the only devices that can be used throughout pregnancy as an LSO and also function as a traditional LSO post-natal. The present built-in safety mechanisms, specialized pulley systems, and the ability to attach the anterior panel to the adjustment arm allow for this.

As indicated herein, optional anterior, posterior, and/or coronal panels may be included with, or added to the present devices. This is the only brace that is so modular that it can be used throughout the entire pregnancy and post-partum. The combination of the unique pulley/elastic, over-tensioning prevention system, the adjustable arms, and the extra padded rigid anterior, posterior and/or coronal panels allow for this modularity.

The present devices are the only devices that take into consideration post-partum back pain in C-section patients. The c-section incision cuts through the lower abdominal muscles significantly weakening the patients' core muscles and leading to back pain after delivery. The anterior and posterior panels will reduce back stress and take undue pressure off of the healing muscles which take 6-12 weeks post C-section to heal. The brace is designed to help through all stages of pregnancy and after delivery as well for both C-section patents and vaginal delivery patients.

These are also the only braces that take into consideration post-partum back pain in non C-section patients. In pregnant women that have a vaginal delivery: the lower abdominal muscles are stretched and significantly weakened. This takes weeks to a few months to improve. The patient's core muscles are subsequently weaker and this can lead to back pain after delivery. The anterior and posterior panels will reduce back stress and take undue pressure off of the healing muscles which take weeks to months to heal. Thus, the present devices are That is, the brace is designed to help through all stages of pregnancy and after delivery as well, for both C-section patient and vaginal delivery patients. The anterior panel is designed and specifically pillow padding will prevent excess pressure on the c-section scar. The brace panels should not be used until the wounds are completely healed.

The present device is designed to fit comfortably, with several adjustable settings to give you optimal levels of support and comfort.

The optional padded panels allow for reduction in back stresses of the present devices in pregnancy and post-partum by using a unique pulley and tensioning system of the present devices and removable panels. All other braces on the market focus on reducing belly stress after the pregnant woman gained weight. The optional padded panels must be used under the guidance of a medical professional and customized for appropriate fit. If used during pregnancy, due to the belly shape changes the panels (especially anterior) must continually be readjusted and molded (under guidance of medical professional) as growth occurs to maximize brace effectiveness.

The panels may include e.g., a padded posterior panel that may be primarily used in very early pregnancy until the pregnant woman forms a belly and also post-partum. The posterior panel(s) are not limited by its material. According to non-limiting example embodiments the posterior panel(s) are rigid, but made of a material that will conform to the lumbar region of the person to whom the device is to be applied. Example panels may include one or more materials, such as cloth material, which may be lightweight for comfort and/or one more stiffer or reinforced materials for added stability. Example support materials that may be included for example in the posterior panel may include inner light weight (cloth) with outer-laced mesh to maximize comfort and breathability while at the same time maintaining support. The posterior panel(s) may in some embodiments include an elastic fiber strands within the material which allow for a form fit with tensioning. A central region of a panel may be made of a breathable cloth fabric to interconnect for example elastic spandex/elastic flexible regions.

The posterior panels may include e.g., curved portions, angles, and/or any other desired shape that achieves the desired results and is not limited to the shape(s) depicted herein. Additionally, the size of the posterior panels may be determined based on various factors including for example the size of the intended user of the device. For example, as indicated above, devices of the present invention may be formed into sizes such as Small, Medium, Large and Extra large, or into numerical sizes, which may call for a different size back panels.

Example anterior panels may be constructed of any desirable material and/or shape depending on the intended use of the device. For example, a front/anterior panel may be of a shape, size and material to be able to cover an expanding pregnancy belly, including Lycra. When the anterior panel is used in pregnancy it should only be placed between the adjustment arms and the main brace arms and always needs to be custom molded by a medical professional. When used post-natal, the anterior panel can be used under the main brace arms as with a typical LSO. An anterior panel should only be used very early in pregnancy within the first few weeks but mainly post-partum. The front panel may also include one or more moveable and/or removable portions, such that a wearer of the device may for example gather the panel under or over the wearer's belly, or remove the panel or a portion thereof from the device (e.g., on hot days or to help conform the device to the woman's belly as it grows larger, or depending on wardrobe considerations). A non-limiting example of an anterior panel which may be added to or included with the present devices, is depicted e.g. in FIGS. 42, 44 and 45. According to example embodiments, an anterior panel is fastened to the arms via a hook and loop fastener attachment between wing arms and a body of the device.

The posterior panel may be e.g., in a substantially rectangular shape. The posterior panel may include curved portions, angles, and/or any other desired shape that achieves the desired results. Additionally, the size of the posterior panel may be determined based on various factors including for example the size of the intended user of the device. For example, as indicated above, devices of the present invention may be formed into sizes such as Extra-Small, Small, Medium, Large, Extra large, or Extra extra large (as shown e.g., in FIG. 43), or into numerical sizes, which may call for different size panels corresponding thereto.

FIG. 47 depicts an example support device/brace in use on an individual, which has coronal panels inserted (slid in) on both sides. Non-limiting examples of such coronal support devices are depicted in FIGS. 48A and 48B. As depicted in FIGS. 47 and 48A and 48B, the coronal panels may be inserted on one or both sides. They may include slits to provide air flow. Additionally, the panels may be covered and padded similarly to other panels. The outside may not be padded in certain embodiments. The coronal panels may be made of similar plastic or other materials as the other panels and may be moldable. The coronal panels may be configured for example, such that the device complies with L0637.

Example panels may be constructed of any desirable material and/or shape depending on the intended use of the device. According to example embodiments, anterior, posterior and coronal panels will be rigid but well padded (e.g., with pillow like material covered in mesh cloth), and have multiple holes in the plastic to provide breathability. The front panel may also include one or more moveable and/or removable portions, such that a wearer of the device may for example gather the panel under or over the wearer's belly, or remove the panel or a portion thereof from the device (e.g., on hot days or to help conform the device to the woman's belly as it grows larger, or depending on wardrobe considerations).

These present devices are modular: allowing the different components such as the panels described herein, to be added or subtracted as a persons' size changes, e.g., to better conform to a women's anatomic changes throughout pregnancy. One of the major concerns with other braces and back supports is that over tensioning can create excess pressure on the abdomen of the pregnant female. The present braces combine multiple safeguards to prevent this (over tensioning) while at the same time providing more contouring support by conforming to the anatomy throughout the changes a female has in each trimester pregnancy.

A goal of the present supports is to provide stabilization throughout each trimester of pregnancy. Initially, during the course of a woman's pregnancy, the corset (e.g., spandex or elastic material) component alone (without the straps attached) may be used during the first and possibly early second trimester, as the straps are typically not necessary to support the belly (which is usually not present into the second and third trimesters). However, as the belly grows throughout the second and third trimester of pregnancy, the arms can be used in a higher position for example in the last days of pregnancy to avoid the brace from sliding off.

Also provided herein are methods of preventing or treating back pain in a person (such as a pregnant, human female or other person who may benefit from support provided by wearing the device) that include applying the devices described herein to a person, such that the person may wear the device. Examples of such devices may include e.g., the devices described herein.

The present methods of preventing or treating back pain in a person, include applying the present lumbar support devices to a person, and securing the device to the person by fastening the wings to one another and then fastening the arms to one another around the user's belly.

The device may be configured such that the fastened arm position with respect to a person to whom the device is applied, is variable.

For example, the arms may be positioned with respect to the person such that the arms are fastened to one another so as to rest at least partially over the fastened wings.

According to other embodiments, the arms may be positioned with respect to the person such that the arms are fastened to one another so as to rest on the upper abdominal belly.

FIGS. 35-40 depict drawings of example embodiments of a device according to the present invention and depict the devices in use by various users, in accordance with non-limiting examples.

FIG. 35 depicts a close up view of a portion of a lumbar support device in accordance with non-limiting example embodiments. In particular, this close up view depicts an arm emerging from a slit in a wing of the support device.

FIG. 36 depicts a drawing of one side of a lumbar support device in accordance with non-limiting example embodiments of the present invention. As shown in FIG. 36, an arm emerges from a slit in the corresponding wing.

FIG. 37 depicts a drawing of a middle portion of an underside of the lumbar support device in accordance with non-limiting example embodiments.

FIG. 38 depicts a device in accordance with the present invention in use as applied to a pregnant user. In the depicted embodiment, the wings are first applied over the belly and attached to each other by hook and loop fastener. The arms are applied and positioned at least partly over the wings and attached to one another, also by hook and loop fastener.

FIG. 39 depicts a device in accordance with the present invention in use as applied to a different pregnant user than in FIG. 38. In this embodiment, the wings are applied toward the bottom of the belly and attached to one another and the arms are positioned over the top of the belly and attached to each other in that position. The arms may be positioned over the belly, e.g., during late pregnancy. Positioning the device such that the arms rest upon the upper belly provides additional support and prevents the brace from slipping under the belly too far.

FIG. 40 depicts a device in accordance with the present invention in use as applied to a pregnant user. In the depicted embodiment, the wings are first applied over the belly and attached to one another, and the arms are applied and positioned at least somewhat over the wings and attached to one another.

The adjustability of the present support devices maximizes the support's effectiveness because it is form fitted to the rapidly changing anatomy caused by pregnancy. Ultimately, this decreases the stresses on the spine, improving posture/alignment during activities of daily living.

According to example embodiments, the devices may be applied to a person either by the person themselves or with the assistance of another person. The devices may be applied by a method that includes positioning the device on the person such that a posterior panel(s) (when used) or middle portion of the wings is positioned across a back of the person. Securing the lumber support device to the individual includes positioning and attaching the wings over the abdomen of the individual and fastening the wings to one another, and positioning and attaching arms having an elastomeric corset assembly, together across, over or under the belly to a desired position and tension. In example embodiments, the arms are positioned and attached before the wings are positioned and attached.

Such positioning may include for example, wings of the device overlapping the wings and attaching them to one another around the waist of the user. The wings may be attachable e.g., with buttons, zipper, hook and eye, snaps, hook and loop, or another fastener. If a front panel is present, the front panel may be adjusted, e.g. by moving the panel to a preferred position. Once positioned correctly, one may close the wings over the abdomen of the wearer.

The present methods may also include pulling the arms of the device from their positions through slits in the wings until they are at a desired length to be positioned around, over, or under the belly and then attaching the arms to one another.

By way of non-limiting example, the device may be applied to a wearer by a method comprising positioning the device on the person such that a posterior portion of a brace is across a back of the user; positioning and attaching wings over the abdomen of the person, and positioning and attaching arms having an elastomeric corset assembly, together across, over or under the belly to a desired position and tension.

In non-limiting example embodiments, it may be advantageous to close and position the arms before closing and positioning the wings.

According to non-limiting examples, when one or more panels are used, the side of the panels with the attachment mechanism (e.g. hook and loop fastener) should be attached to the brace. The large back panel, an example of which is depicted in FIG. 46, can be directly attached to an inner midline portion of the brace (e.g. at fabric portion 10) of the brace. Front panels may optionally be attached to the brace device in one or both of two positions. It can be attached directly to an inner side of the main support straps/arms. It can also be attached to an inner side of the adjustable arms/wings after the main straps are fastened. In this position, the front panel will be between the adjustable arms and the wings/straps. This is a unique feature of the present brace, which allows the anterior panels use in the pregnancy with custom molding to conform to the belly. This allows adjustability in pregnancy, because placing the rigid panel under the main arms in a patient in later stages of pregnancy would be very uncomfortable and could cause pressure/sores/issues. The anterior panel between the adjustable arms and the main brace arms allows for more rigid support, reducing pressure produced if the anterior panel was placed under the main brace arm, as with a typical LSO. Optional front panels may be attached (e.g. using suitable attachment mechanisms such as a hook and loop fastener) to the inner side (e.g. toward the wearer of the device) of support straps or the inner side (toward the wearer of the device) of the adjustable arms/wings. The term "main support straps" refers to primary support straps of the present invention, i.e., the arms. This positioning of a panel should not need to be depicted to be understood. It is straightforward and one skilled in the art can easily envision such placement.

Once appropriately adjusted, the support device will function to pull in the lumbar vertebrae, increasing lordosis and placing the center of gravity in a more natural position.

Example embodiments provided herein are further directed to kits that may include at least one lumbar support device provided herein and instructions for use of the device. The present kits may optionally include instructions for proper application and/or adjustment of the lumbar support device. Kits may also include e.g., one or more removable padded panels, e.g. for post-partum or other non-pregnancy uses, and/or an extender or other accessory described herein.

Such instructions may include for example instructions regarding proper positioning and application of the device on a person and/or methods of adjusting the device to achieve a proper fit. Example instructions may provide guidance with respect to when and how long to wear the device to achieve the best results. Further example instructions may provide instructions regarding visiting a physician when necessary and/or exercises the user may perform even when not wearing the device to improve muscle stability, help strengthen core and/or back muscles and help prevent and/or lessen back pain by methods in addition to wearing the device. Further example instructions may include instructions for cleaning the device. The form of suitable "instructions" included in packaging/kits for any product, are well known in the art. The content of such instructions may be determined e.g. based on the present specification and based on medical knowledge by those skilled in the art. The shape, size form may be e.g. a sheet of paper or booklet or tag or of any other suitable form. Depiction of e.g., a booklet or sheet of paper next to the present braces is not be necessary to understand the invention.

Kits may also include devices according to present embodiments and one or more removable panels that may be attached to the device, as set forth herein.

Kits that include the present devices having electronics incorporated therein and/or thereon may also include software, software codes, a device or measuring or displaying or otherwise communicating data (such as the type of data discussed above), a cord for charging any electronics, and/or a device, such as a fitness tracker or smart phone for receiving data, alters or other communication.

The removable padded panel(s) may be selected from the group consisting of anterior, posterior and coronal panels.

In the present kits, the removable padded panels are preferably selected from panels that enable the brace to comply with L0631 & L0637 US brace codes.

After the wings are positioned over a person's abdomen and attached to one another by a fastener, then the wearer may further secure or adjust the device by adjusting the arms. The arms may be secured and adjusted for example by pulling on the respective arms e.g., anteriorly (toward the front), which pulls on the arms and corset, and therefore, tighten the arms over the front of the body to help it conform to the belly and back.

If the patient is really large a belt extender, as shown for example in FIGS. 66-67, may be used to make the larger size braces fit patients who are very large. An extender may be for example, an additional piece of modularity to allow it to conform to different size pregnant patients. Also, if the patient grows a lot during their pregnancy, the extender attachment works so the patient can continue to use the brace even if they grow out of the original size. As shown in FIGS. 66-67, the brace extender attachment may be attached by e.g. hook and loop fastener 54 to the main arms to increase the size and expand the present Device. The brace may then be closed in the standard way, the right arm may be closed over and attached by hook and loop fastener to the extender arm. This adds expansion to the brace and increased size for patients that grow out of the brace. By way of example, the extender may extend the brace seven inches, but the size may vary. A hook and loop fastener for example may be used to attach the extender to LEFT MAIN brace Arm to increase the size of the brace. The brace may then be closed in the standard way without the extender changing how the brace closes. The right arm is closed over and attached by hook and loop fastener to the extender arm.

In non-limiting examples, the extender may have the same or similar width as arms of the brace.

The present invention is further described by way of the following non-limiting example embodiments.

EXAMPLES

Example 1

A study was conducted to determine changes in the center of gravity and lift created by the present devices as compared to other devices. In particular, the study was performed to quantify changes in whole center of body mass with a surrogate pregnancy vest and gestational orthoses. The study also determined circumferential force distributions between the orthoses and patients' body, with specific emphasis on the anterior lift afforded by the braces. The gathered biomechanical data showed that the anterior lift of the present methods and device is greater than that achieved by other devices that do not act in the same way as the present invention. (See FIG. 82). The study shows that the present device significantly improves anterior lift versus other commonly used over the counter supports ($p<0.05$). In particular, FIG. 82 shows Contact Force Ratios—the ratio of anterior lift to posterior compression produced by four different gestational orthoses. The present device demonstrated a markedly higher anterior lift to posterior compression ratio compared to the other orthoses ($p<0.001$). In FIG. 82, the bar height indicates ratio value.

The data also showed that the posterior force resulting from the present methods and device was much lower than other devices. (See FIG. 83). The present device significantly reduces compression versus other braces ($p<0.05$).

FIG. 84 depicts results of the mean shift in center of gravity from baseline of the present device (with and without a posterior panel) as compared to other devices. The present device appears to restore CoG to the near normal condition, with and without posterior panel. Center of Gravity X-Y Plot—The calculated CoG data (mm translation) data is shown for each treatment group with comparison to the baseline data (0,0). The mean and standard deviation values are shown in parenthesis.

Example 2

According to a further non-limiting example embodiments, a retail version of the brace is provided as depicted for example, in FIGS. 85-90. FIG. 86 depicts an exploded view of these embodiments. FIG. 90 depicts a view of the corset assembly 111 portion of this embodiment of the brace, including corset pieces 112, clips 113, and corset bones 114. In the retail brace, the basic mechanism of the brace is similar to other embodiments discussed herein. However, the opening and pulley attachments may simplified and less expensive to make than the prescription version of the present brace. These figures depict a non-limiting example, particularly with respect to specific materials and measurements. These figures show brace components including corset assembly 111, arms, wings, etc of the present embodiments. These embodiments differ from other example embodiments, e.g. with respect to the slits 103 being larger/longer than in other embodiments and with regard to the arm/wing shape. By way of non-limiting example, in these embodiments, the slits may be 10%, 20% or 30% longer than the width of an arm emerging from the slit. But such embodiments are not limited to such sizes.

Example 3

According to a further non-limiting example embodiments, a smart version of the present device or Smart device is provided. In this embodiment, data obtained from biomechanical testing research is used to create a smart that will be used in conjunction with cellular phone app maximizing effectiveness. With the inventor's research the inventor used pressure sensors under the brace to calculate the amount of Newton force "lift" created by the present invention and competitor braces. The inventor was able to determine how varying adjustment arm tension, positions and addition of the panels modified the present invention's ability to produce lift (and in different ways). The inventor also was able to calculate the compression forces the present invention produced to create that lift.

This information can be used to calculate formulas and tables that can be used to recommend how to use the present braces' modularity/customizability to achieve the appropriate lift (and best results). These formulas and tables will be built into and used in conjunction with a cell phone App and Bluetooth pressure sensors under the brace while patients are using the present invention. A cellphone App will ask a series of questions to estimate that pregnant women's excess belly weight. You can estimate a women's truncal obesity caused from their excessive body weight gained during pregnancy. These formulas will be developed from their pre-pregnancy status; with their height, pre-pregnancy weight, current weight, waist to hip ratio (pre (if possible) and post pregnancy) belly circumference, fundal height, age, pre-pregnancy BMI, and current BMI. Once this information is entered the patients Truncal Body Mass Variation will be estimated. This will be used to calculate the recommended range of "lift" in Newtons of force "underbelly lift" required to counteract the negative impact of the belly weight (Truncal Body Mass Variation).

In example embodiments, the BLUETOOTH pressure sensors will be placed (hook and loop fastener attached) underneath the brace in specific locations. These pressure readings will be picked up by the cell phone app and patients will be able to "dial-in" the appropriate recommended lift to counteract their belly weight. All of this will be done to maximize the braces effectiveness therefore creating a smart device. In example embodiments, such as when the sensors are attached by hook and loop fastener, the sensors may be removable. This may be advantageous, e.g., in a case in which a sensor goes bad and a replacement is needed. The removability may also be advantageous e.g. for removal prior to washing the brace.

Further provided are systems that include at least one lumbar support device, which includes one or more electronic components incorporated therein and/or thereon. The electronics may include for example, electronics that are capable of detecting, monitoring, measuring and/or calculating one or more maternal and/or fetal vital signs. The electronic component may optionally have a method of recording, displaying, and/or communicating such vital signs (or data), for example to a computer or smart device, such as the cell phone or computer of a wearer of the device or person authorized by them (e.g., spouse or other family member, physician, etc). According to non-limiting example embodiments, systems may include one or more pressure sensors, which may optionally by removable from the present devices. According to other embodiments, the present systems may include one or more electronic components capable of adjusting the device, such as adjusting the fit, distance, force, lift, pressure or time worn.

According to example embodiments, the system may be configured to shift the center of gravity in a user of the device, to a desired center of gravity, which desired center of gravity is further toward a posterior side of the user, by a method including applying modifiable lifting forces to a lower abdomen of the user using a pully system, under the belly of the individual toward the desired center of gravity; and applying one or more vector forces from an anterior side of the user toward the desired center of gravity.

Here is how the process will work step by step: The present invention biomechanical research information/data was obtained from using surrogate pregnancy bellies and pressure sensors. Tables will be created based on the pressure sensors data from the research: this data yielded a plethora of proprietary information on how different configurations of the present invention (Customizations) effected the "lift" created. For example: by using the present invention posterior panel with the adjustment arms at maximum pull, the maximum and overall "lift" calculations yielded different results when compared to without the posterior panel. Baseline truncates body mass will be calculated using info. This data will be used to create tables that will ultimately recommend which patient specific configurations (Customizations) of the present invention to use.

The present invention customizations are patient specific and fitters can use to tables to better instruct patients improving the brace effectiveness at reducing back pain (See FIGS. 91 and 92). Fitters can optimize the present invention effectiveness at neutralizing the negative effects of belly weight by using the tables three settings: adjustment arm tension, adjustment arm position and panel use. -three suggested settings on adjustment arms; Minimal pull, medium pull, maximum pull (pull and at hook and loop fastener Velcro limit of overlap adjustment arms), three suggestions on adjustment arm positions: adjustment arms over main arms, Position at Umbilicus just above Main arms and Adjustment Arms on upper belly above main arms (Highest above Main arms), Panel Use: With/ Without Posterior Panel and with without Anterior panel, fitters will recommend above different brace modifications base on tables (See FIGS. 91 and 92), and teach patients who use the present invention how to more effectively obtain benefit from its use. As indicated in FIGS. 91 and 92, Newtons aren't necessarily the values that will be used, but the figures provide an example of how the brace fitters can use the information to better use the brace, maximizing its effectiveness.

A precision fit dial with elastic connections to the main/adjustment arms may also be used: Being able to vary the adjustment arm force transmission to the pulley complex without opening up the brace could be accomplished vis this change: However, this would make using end position of the adjustment arms to alter lift difficult: Without the varying adjustment arm end position and this would reduce a work around products "lift": The present brace uses both methods to create/customize lift.

Provided herein is a device and method using pressure sensors to optimize/individualize the present device's lift 1) The basic science research shows that the present device creates more "lift" and accomplished this with less compression than other products tested. (Which is desirable in pregnancy). 2) The inventor did the research with pressure sensors under the brace to measure the amount of lift. Using that data (and some additional testing), the inventor can calculate a formula to estimate the amount of lift required to support the underbelly based on the individuals different body types. Everyone needs a different about of lift to negate the belly weight of pregnancy that leads to biomechanics changes and then back pain. 3) One or more portable BLUETOOTH pressure sensors would be attached by hook and loop fastener into the present device's front and back and communicate with a cell phone App. The "individual" lift required would pre-determined by calculating the excess belly weight. This varies based on the individual, but would be calculated based on the patients: pre-pregnant weight, current weight, gestation term, height, BMI, belly circumference. This would be entered into a cellphone APP which would then help the patient "dial" in the appropriate "individual" lift with the adjustment arms after the brace is closed. (In real time)

Although the invention has been described in example embodiments, those skilled in the art will appreciate that various modifications may be made without departing from the spirit and scope of the invention. It is therefore to be understood that the inventions herein may be practiced other than as specifically described. Thus, the present embodiments should be considered in all respects as illustrative and not restrictive. Accordingly, it is intended that such modifications fall within the scope of the present invention as defined by the claims appended hereto.

I claim:

1. A method of reducing, treating or preventing back pain in an individual during pregnancy or post-partum, comprising shifting the center of gravity in the individual to a desired center of gravity, which desired center of gravity is further toward a posterior side of the individual, comprising applying modifiable lifting forces to a lower abdomen of the individual using a pully system, under the belly of the individual toward the desired center of gravity; and applying one or more vector forces from an anterior side of the individual toward the desired center of gravity, wherein changing the center of gravity is achieved by applying a lumbar support device to the individual, said lumbar support device comprising at least two wings having wing fasteners to enable the wings to fasten to each other across a belly of the individual; and at least two arms connected to each other by an elastic corset assembly, wherein the arms emerge from slits in the wings, said arms having arm fasteners to enable the arms to fasten to each other across, over, or under the belly of the individual; and securing the lumbar support device to the individual by fastening the wings to one another and fastening the arms to one another.

2. The method of claim 1, further comprising selectively modulating hoop stresses by varying the tensioning arms forces that are transferred to the pulley system.

3. The method of claim 1, wherein the lumbar support device is configured such that a fastened arm position, with respect to the individual to whom the lumbar support device is applied, is variable.

4. The method of claim 1, wherein applying the lumbar support device to the individual comprises positioning the lumbar support device on the individual such that a posterior portion of the lumbar support device is across a back of the individual, and securing the lumber support device to the individual comprises positioning and attaching the wings over the abdomen of the individual and fastening the wings to one another, and positioning and attaching arms having an elastomeric corset assembly, together across, over or under the belly to a desired position and tension.

5. The method of claim 4, wherein the arms are positioned and attached before the wings are positioned and attached.

6. An adjustable, modular lumbar support device comprising at least two wings having wing fasteners to enable the wings to fasten to each other across a belly of a user; and at least two arms connected to each other by an elastic corset assembly, wherein the arms emerge from slits in the wings, said arms having arm fasteners to enable the arms to fasten to each other across, over, or under the belly of the user; and wherein the support device is configured with a tension-pulley system to create adjustable and variable tensioning, wherein said arms of said modular lumbar support device form the tension-pulley system configured to produce an uplifting vector force that delivers an underbelly lift required to move a center of gravity of a user of the modular lumbar support device.

7. The lumbar support device of claim 6, further comprising one or more pressure sensors configured to allow a user to dial in a force required to change the center of gravity.

8. The lumbar support device of claim 7, wherein the arms are positioned with respect to a user such that the arms are fastened to one another so as to rest over either the fastened wings or on an upper abdominal belly of the user.

9. The lumbar support device of claim 6, further comprising at least one removable padded panel selected from an anterior panel, a posterior panel and a coronal panel.

10. The lumbar support device of claim 9, further comprising at least one panel configured with an opening to attach the panel to said device by sliding the panel onto the device.

11. The lumbar support device of claim 9, wherein an anterior panel is fastened to the arms via a hook and loop fastener attachment between wing arms and a body of the device.

12. The lumbar support device of claim 9, wherein an anterior panel is configured to be adjusted with hook and loop fasteners to allow positioning by the user in a desired area for comfort.

13. The lumbar support device of claim 6, wherein the lumbar support complies with at least one brace code selected from the group consisting of L0631 US brace code and L0637 US brace code.

14. The lumbar support device of claim 6, further comprising at least one electronic component capable of measuring, calculating, monitoring and/or adjusting one or more forms of data selected from the group consisting of maternal vital signs, fetal vital signs, time, distance, force, lift and pressure.

15. A kit comprising
(1) a lumbar support device of claims 6; and
(2) at least one additional component selected from the group consisting of instructions for application, positioning and/or adjustment of the lumbar support device; a shoulder attachment; an extender; a removable panel, an electronic component, and a dial addition to the lumbar support device.

16. The kit of claim 15, further comprising at least one removable padded panel selected from the group consisting of an anterior panel, a posterior panel, and a coronal panel.

17. The kit of claim 16, wherein the removable padded panels are selected from panels that enable the brace to comply with at least one brace code selected from the group consisting of L0631 and L0637 US brace codes.

18. A system of reducing, treating or preventing back pain in an individual during pregnancy or post-partum, comprising a modular lumbar support device comprising at least two wings having wing fasteners to enable the wings to fasten to each other across a belly of a user; and at least two arms connected to each other by an elastic corset assembly, wherein the arms emerge from slits in the wings, said arms having arm fasteners to enable the arms to fasten to each other across, over, or under the belly of the user; and at least one electronic component capable of detecting and/or monitoring one or more maternal and/or fetal vital signs; and or capable of adjusting the fit of said modular lumbar support device, wherein said arms of said modular lumbar support device form the tension-pulley system configured to produce an uplifting vector force that delivers an underbelly lift required to move a center of gravity of a user of the modular lumbar support device.

19. The system of claim 18, wherein said system is configured to shift the center of gravity in a user of the device, to a desired center of gravity, which desired center of gravity is further toward a posterior side of the user, by a method comprising applying modifiable lifting forces to a lower abdomen of the user using a pully system, under the belly of the user toward the desired center of gravity; and applying one or more vector forces from an anterior side of the user toward the desired center of gravity.

* * * * *